United States Patent
Sanchez-Schmitz et al.

(10) Patent No.: US 10,731,129 B2
(45) Date of Patent: Aug. 4, 2020

(54) METHODS OF EVALUATING IMMUNOGENICITY OF AN AGENT USING AN ARTIFICIAL TISSUE CONSTRUCT

(71) Applicant: CHILDREN'S MEDICAL CENTER CORPORATION, Boston, MA (US)

(72) Inventors: Guzman Sanchez-Schmitz, Brookline, MA (US); Ofer Levy, Boston, MA (US); Chad Stevens, Randolph, MA (US)

(73) Assignee: Children's Medical Center Corporation, Boston, MA (US)

( * ) Notice: Subject to any disclaimer, the term of this patent is extended or adjusted under 35 U.S.C. 154(b) by 830 days.

(21) Appl. No.: 14/383,358

(22) PCT Filed: Mar. 7, 2013

(86) PCT No.: PCT/US2013/029517
§ 371 (c)(1),
(2) Date: Sep. 5, 2014

(87) PCT Pub. No.: WO2013/134464
PCT Pub. Date: Sep. 12, 2013

(65) Prior Publication Data
US 2015/0152385 A1 Jun. 4, 2015

Related U.S. Application Data

(60) Provisional application No. 61/607,796, filed on Mar. 7, 2012, provisional application No. 61/617,874, filed on Mar. 30, 2012.

(51) Int. Cl.
*G01N 33/50* (2006.01)
*C12N 5/0784* (2010.01)
*A61K 35/14* (2015.01)
*A61K 35/44* (2015.01)
*A61K 35/12* (2015.01)

(52) U.S. Cl.
CPC ............ *C12N 5/0639* (2013.01); *A61K 35/14* (2013.01); *A61K 35/44* (2013.01); *A61K 2035/124* (2013.01); *C12N 2500/98* (2013.01); *C12N 2502/28* (2013.01); *C12N 2506/115* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| 7,855,074 B2 * | 12/2010 | Warren ................ C12N 5/0698 435/372 |
| 2007/0178076 A1 | 8/2007 | Drake, III et al. |
| 2009/0297541 A1 | 12/2009 | Ten et al. |
| 2010/0287630 A1 | 11/2010 | Tew et al. |
| 2010/0323401 A1 | 12/2010 | Lewis et al. |

FOREIGN PATENT DOCUMENTS

| WO | 02/40647 A1 | 5/2002 |
| WO | WO 2008108794 A2 | 9/2008 |

OTHER PUBLICATIONS

Koellensperger et al ( Stem Cell, 2006, pp. 1218-1225).*
Ma et al., Immunology. 130(3):374-387 (2010). "Assessing the immunopotency of Toll-like receptor agonists in an in vitro tissue-engineered immunological model."
Randolph et al., Science. 282(5388):480-483 (1998). "Differentiation of monocytes into dendritic cells in a model of transendothelial trafficking."
Randolph et al., J Exp Med. 196(4):517-527 (2002). "The CD16(+) (FcgammaRIII(+)) subset of human monocytes preferentially becomes migratory dendritic cells in a model tissue setting."
Sanchez-Schmitz et al., Sci Transl Med. 3(90):90ps27 (2011). "Development of newborn and infant vaccines."
Sanchez-Schmitz et al., Journal of Immunology 188:166.27 (2012). "A novel human neonatal tissue construct NTC) models age-specific immune responses to Bacille Calmette-Guerin BCG) vaccine."
Stevens et al., PAS Meeting 2012. "Modeling autonomous development and activation of human neonatal monocyte derived dendritic cells in response to vaccine formulations."
Dhir et al., 'A predictive biomimetic model of cytokine release induced by TGN1412 and other therapeutic monoclonal antibodies' Journal of Immunotoxicology, vol. 9, No. 1, pp. 34-42 (Nov. 10, 2011).
Higbee et al., 'An immunologic model for rapid vaccine assessment—a clinical trial in a test tube' Alternatives to Laboratory Animals, vol. 37, No. Supplement 1, pp. 19-27 (2009).
Ma et al., 'Assessing the immunopotency of Toll-like receptor agonists in an in vitro tissue engineered immunological model' Immunology, vol. 130, No. 3, pp. 374-387 (2010).
Malaspina et al., 'In vitro systems to characterize the immune response to HIV-1 and HIV-1 vaccine candidates' NIAID Workshop Report, Bethesda, Aug. 4, 2010 Vaccine, vol. 29, No. 29-30, pp. 4647-4653 (2011).

\* cited by examiner

*Primary Examiner* — Michail A Belyavskyi
(74) *Attorney, Agent, or Firm* — Nixon Peabody LLP; David S. Resnick

(57) ABSTRACT

Artificial tissue constructs (TCs), methods of making the TCs, uses thereof, and kits comprising the TCs are provided. TCs are useful for vaccine evaluation for human adult, human non-newborn, and newborns.

6 Claims, 28 Drawing Sheets

Figure 12

A. Newborn Unstimulated

B. Newborn DTwP 1:100

C. Newborn DTwP 1:10

D. Newborn DTaP 1:100

E. Newborn DTaP 1:10

METHODS OF EVALUATING IMMUNOGENICITY OF AN AGENT USING AN ARTIFICIAL TISSUE CONSTRUCT

CROSS REFERENCE TO RELATED APPLICATIONS

This application is a 35 U.S.C. § 371 National Phase Entry Application of International Application No. PCT/US2013/029517 filed Mar. 7, 2013, which designates the U.S., and which claims benefit under 35 U.S.C. § 119(e) of U.S. Provisional Application No. 61/607,796 filed on Mar. 7, 2012 and U.S. Provisional Application No. 61/617,874 filed Mar. 30, 2012, the contents of each of which are incorporated herein by reference in their entireties.

FIELD OF INVENTION

Embodiments disclosed herein relate to the evaluation of immunomodulators, microbes, microbial components, adjuvants, and vaccines. Specifically, embodiments disclosed herein relate to methods, artificial tissue constructs apparatus and kits for vaccine evaluation for human adults, human newborns and human non-newborns.

BACKGROUND OF THE INVENTION

Over the past decade, efforts have indicated the ability to culture mononuclear cells (MCs) in three-dimensional systems. Indeed, these principles have been incorporated in the development of platforms for the evaluation of adult vaccine responses. However, thus far, published tissue engineering work has not taken into account age-dependent changes in immunity in an organism, some of which depend on differences in soluble components of human autologous plasma. The immune responses of newborns and infants are distinct and not predictable from those of adults due to differences in both their cellular and humoral (i.e., soluble) components. Neonatal leukocytes and in particular monocytes and dendritic cells, demonstrate impairments in migration, Th1-polarizing cytokine production, and antigen-presenting cell (APC)-lymphocyte interactions. Of note, the known tissue engineering systems have employed xenologous materials such as fetal bovine serum, or have employed heat-treated pooled human serum and have therefore not taken into account immunomodulatory components unique to intact autologous neonatal plasma.

SUMMARY

Embodiments disclosed herein relate to tissue constructs, methods of making and using such tissue constructs (TCs), and kits for vaccine evaluation for human adult, human non-newborn and newborns.

It is the goal of the embodiments disclosed herein to provide human tissue constructs that are comprised largely or entirely of human materials with little or no xenologous, (non-human) materials, and are therefore, suitable for vaccine formulation evaluation for humans, and also for the evaluation of candidate immunomodulators, and adjuvants for humans.

Another goal is to provide human tissue constructs suitable for testing vaccines that are to be used in vaccinating newborns. The human tissue constructs described herein are suitable for testing of agents, including but are not limited to immunomodulators, adjuvants, and vaccine formulations. The human tissue constructs allow a person to assess the safety and efficacy of new immune-response stimulating agents in a pre-clinical in vitro setting.

In one embodiment, the purpose of testing serves to assess vaccine formulation safety, vaccine reactogenicity, and/or vaccine toxicity of a new formulation. In one embodiment, the assessment is achieved by generating data with the human tissue constructs disclosed and the new vaccine formulations, and comparing these data with those obtained in similar human tissue constructs for licensed and approved vaccines, i.e., by benchmarking to the known licensed and approved vaccines. The human tissue construct described herein is suitable because the constituents therein more closely resemble and recapitulate the immune cells and immune system of a newborn and a human. Such a human tissue construct is comprised essentially of human materials from newborns and/or a human, non-limiting example include primary leukocytes derived from human cord blood, intact human newborn plasma and human newborn platelet-poor plasma. In addition, the plasma, e.g., platelet-poor plasma is not depleted of components of cell signaling and immune responses, e.g., including, divalent cations, soluble complement, maternal antibodies, and plasma purine-metabolizing enzymes that generate immunomodulatory adenosine, etc.

As used herein, in one embodiment, the term "intact" in the context of plasma or heparinized plasma/blood means that the plasma has not been heat treated. In another embodiment, the term "intact" in the context of plasma or heparinized plasma/blood means that the plasma has not depleted of any plasma components. In some embodiments, the term "intact" and "untouched" are used interchangeably.

As used herein, the term "untouched heparin plasma" where the untouched refers to the plasma means that the plasma has not been heat treated or depleted in any way.

In one embodiment, provided herein is a tissue construct (TC) comprising a cushion of extracellular matrix, a monolayer of human endothelial cells on the top of the matrix cushion (i.e., the cushion of extracellular matrix), and human mononuclear cells (MCs) that have extravasated through the monolayer of human endothelial cells (ECs) and are embedded within and colonized the cushion of extracellular matrix, and have differentiated to migratory dendritic cells.

In one embodiment, provided herein is a method of making such a tissue construct (TC), the method comprising providing a cushion of extracellular matrix, culturing human endothelial cells (ECs) on the cushion of extracellular matrix in the presence of human plasma for a period of time sufficient for the cells to form a monolayer, adding human mononuclear cells (MCs) to the monolayer of human ECs, and culturing the human MCs in the presence of human serum albumin for a period of time sufficient for autonomous extravasation of the MCs through the monolayer of human endothelial cells, thereby facilitating MC colonization of the cushion of extracellular matrix beneath the monolayer of human endothelial cells, and allowing the autonomous differentiation of MCs into migratory dendritic cells.

As used herein, "differentiation of MCs into migratory dendritic cells" means the same as "develop and transform to migratory dendritic cells", and are used interchangeably.

In one embodiment, provided herein is a method of preparing a population of human dendritic cells in vitro, the method comprising introducing an adjuvant/antigen/vaccine/immune-response stimulating agent in the presence of human plasma to a tissue construct (TC) described herein, incubating the TC with the adjuvant/antigen/vaccine formulation/immune-response stimulating agent in the presence of human plasma for a period of time sufficient to allow autonomous generation of differentiated human migratory dendritic cells that have escaped from the matrix cushion and reverse-transmigrated back across the monolayer of human endothelial cells, and collecting the reverse-transmigrated dendritic cells which have developed into immature and mature antigen-presenting cells in the presence of the adjuvant/antigen/vaccine formulation/immune-response stimulating agent.

In another embodiment, provided herein is a method of preparing a population of human dendritic cells in vitro, the method comprising first preparing or providing a tissue construct (TC) comprising extravasated human mononuclear cells (MCs) in a cushion of extracellular matrix with an overlying endothelial monolayer, the human MCs having differentiated therein into migratory dendritic cells, then introducing an adjuvant/antigen/vaccine formulation/immune-response stimulating agent in the presence of human plasma to the tissue construct, incubating the TC with the adjuvant/antigen/vaccine/immune-response stimulating agent in the presence of human plasma for a period of time sufficient to allow reverse-transmigration of the differentiated human migratory dendritic cells from the cushion of extracellular matrix and monolayer of endothelial cells, and collecting the reverse-transmigrated dendritic cells which have developed into immature and mature antigen-presenting cells in the presence of the adjuvant/antigen/vaccine formulation/immune-response stimulating agent.

In another embodiment, provide herein is a method of preparing a population of dendritic cells in vitro, the method comprising: (a) culturing human endothelial cells (ECs) on a cushion of extracellular matrix in the presence of human plasma for a period of time sufficient to obtain a monolayer; (b) introducing human mononuclear cells (MCs) to the monolayer of human ECs; (c) culturing the human MCs in the presence of human serum albumin for a period of time sufficient to allow the human MCs to autonomous extravasate of the monolayer of endothelial cells, colonize the cushion of extracellular matrix and eventually differentiate into migratory dendritic cells; (d) removing non-extravasated MCs after the period of time in step c; (e) introducing to the culture of step d with an adjuvant/antigen/vaccine formulation/immune-response stimulating agent in the presence of human plasma; (f) incubating the culture of step (e) for a period of time sufficient to allow reverse-transmigration of the differentiate migratory dendritic cells from the cushion of extracellular matrix and monolayer of ECs; and (g) collecting the reverse-transmigrated dendritic cells which have developed into immature and mature antigen-presenting cells in the presence of the adjuvant/antigen/vaccine formulation/immune-response stimulating agent.

In one embodiment, provided herein is an in vitro method for evaluating the effectiveness of a vaccine in eliciting an immune response to the vaccine, the method comprising: co-culturing human CD4+ CD45RA+ naïve T cells with a first population of human dendritic cells in the presence of human plasma, wherein the human dendritic cells are antigen-presenting cells developed in the presence of the vaccine formulation being tested and in the presence of human plasma; incubating the co-culture of human dendritic cells and human CD4+ CD45RA+ naïve T cells in the presence of human plasma for a period of time sufficient to cause primary activation and proliferation of the CD4+ CD45RA+ naïve T cells to become CD4+ CD45RO+ T cells; introducing the resultant activated human CD4+ CD45RO+ T cells in culture to a second population of human dendritic cells in the presence of human plasma, wherein the human dendritic cells are antigen-presenting cells developed in the presence of the vaccine formulation being tested and in the presence of human plasma; co-culturing the second population of human dendritic cells and the activated human CD4+ CD45RO+ T cells for a period of time sufficient to cause further activation and proliferation of the CD4+ CD45RO+ T cells in culture; and analyzing for the production of cytokines wherein the presence of cytokines over that in the absence of added dendritic cells indicates that the vaccine formulation being tested is an effective vaccine in stimulating a human immune response. In one embodiment, the production of prostaglandin E2 ($PGE_2$) over that in the absence of added dendritic cells indicates that the vaccine formulation being tested is an effective vaccine in stimulating a human immune response. Very high PGE2 production induced by a novel vaccine formulation relative to licensed vaccines may also indicate potential for reactogenicity of a vaccine (eg, local reaction or fever).

In one embodiment, provided herein is an in vitro method for evaluating the effectiveness of an adjuvant/antigen/vaccine formulation/immune-response stimulating agent in eliciting an immune response to an antigen/vaccine formulation/immune-response stimulating agent, the method comprising: co-culturing human CD4+ CD45RA+ naïve T cells with a first population of human dendritic cells in the presence of human plasma, wherein the human dendritic cells are antigen-presenting cells developed in the presence of the adjuvant/antigen/vaccine formulation/immune-response stimulating agent being tested and in the presence of human plasma; incubating the co-culture of human dendritic cells and human CD4+ CD45RA+ naïve T cells in the presence of human plasma for a period of time sufficient to cause primary activation and proliferation of the CD4+ CD45RA+ naïve T cells to become CD4+ CD45RO+ T cells; introducing the resultant activated human CD4+ CD45RO+ T cells in culture to a second population of human dendritic cells in the presence of human plasma, wherein the human dendritic cells are antigen-presenting cells developed in the presence of the an adjuvant/antigen/vaccine formulation/immune-response stimulating agent being tested and in the presence of human plasma; co-culturing the second population of human dendritic cells and the activated human CD4+ CD45RO+ T cells for a period of time sufficient to cause further activation and proliferation of the CD4+ CD45RO+ T cells in culture; and analyzing for the production of cytokines wherein the presence of cytokines over that in the absence of added dendritic cells indicates that the adjuvant/antigen/vaccine formulation/immune-response stimulating agent being tested is an effective vaccine in stimulating or promoting the stimulation (e.g. in the case of an adjuvant) of a human immune response. In one embodiment, the production of $PGE_2$ over that in the absence of added dendritic cells indicates that the vaccine formulation being tested is an effective vaccine in stimulating a human immune response.

In one embodiment, provided herein is an in vitro method for evaluating the effectiveness of an adjuvant/antigen/vaccine formulation/immune-response stimulating agent in eliciting an immune response to an antigen/vaccine formulation/immune-response stimulating agent, the method comprising: providing a first and second population of human dendritic cells, wherein the human dendritic cells are antigen-presenting cells developed in the presence of the adjuvant/antigen/vaccine formulation/immune-response stimulating agent being tested and in the presence of human plasma; co-culturing human CD4+ CD45RA+ naïve T cells with the first population of human dendritic cells in the presence of human plasma; incubating the co-culture of human dendritic cells and human CD4+ CD45RA+ naïve T cells in the presence of human plasma for a period of time sufficient to cause activation and proliferation of the CD4+ CD45RA+ naïve T cells to become CD4+ CD45RO+ T cells; introducing to the resultant activated human CD4+ CD45RO+ T cells in culture to the second population of human dendritic cells in the presence of human plasma; co-culturing the second population of human dendritic cells and the activated human CD4+ CD45RO+ T cells for a period of time sufficient to cause further activation and proliferation of the CD4+ CD45RO+ T cells in culture; and analyzing for the production of cytokines wherein the presence of cytokines over that in the absence of added dendritic cells indicates that the adjuvant/antigen/vaccine formulation/immune-response stimulating agent is an effective adjuvant/antigen/vaccine formulation/immune-response stimulating agent respectively in stimulating or promoting (e.g., an adjuvant) the stimulation of a human immune response. In one embodiment, the production of $PGE_2$ over that in the absence of added dendritic cells indicates that the vaccine formulation being tested is an effective vaccine in stimulating a human immune response. In one embodiment, the human plasma is human PPP. In one embodiment, the first and second population of human dendritic cells, and the human CD4+ CD45RA+ naïve T cells are autologous, that is the cells are all derived from one individual human. In another embodiment, the pattern of cytokines produced, e.g., Th1, Th2, Th17 can also be analyzing and compared to those cytokine patterns produced in the absence of added dendritic cells and in comparison to licensed vaccines. Comparison with licensed vaccines is known as benchmarking.

In one embodiment, provided herein is an in vitro method for evaluating the effectiveness of an adjuvant/antigen/vaccine formulation/immune-response stimulating agent in eliciting an immune response to the adjuvant/antigen/vaccine formulation/immune-response stimulating agent, the method comprising: introducing an adjuvant/antigen/vaccine formulation/immune-response stimulating agent to a tissue construct in the presence of human plasma, wherein the tissue construct was previously prepared by: providing a cushion of extracellular matrix comprising human extracellular matrix material such as collagen and/or fibronection, incubating the extracellular matrix cushion in the presence of glucose-6-phosphate for a sufficient period of time to allow collagen maturation, seeding the cushion of extracellular matrix with human ECs, culturing the human ECs to a confluent monolayer in the presence of human plasma, introducing human MCs to the confluent monolayer of human ECs in the presence of non-heat inactivated human serum albumin, incubating for a period of time sufficient to allow the MCs to undergo autonomous extravasation of the confluent monolayer of human endothelial cells wherein the extravasated human MCs having differentiated to migratory dendritic cells, and removing the non-extravasated human MCs; incubating the tissue construct for a period of time sufficient for the differentiated migratory dendritic cells to reverse-transmigrated the confluent monolayer of human ECs, the differentiated migratory dendritic cells having developed to antigen-presenting dendritic cells in the presence of the adjuvant/antigen/vaccine formulation/immune-response stimulating agent added; collecting the reverse-transmigrated dendritic cells; co-culturing the antigen-presenting dendritic cells with human CD4+ CD45RA+ naïve T cells in the presence of human plasma; incubating the co-culture of dendritic cells and naïve T cells in the presence of human plasma for a period of time sufficient to cause activation and proliferation of the CD4+ CD45RA+ naïve T cells to become CD4+ CD45RO+ T cells; introducing the resultant activated human CD4+ CD45RO+ T cells to a second population of human dendritic cells in the presence of human plasma; co-culturing the dendritic cells and activated human CD4+ CD45RO+ T cells in the presence of human plasma for a period of time sufficient to cause further activation and proliferation of the human CD4+ CD45RA+ activated T cells in culture; and analyzing for the production of cytokines wherein the presence of cytokines over that in the absence of added dendritic cells indicates that the adjuvant/antigen/vaccine formulation/immune-response stimulating agent is an effective adjuvant/antigen/vaccine formulation/immune-response stimulating agent respectively in stimulating or promoting the stimulation of a human immune response. In one embodiment, the production of $PGE_2$ over that in the absence of added dendritic cells indicates that the vaccine formulation being tested is an effective vaccine in stimulating a human immune response. In one embodiment, the human plasma is human PPP. In one embodiment, the first and second population of human dendritic cells, and the human CD4+ CD45RA+ naïve T cells are autologous, that is the cells are all derived from one individual human. In one embodiment, the human plasma is from a human newborn. In one embodiment, the first and second population of human dendritic cells, and the human CD4+ CD45RA+ naïve T cells are autologous and derived from a human newborn. In other embodiments, measurement of other biomarkers such as secreted cytokines, intracellular cytokines, surface cell markers and lymphocyte proliferation are performed to assess elicitation of an immune response. In one embodiment, the production of $PGE_2$ over that in the absence of added dendritic cells indicates that the vaccine formulation being tested is an effective vaccine in stimulating a human immune response. Comparison of the measurement of these biomarkers against proper negative and positive controls (i.e., "benchmarking") such as unstimulated condition, stimulation with an unrelated antigen and/or licensed vaccines can, indicate whether the candidate novel adjuvant/antigen/vaccine formulation/immune-response stimulating agent is likely safe and an effective vaccine in stimulating primary and/or secondary/recall human immune responses in a human, e.g., a human newborn.

In one embodiment of any methods described, the first and second populations of human dendritic cells are developed in the presence of the same adjuvant/antigen/vaccine formulation/immune-response stimulating agent that is being evaluated. In one embodiment, the first and second populations of human dendritic cells are developed in the same TC; that is the antigen-presenting cells are developed at the same time and same procedure. For example, the collected antigen-presenting cells are divided into two batches, one batch is the first population of human dendritic cells that is incubated with CD4+ CD45RA+ naïve T cells. The remaining batch is the second population of human dendritic cells that is incubated with CD4+ CD45RO+ T cells.

In one embodiment of any of the methods or TC described, the human plasma is human platelet-poor plasma. The measurement of the production of cytokines secreted is used to assess whether an immune response, e.g., an adaptive immune response have been elicited in the presence of the antigen-presenting dendritic cells. In other embodiments, analyses of other parameters are done to assess whether there is an elicitation of an immune response in the presence of the antigen-presenting dendritic cells. Non-limiting examples of parameters that can be studied include intracellular cytokines, $PGE_2$, surface cell markers and cell proliferation. These measurements can be compared against appropriate negative and positive controls, such as unstimulated condition (e.g., in the absence of an antigen-presenting dendritic cells) and stimulation with an unrelated antigen, in order to determine whether the adjuvant/antigen/vaccine formulation/immune-response stimulating agent is an effective adjuvant/antigen/vaccine formulation/immune-response stimulating agent in stimulating primary and/or secondary/recall human immune responses respectively. Such responses can be "benchmarked" by comparison to licensed and government approved immunomodulators, pediatric and adult vaccine formulations. In one embodiment, the first and second population of human dendritic cells, and the human CD4+ CD45RA+ naïve T cells are autologous, that is the cells are all derived from one individual human.

In one embodiment, provided herein is a kit for making a human tissue construct described herein. In another embodiment, provided herein is a kit for preparing a population of dendritic cells in vitro. In another embodiment, provided herein is a kit for evaluation the efficacy of an adjuvant/antigen/vaccine/immune response stimulating agent. The kit comprises the components necessary to prepare a human tissue construct, the components include but are not limited to at least a container for holding or containing the tissue construct, e.g., tissue culture vessel, at least one type of extracellular matrix, human endothelial cells, and glucose-6-phosphate. Accordingly, provided herein is a kit comprising at least a container for holding or containing a human tissue construct; at least one extracellular matrix; and glucose-6-phosphate. The kit can comprise also human endothelial cells. Alternatively, the kit provides at least one tissue construct. In one embodiment, the kit is used for age-specific evaluation of the efficacy of an adjuvant/antigen/vaccine/immune response stimulating agent.

As used herein, "age-specific evaluation of efficacy" means evaluating the efficacy of an adjuvant/antigen/vaccine/immune response stimulating agent in eliciting an immune response in a human of a specific age or age group e.g., a newborn, an adolescent, a child, an adult or an adult is between 22-30, 31-40, 41-50 etc.

In one embodiment of any of the methods or TCs described, the cushion of extracellular matrix comprising collagen. In another embodiment of any of the methods or TCs described, the cushion of extracellular matrix comprises at least collagen.

In other embodiments of any of the methods or TCs described, the collagen is human collagen, bovine collagen or porcine collagen.

In other embodiments of any of the methods or TCs described, the collagen is Type 1 collagen. In one embodiment of any of the methods or TCs described, the human collagen is human Type 1 collagen.

In one embodiment of any of the methods or TCs described, the collagen is glycosylated or glycated. In one embodiment of any of the methods or TCs described, the collagen is glycosylated or glycated in the presence of glucose-6-phosphate. As used herein, glycation (sometimes called non-enzymatic glycosylation) is the result of, typically covalent, bonding of a protein or lipid molecule with a sugar molecule, such as fructose or glucose, without the controlling action of an enzyme. Glycated collagen has added sugars that are not the result of enzymatically catalyzed reaction. As used herein, glycosylation is the enzyme-controlled addition of sugars to protein or lipid molecules. Glycosylated collagen has added sugars that are added by enzymatically catalyzed reaction. Glycosylation or glycation of collagen rendering the collagen amenable to culturing endothelial cells on top of it. In one embodiment of any of the methods or TCs described, the added sugars on the glycosylated or glycated collagen provide adhesion sites of attachment of the endothelial cells.

In one embodiment of any of the methods or TCs described, the human collagen used is matured human collagen. As used herein, the term "mature collagen" is defined as glycosylated or glycated collagen in the presence of glucose-6-phosphate. In one embodiment of any of the methods or TCs described, the human collagen is matured in the presence of glucose-6-phosphate for at least 48 h. In another embodiment of any of the methods or TCs described, the human collagen is human collagen matured in the presence of glucose-6-phosphate for up to 5 days. In another embodiment of any of the methods or TCs described, the human collagen is human collagen matured in the presence of glucose-6-phosphate for a period of about 2 to about 5 days.

In one embodiment of any of the methods or TCs described, the cushion of extracellular matrix further comprises fibronectin. In one embodiment of any of the methods or TCs described, the fibronectin is human fibronectin. In one embodiment of any of the methods or TCs described, the cushion of extracellular matrix comprises at least a mixture of collagen and fibronectin. In another embodiment of any of the methods or TCs described, the cushion of extracellular matrix comprises at least a mixture of human collagen and human fibronectin.

In one embodiment of any of the methods or TCs described, the ECs are human ECs. In one embodiment, the ECs are human primary ECs.

In one embodiment of any of the methods or TCs described, the human ECs are cultured and grown in intact human plasma that is the plasma has not been fractionated into platelet rich and platelet poor fractions. Non-limiting, other exemplary of intact human plasmas are intact human newborn plasma and intact human adult plasma. In one embodiment of any of the methods or TCs described, the human primary ECs are cultured in the presence of intact human newborn plasma. In one embodiment of any of the methods or TCs described, the human newborn plasma is pooled human newborn plasma from plasma collected from more than one newborn.

In one embodiment of any of the methods or TCs described, the human primary ECs are obtained from one single donor. In one embodiment of any of the methods or TCs described, where the human primary ECs are used, the human primary ECs are obtained from human umbilical cord, placenta, or human cadaver tissues.

In one embodiment of any of the methods or TCs described, the human primary endothelial cells are cultured to a confluent monolayer. In one embodiment, the confluent monolayer is at least 90% confluent. In other embodiment, the confluent monolayer is about 90% to about 100% confluent. In other embodiment, the confluent monolayer is about 95% to about 100% confluent. In another embodiment, the confluent monolayer is about 100% confluent.

In one embodiment of any of the methods or TCs described, the period of time to obtain a monolayer is at least 24 h. In other embodiment, the period of time to obtain a monolayer is about 24 h to about five days.

In one embodiment of any of the methods or TCs described, the human plasma, human platelet poor plasma or human serum albumin is obtained or derived from a newborn or a non-newborn, wherein a non-newborn is an adult, an adolescent or a child. In one embodiment of any of the methods or TCs described, the human plasma is human newborn plasma.

In one embodiment of any of the methods or TCs described, the human plasma, human platelet poor plasma or human serum albumin is not heat-inactivated. In another embodiment of any of the methods or TCs described, the human plasma, human platelet poor plasma or human serum albumin is heat inactivated.

In one embodiment of any of the methods or TCs described, the human plasma is autologous intact plasma to the human MCs, dendritic cells and/or the CD4+ CD45RA+ naïve T cells used in the methods and tissue constructs described herein. In another embodiment of any of the methods or TCs described, the human plasma is non-heat inactivated human plasma. In another embodiment of any of the methods or TCs described, the human plasma is human platelet poor plasma.

In one embodiment of any of the methods or TCs described, the human plasma is used at at least 40%. In one embodiment of any of the methods or TCs described, the human plasma is used at about 40% to about 100%. In one embodiment, the human plasma is used at about 50%.

In one embodiment of any of the methods or TCs described, the human platelet poor plasma is used at a concentration of at least 50%. In one embodiment of any of the methods or TCs described, the human platelet poor plasma is used at about 50% to about 100%. In one embodiment of any of the methods or TCs described, the human platelet poor plasma is used at about 100%.

In one embodiment of any of the methods or TCs described, the human serum albumin is used at least 0.05%. In one embodiment of any of the methods or TCs described, the human platelet poor plasma is used at about 0.05% to about 10%. In one embodiment of any of the methods or TCs described, the human platelet poor plasma is used at about 0.1%.

In one embodiment of any of the methods or TCs described, the human plasma, human platelet poor plasma or human serum albumin does not contain a chelating agent.

In one embodiment of any of the methods or TCs described, the human plasma, human platelet poor plasma or human serum albumin is prepared with heparin.

In one embodiment of any of the methods or TCs described, the human plasma, human platelet poor plasma or human serum albumin is prepared in the absence of a chelating agent.

In one embodiment of any of the methods or TCs described, the chelated ions are magnesium or calcium.

In one embodiment of any of the methods or TCs described, the human plasma, human platelet poor plasma or human serum albumin is pooled from more than one donor, e.g., a newborn. In another embodiment, the human plasma, human platelet poor plasma or human serum albumin is from one donor.

In one embodiment of any of the methods or TCs described, the human plasma, human platelet poor plasma or human serum albumin is obtained from human umbilical cord blood, placental blood or circulating peripheral blood.

In one embodiment of any of the methods or TCs described, the human serum albumin is not heat inactivated or not heat treated. In one embodiment of any of the methods or TCs described, the human serum albumin is pyrogen-free. In one embodiment of any of the methods or TCs described, the human serum albumin is a clinical grade human serum albumin.

In one embodiment of any of the methods or TCs described, the human plasma, human serum albumin, human platelet poor plasma, human ECs, human MCs, and human CD33+ and/or CD14+ selected monocytes used has been previously been cryopreserved.

In one embodiment of any of the methods or TCs described, the human MCs or human CD33+ and/or CD14+ selected monocytes are derived from a newborn or a non-newborn, wherein a non-newborn is an adult, an adolescent or a child. In one embodiment of any of the methods or TCs described, the human MCs or human CD33+ and/or CD14+ selected monocytes are human newborn MCs or human newborn CD33+ and/or CD14+ selected monocytes.

In one embodiment of any of the methods or TCs described, the human MCs or human CD33+ and/or CD14+ selected monocytes are derived from one donor. In one embodiment, the human MCs or human CD33+ or CD14+ selected monocytes are not pooled from more than one donor.

In one embodiment of any of the methods or TCs described, the human MCs or human CD33+ and/or CD14+ selected monocytes are obtained from human umbilical cord blood, placenta, bone marrow or circulating peripheral blood.

In one embodiment of any of the methods or TCs described, the human MCs are human CD33+ and/or CD14+ selected monocytes.

In one embodiment of any of the methods or TCs described, the human MCs or human CD33+ and/or CD14+ selected monocytes are cultured in the presence of human serum albumin.

In one embodiment of any of the methods or TCs described, the human MCs or human CD33+ and/or CD14+ selected monocytes are not cultured in the presence of exogenous cytokines or immune response stimulating agent. Non-limiting examples of exogenous cytokines include GM-CSF and IL-4. In one embodiment of any of the methods or TCs described, the human MCs or human CD33+ and/or CD14+ selected monocytes are not cultured in the presence of GM-CSF. In another embodiment of any of the methods or TCs described, the human MCs or human CD33+ and/or CD14+ selected monocytes are not cultured in the presence of exogenously added IL-4. In another embodiment of any of the methods or TCs described, the human MCs or human CD33+ and/or CD14+ selected monocytes are not cultured in the presence of exogenously added GM-CSF and IL-4.

In one embodiment of any of the methods or TCs described, the human CD33+ and/or CD14+ monocytes or human MCs and the human platelet poor plasma are autologous, meaning they come from one donor, i.e., the same donor.

In one embodiment of any of the methods or TCs described, the period of time sufficient to allow the human MCs or human CD33+ and/or CD14+ monocytes cells to autonomous extravasation of the monolayer of endothelial cells and colonize the cushion of extracellular matrix is at least 0.5 h.

In one embodiment of any of the methods or TCs described, the period of time sufficient to allow the human MCs or human CD33+ and/or CD14+ monocytes to autonomous extravasation of the monolayer of endothelial cells and colonize the cushion of extracellular matrix is about 0.5 h to about 4 h.

In one embodiment of any of the methods or TCs described, the period of time sufficient to allow the human MCs or human CD33+ and/or CD14+ monocytes to autonomous extravasation of the monolayer of endothelial cells and colonize the cushion of extracellular matrix is about 1.5 h to about 2 h.

In one embodiment of any of the methods or TCs described, the adjuvant/antigen/immune response stimulating agent is any agent that can induce or stimulate development, transformation and/or differentiation of the human dendritic cells to become antigen-presenting dendritic cells, the human dendritic cells being derived from human MCs or human CD33+ and/or CD14+ monocytes.

In one embodiment of any of the methods or TCs described, the immune response stimulating agent is a vaccine.

In one embodiment of any of the methods or TCs described, the antigen or immune response stimulating agent is an adjuvant.

In one embodiment of any of the methods or TCs described, the adjuvant, antigen, vaccine or immune response stimulating agent is a pathogen. In one embodiment of any of the methods or TCs described, the pathogen is a fragment/incomplete portion thereof or a whole intact pathogen.

In one embodiment of any of the methods or TCs described, the period of time sufficient to allow reverse-transmigrated of the human dendritic cells from the monolayer of endothelial cells is at least 24 h.

In one embodiment of any of the methods or TCs described, the period of time sufficient to allow reverse-transmigrated of the human dendritic cells from the monolayer of endothelial cells is about 24 to about 48 h.

In one embodiment of any of the methods or TCs described, the period of time sufficient to allow reverse-transmigrated of the human dendritic cells from the monolayer of endothelial cells is about 48 h.

In one embodiment of any of the methods or TCs described, the human CD4+ CD45RA+ naïve T cells are CD45RO negative.

In one embodiment of any of the methods or TCs described, the human CD4+ CD45RA+ naïve T cells, the dendritic cells and the human platelet poor plasma are autologous, meaning they come from one donor.

In one embodiment of any of the methods or TCs described, the human platelet poor plasma is not heat inactivated.

In one embodiment of any of the methods or TCs described, the period of time sufficient to cause activation of the naïve T cells in culture is at least one day.

In one embodiment of any of the methods or TCs described, the period of time sufficient to cause activation of the naïve T cells in culture is at least 7 days, about 7 days, or about 7 to about 21 days.

In one embodiment of any of the methods or TCs described, the adjuvant/antigen/vaccine/immune response stimulating agent being evaluated is the same adjuvant/antigen/vaccine/immune response stimulating agent used in vitro to produce the first and second population of dendritic cells used in evaluating the adjuvant/antigen/vaccine/immune response stimulating agent In one embodiment of any of the methods or TCs described, the methods of in vitro evaluation of vaccine efficacy further comprising analyzing the activated T cells for cell proliferation wherein an increase in cell proliferation or cell number over that in the absence of added dendritic cells indicates that the adjuvant/antigen/vaccine/immune response stimulating agent being evaluated is effective in stimulating human naïve newborn antigen-specific immune response.

In one embodiment of any of the methods or TCs described, the methods of in vitro evaluation of vaccine efficacy further comprising challenging the cells in culture of activated T cells with a third population of dendritic cells prior to analysis for cytokines and cell proliferation, wherein the third population of dendritic cells were exposed to the same adjuvant/antigen/vaccine/immune response stimulating agent used in producing the first and second population of dendritic cells used in the method.

In one embodiment of any of the methods or TCs described, the third population of antigen-vaccinated human newborn dendritic cells is also produced with the same antigen that is being evaluated.

In one embodiment of any of the methods or TCs described, non-limiting the cytokine to be analyzed is selected from a group consisting of IL-1β, IL-2, IL-4, IL-10, IL-12, IFN-gamma and TNF-alpha. Cytokine concentrations induced in the tissue constructs by novel vaccine formulations can be compared to those induced by licensed vaccines in order to benchmark and assess the likelihood that a novel formulation may be too reactogenic and potentially toxic (e.g., if the novel formulation induces much higher levels of pro-inflammatory cytokines).

BRIEF DESCRIPTION OF THE DRAWINGS

FIG. 12A-12E show that low doses of DTwP-containing vaccine induces greater damage to NTC endothelial monolayers than does DTaP. NTCs were colonized with cryopreserved MCs and left unstimulated (A) or were stimulated with (B) DTwP 1:100, (C) DTwP 1:10, (D) DTaP 1:100, or (E) DTaP 1:100.

FIG. 16 shows that in vitro maturation of human collagen with glucose-6-phosphate, and the use of human newborn plasma enable efficient and rapid engineering of complete human TCs. Circled indicate areas where the collagen substrate are not covered with attached cells, meaning non-monolayer formed.

DETAILED DESCRIPTION OF THE INVENTION

Figure 1:
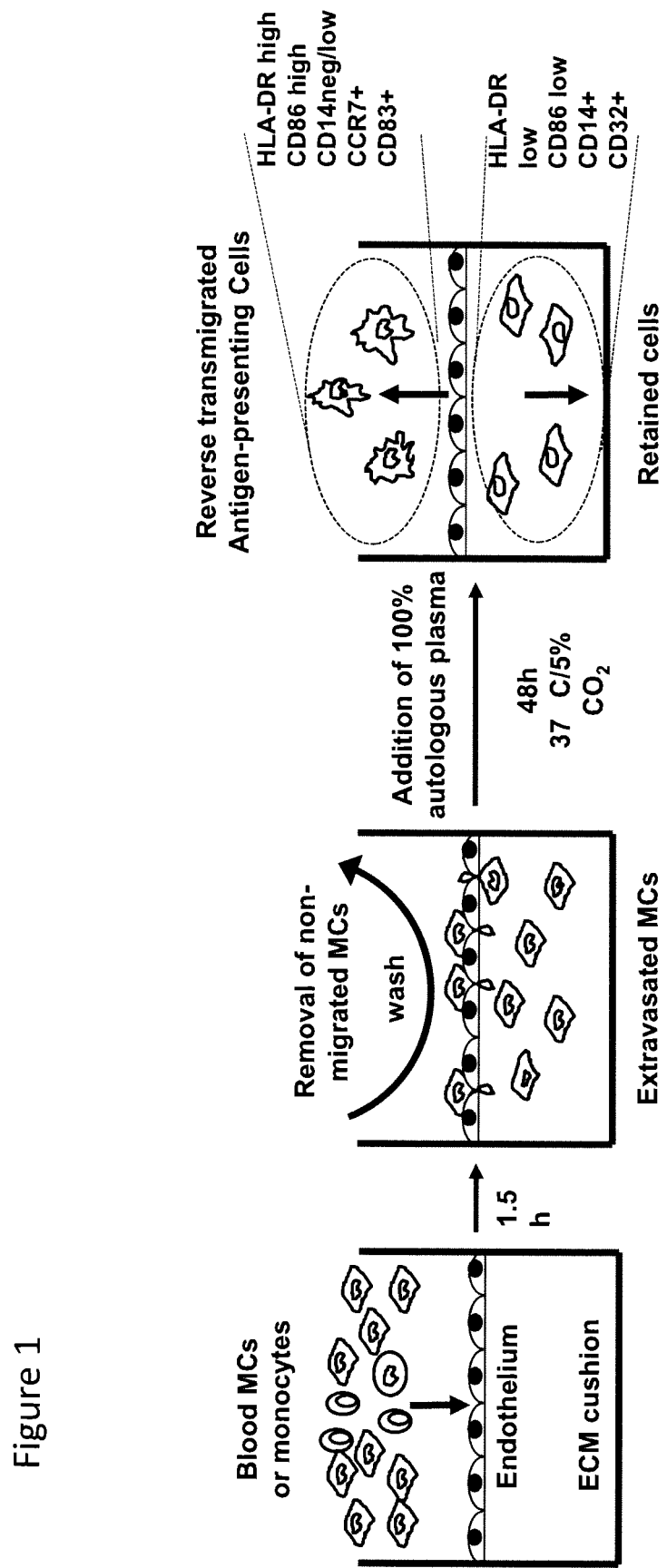
FIG. 1 is a schematic diagram of the elements that comprise the tissue construct (TCs), its colonization by mononuclear cells (MCs), and the reverse transmigration of antigen-presenting dendritic cells.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, the term "comprising" or "comprises" is used in reference to tissue constructs and methods, and respective component(s) thereof, that are essential to the embodiments of the tissue constructs and methods, yet open to the inclusion of unspecified elements, whether essential or not. The use of "comprising" indicates inclusion rather than limitation.

Embodiments disclosed herein relate to tissue constructs, methods of making and using such tissue constructs (TCs), and kits for vaccine evaluation for human adult, human newborn, human infants, human adolescents or human children. The kits can also be for evaluation of an adjuvant, an antigen, a vaccine formulation, or an immune-response stimulating agent for human adult, human newborn, human infants, human adolescents or human children.

Embodiments disclosed herein are based on the observation that currently known TCs and methods of vaccine evaluation specifically target an adult immune system and do not specifically address the newborns or neonatal immune system which is very different from the adult immune system. Moreover, the current TCs and related methods that employ non-human xenologous materials and non-intact non-autologous, often xenologous, plasma/serum (e.g., fetal bovine serum) do not recapitulate the in vivo immune environment of a human, adult or newborn because the fluid phase factors play an important role in immune responses.

As used herein, the term "newborn" refers to a human infant recently or just and lasting through the $28^{th}$ day following birth or the first four weeks after birth. The terms "newborn" and "neonatal" are used interchangeably.

Newborns and young infants have an increased risk of microbial infection. The World Health Organization estimates that over 2,000,000 newborns and infants under 6 months of age die every year due to infection. There is therefore an unmet medical need to prevent these diseases through early in life vaccination.

Neonatal antigen (Ag)-presenting cells (APCs) have a reduced ability to mount Th1-polarizing responses. Newborns also show impairment in Ag-specific memory responses and have distinct immune-modulating components in plasma, including low complement levels, increased inhibitory adenosine, and maternal antibodies (Abs). These distinctive features may contribute to the distinct immune responses of newborns and infants and to their susceptibility to infection.

Newborns and infants suffer frequent infection and demonstrate impaired responses to many vaccines thereby frustrating efforts to protect this vulnerable population. The susceptibility of newborns to infection and their impaired vaccine responses have been ascribed to distinct immunity of the newborn. For example, the neonatal humoral immunomodulatory components are different from those of an adult. Newborns have lower complement levels, lower plasma concentrations of antimicrobial proteins and peptides, high concentration of immune-modulatory adenosine (selectively inhibits production of Th1-polarizing cytokines), have placenta-derived mediators such as Transforming Growth Factor-$\beta$, progesterone, and prostaglandin E2 and have interfering transplacental maternal antibodies. In addition, neonatal leukocyte impairments include high abundance of functionally immature and tolerogenic recent thymic emigrants (naïve T cells), dominance of transitional B cells (impaired T-independent B cell antibody responses), diminished TLR-mediated Th1 polarizing responses (lower Th1:Th2 ratio), lower tumor necrosis Factor (TNF), interferon-$\alpha$ (IFN-$\alpha$), and IFN-$\gamma$, reduced single-cell polyfunctional responses, weaker CD4 lymphoproliferation, lower T cell help to B cells, higher TLR-mediated IL-6 by monocytes and monocyte-derived DCs, and increased number and activity of inhibitory regulatory T cells (Treg cells). Therefore, in this context, characterizing distinct aspects of newborn immunity is important for translational development of new pediatric adjuvants, immunomodulatory agents, vaccine formulations and therapeutics designed for the newborn.

A key challenge in studying human immunity is modeling in vitro immune reactions in a physiologically-relevant manner for pre-clinical assessment of safety and efficacy of immunomodualtors, adjuvants and vaccine formulations. Key to responses to vaccines are antigen-presenting cells (APCs), leukocytes that process vaccinal antigens, present them to lymphocytes in the context of MHC-II, produce co-stimulatory signals and thereby trigger adaptive immune responses. Among the most potent and active APCs are dendritic cells (DCs). Activation of circulating blood monocytes (Mos) can induce their differentiation into Mo-derived dendritic cells (MoDCs). Most published studies of neonatal APCs have focused on MoDCs derived by culture of Mos onto plastic culture plates and treatment with high concentrations of exogenous cytokines such as IL-4 and GM-CSF. Although these exogenous cytokine-driven DCs are useful model system, their relationship to DCs that exist in vivo does not fully recapitulate the true in vivo immune environment in a subject. Indeed, multiple variables affect immune responses, including age of the study subject, the composition of culture media and inclusion of plasma, as well as interactions of leukocytes with endothelial cells and with the extracellular matrix.

Immunization of newborns and young infants provides important benefits to reduce the burden of early life infection. Birth is the most reliable point of healthcare contact worldwide, and thus neonatal immunization would provide higher vaccination coverage and will narrow the window of susceptibility inherent to many 2/4/6 month immunization schedules.

While pediatric vaccines represent the majority of the vaccine market, getting a new vaccine out represents a huge investment. It is known that from discovery and preclinical assessment going all the way down to clinical trials, registration and production, a drug candidate can cost a billion dollars and more than 10 years of work. One important reason for this excessive cost and time is the high failure rate observed at late stages in development. It is generally accepted that animal testing are helpful but not 100% reliable in predicting human immune responses. One could argue then that more reliable preclinical assessment of vaccines candidates could help increase success rate. From here, the idea of using primary human cultures that faithfully recapitulate the immune responsiveness to vaccines as observed in vivo becomes highly appealing; and this is particularly true for newborn vaccines where animal models and adult human cells for preclinical assessment are not predictive of human neonatal and infant responses. A related key need is to improve preclinical assessment of the safety of candidate immunomodulators, adjuvants or vaccine formulations to exclude those that may be too reactogenic/toxic. Examples of reactogenicity in vivo include local swelling and pain, fevers, febrile seizures, and other more serious adverse events (see Ahmed, S S et al., Sci. Trans. Med. 2011).

Vaccination at birth has been successfully proven in veterinary medicine with oral in utero immunization of sheep and poultry industry routinely vaccinating in ovo. Neonatal vaccination can also be safe and effective in human newborns with vaccines such as BCG (*Mycobacterium bovis*) for tuberculosis and HBV for hepatitis B. However, the number of vaccines that have proven safe and effective at birth are very limited due in part to incomplete characterization of neonatal immune responses. Studies of adults are not predictive of neonatal responses as growing evidence indicates that newborns manifest a distinct skew to their innate and adaptive immune responses (PrabhuDas M, et al., Nat, Immunol. 2011 March; 12(3):189-94).

Adjuvants are vaccine components that enhance immunogenicity of vaccinal antigens in vivo. Although there has been a great increase in information regarding candidate adjuvants, few are currently approved for use in human vaccines. Alum, MF59 and naturally occurring endotoxins derived from antigens' manufacturer are the most common Besides, this limitation, there is the need to explore new adjuvants that could be effective and safe for newborn babies.

Given the unmet need for safe and effective vaccines to be given in early life, an in vitro test system that uses primary cells of human newborn origin was developed. Such a system provides more accurate data of expected newborn immune reactogenicity to vaccines. Moreover, developing a wholly human in vitro test system that do not use non-human xenologous materials would also provide more accurate data of expected immune reactogenicity to vaccines when testing human newborns and human non-newborns, e.g., adults, adolescents and children. It is encompassed herein that the age of the individuals from which cells (i.e., newborns) were obtained and the complexity inherent to the fluid/plasma phase of the age-matched individual would be taken into account in the various embodiments of the in vitro test systems disclosed.

In 1998, Gwendalyn J. Randolph published an article demonstrating how autonomous extravasated monocytes in vitro were autonomously differentiating into strong APCs after 48 hours of stimulation (Science October 16; 282 (5388): 480-3). She used human primary endothelial cells, and adult peripheral blood mononuclear cells (PBMCs) in a tissue construct setting. However, she employed M199 media with 20% heat-inactivated heterologous human serum that does not reflect the immune-modulating bioactivities of untouched autologous human plasma. Similar systems using only adult cells are described in U.S. Patent Publication No. US20100287630 and US20050282148. Of note, all these systems have used heat-treated fetal calf serum or heat-treated human plasma that do not reflect the bioactivity of unmodified autologous heparinized, cryopreserved plasma that were used in the tissue construct (TC) work comprised in the in vitro test system described herein. Cation chelants are the standard anticoagulant used in general. The non-removal of these cations plays a role in much better (in vivo-like) bioactivity. Moreover, none of the published studies or patents teaches the use of neonatal, cord or placenta blood cells, non-heated plasma or take into consideration the plasma adensoine system known to exert profound effects on the responsiveness of primary leukocytes, especially neonatal cells. (Levy O. J. Immunol 2006; Coombs, M R P et al., Expert Reviews in Anti-Infective Therapy 2011). Furthermore, none of the published studies or patents teaches the use of only human derived materials for making the TCs that evaluate the immune reactogenicity to vaccines in humans.

Disclosed herein are three-dimensional microphysiologic, wholly human neonatal tissue constructs (NTCs) and wholly human non-neonatal tissue constructs which are referred herein as adult tissue constructs (ATCs). These wholly human TCs allow the characterization of autonomously developed monocyte-derived dendritic cells (MoDCs) and their interaction with autologous lymphocytes under more physiological conditions, conditions that are more closely recapitulate the in vivo environment of a human.

In one embodiment, the NTC can be used as a test for evaluating the effectiveness of newborn vaccines. Embodiments of the in vitro test system comprising NTCs use human leukocytes and about 50% to about 100% autologous human heparinized platelet-poor plasma from newborn cord blood or placenta-derived blood. The NTC is an immune-reactogenic 3-dimensional microvascular interstitium made from primary human cells of newborn origin. Embodiments of the TC comprise a confluent quiescent monolayer of primary human umbilical vein endothelial cells (HUVEC) on an extracellular matrix (ECM) cushion with autonomously extravasated human cord blood mononuclear leukocytes. In one embodiment, the NTC comprises 100% autologous heparinized plasma and gyroscopic movement applied during testing to model circulation.

As used herein, the terms "leukocytes" and "lymphocytes" are used interchangeably. Leukocytes are white blood cells. They constitute the immune cells of the body.

In some embodiment, the NTC is tested when it has (1) a confluent quiescent endothelium upon the extracellular matrix (ECM) provided and (2) mononuclear leukocytes inside the ECM compartment. Different adjuvants or vaccine formulations are prepared using 100% autologous untouched or intact (i.e., not heat treated nor depleted of any components) heparinized plasma and applied to the NTCs. After 48 h of culture at 37° C. and at 5% $CO_2$ and gyroscopic movement, some of the initially extravasated leukocytes demonstrate autonomous migration out of the NTC ECM compartment (reverse transmigration) to become robust antigen-presenting cells (APCs) in response to adjuvants and vaccines. Supernatants from these cultures contain many inflammatory cytokines when vaccines and adjuvants are used. These NTC respond in very specific ways to different vaccines and adjuvants. These distinct immune-responsive profiles can be benchmarked to correlatives of in vivo immune-responsive profiles responding to the same stimulant in order to validate the vaccines and adjuvants for general immune-reactogenicity. For assessing vaccine efficacy, the capacity of the APCs generated by the different NTCs to stimulate lymphoproliferation and activation of autologous untouched naïve CD4+ T cells are tested. In other words, testing how good a vaccine will be in initiating a primary adaptive immune response in (i.e., vaccinating) a newborn and how many doses of vaccination with that vaccine will be needed to provide such an immune reaction.

Also disclosed herein is a method of activation of naïve untouched CD4 T cells by co-culturing NTC- or ATC-derived dendritic T cells with autologous naïve untouched CD4 T cells. By using non-xenologous materials in preparing the NTC- or ATC-derived dendritic T cells, and using autologous cells and heparinized plasma, the disclosed TCs and methods overcome the defects in currently used TCs. Some of the unique features of the use of TCs embodied herein as platforms to evaluate vaccines are that the TCs were made without the use of the following: heat inactivation, calcium and magnesium chelants, a certain percentage of M199 media, positively selected naïve CD4+ T cells, and/or allogenic lymphoproliferation. In some embodiments of the methods and TCs described, the TCs were made without the use of bovine collagen and/or fetal bovine serum.

By benchmarking with commercially available vaccines that have been shown to be safe and effective or less safe (e.g., too reactogenic) when used in humans at birth, infancy and adulthood, the reactogenicity induced by the TCs described herein can be validated by correlating with those reactogenic responses induced in vivo. The NTC is also a suitable in vitro test system to assess preclinical biosafety and efficacy of candidate vaccines for newborns. This initial application is to test for the intrinsic immune-reactogenicity of vaccines and adjuvants. The NTC can also be validated for the preclinical assessment of general reactogenicity of many other type of therapeutics. In one embodiment, the NTC and ATC allows for simultaneous preclinical assessment of same human individual as test and control, limiting the intrinsic variability observed by clinical trials where the test and the control are different individuals.

In one embodiment, the NTC employs cord blood mononuclear cells (CBMCs) to colonize the TCs. In one embodiment, the CBMCs are obtained by FICOLL separation. Other methods of obtaining CBMCs are known in the art. In other embodiments, the NTCs use whole blood or any other desired pre-selected blood elements thereof such as subpopulations of leukocytes (monocytes, lymphocytes, neutrophils), platelets, red blood cells, etc. In other embodiments, the NTC can be used to compare healthy versus diseased leukocytes; to test any type of drug intended for intravenous application; and to obtain meaningful biological information or immune reactogenicity ranging from rapid innate immune-reactogenicity to slow-developing antigen-specific adaptive immune responses.

The development of the ATCs and NTCs allow the comparisons of the immune cells from newborns and non-newborns. This comparison reveals that in comparison to their adult counterparts, autonomously developed neonatal MoDCs are distinct in migration, immunophenotype and functional responses to conventional vaccines. Moreover, the NTC reveals the distinct ability of Bacille Calmette-Guérin (BCG) vaccine to induce MoDC-dependent lymphocyte proliferation and differentiation. For example, while demonstrating strong autologous naïve CD4+ T lymphocyte proliferation by BCG that is normally given as a single dose vaccine, the NTC demonstrated substantially lower lymphocyte proliferation in response to MoDCs pulsed with other pediatric vaccines such as HBV and PCV that normally require 3 doses to confer protection in vivo. This demonstrates that a wholly human NTC can be used for assessing vaccine formulations directed at the very young human, e.g., a newborn.

There are advantages of the NTCS and ATCs over those currently known in the art. Firstly, no competitors are currently using a completely human tissue-engineered system. The wholly human TC increases efficiency of growing ECs such as HUVECs; the HUVECs form an about 100% confluent monolayer of cells in 24 hrs compared to 5-6 days observed in the currently known TCs. Even when using only human derived materials, there are no changes in monocyte migration and differentiation as compared with currently known TCs that use bovine derived materials, e.g., serum. By avoiding the use of exogenous antigens, one can ensure that rare antigen-responses are due to vaccine antigens and not from bovine remnants or any other non-vaccine xenologous elements present in the construct.

Secondly, newborns have a distinct immune system that impairs immune responses to conventional pediatric vaccines, rendering them susceptible to infection. As birth is a reliable point of healthcare contact worldwide, neonatal immunization could help reduce global infection. However, pediatric vaccine development has been largely ad hoc and empiric and has often disregarded immune ontogeny. Dendritic cells are key antigen-presenting cells crucial for vaccine responses whose function is age-dependent (for example, see review by Willems, F et al., Eur. J. Immunol. 2009). Human adult and animal studies do not reliably predict neonatal vaccine responses and therefore modeling age-specific human dendritic cell responses could help predict safety and efficacy of adjuvants and vaccines targeting the newborn. In vitro study of monocyte (Mo)-derived dendritic cell (MoDCs) typically employs culture in non-autologous media without endothelial cells, without extra-cellular matrix, and with the use of exogenous cytokines, but the relation of cells generated in this manner to those that exist in vivo is unknown. Studying the effect of vaccine formulations on autonomously generated dendritic cell cultured in a three-dimensional matrix containing autologous plasma, without addition of exogenous cytokines, may more accurately reflect neonatal immune responses that predict the in vivo efficacy of immunomodulatory agents, adjuvants, and vaccine formulations.

In some embodiments, the TCs and methods allow the evaluation of the efficacy of adjuvants, vaccines, or immune-response stimulating agent in an age-specific manner. For example, evaluating of the efficacy of adjuvants, vaccines, or immune-response stimulating agent in eliciting an immune protection in a particular age group. This is useful because certain age groups of humans are more susceptible to certain infectious pathogens.

The following is a non-limiting method of making and using age-specific TCs. Age-specific tissue constructs (TCs) are created as tri-dimensional micro-vascular interstitia in a 96-well format using human extracellular matrix components, primary human endothelial monolayers, and cryopreserved newborn cord blood mononuclear cells (CBMCs) or adult peripheral blood mononuclear cells (PBMCs) with their corresponding autologous plasma. TCs are colonized by heterogeneous CBMCs or PBMCs or, to generate pure cell populations of myeloid antigen-presenting cells also known as antigen-presenting dendritic cells (APCs) for subsequent study of interactions with autologous naïve CD4+ T lymphocytes, with purified CD33+ monocytes (CD33+ Mos). TCs are stimulated with adjuvants or vaccines including Bacille Calmette-Guérin (BCG), Hepatitis B vaccine (HBV), diphtheria tetanus and acellular pertussis vaccine (DTaP), a pentavalent vaccine containing whole cell pertussis (wP), or pneumococcal conjugate vaccine (PCV). TC-derived MoDCs are collected at 48 hours and immunophenotyped by polychromatic flow cytometry. Cytokines production can be measured using a 26-cytokine multiplex bead array of the conditioned media. Vaccine-pulsed APCs, autonomously generated by the tissue constructs colonized by CD33+ Mos, can be co-cultured with autologous naïve CD4+ T lymphocytes to assess lymphoproliferation and cytokine production.

Accordingly, embodiments disclosed herein provide an endothelial TC that is designed to better recapitulate the in vivo immune environment of a human immune system compared to other endothelial TCs known in the art. Embodiments of such a human endothelial TC can be custom-designed and used for in in vitro vaccine efficacy evaluation for an adult immune system, a non-neonatal immune system or a neonatal immune system. That is, if a vaccine or antigen to be evaluated is for use in the vaccination of a newborn, the human endothelial TC will be custom-designed to recapitulate the in vivo immune environment of a newborn. For example, using human newborn plasma or serum, human newborn MCs, human newborn CD33+ or CD14+ selected monocytes etc., and using cells and plasma or serum from the same individual, i.e. the cells, plasma or serum are autologous. On the other hand, if a vaccine or antigen to be evaluated is for use in the vaccination of adults, adolescents or children, the human endothelial TC will be custom-designed to recapitulate the in vivo immune environment of the respective age-specific group of non-neonate humans. For example, using age-matched human plasma or serum, human mononuclear cells, human CD33+ and/or CD14+ selected monocytes etc., and/or using cells and plasma or serum from the same individual, i.e. the cells, plasma or serum are autologous. In some embodiments, age-matched cells for adults are cells from adults from age groups of 21-30, 31-40, 41-50, 51-60, 61-70, and above 70. In one embodiment, age-matched cells for adolescents are cells from adolescents from ages 11-20. In some embodiments, age-matched cells for children are cells from children from ages 2-6 and 6-11.

In one embodiment, provided herein is a TC comprising a cushion of extracellular matrix, a monolayer of human ECs on the top of the cushion, and human MCs that have extravasated through the monolayer of human ECs have embedded in and colonized the cushion of extracellular matrix, and have differentiated to migratory dendritic cells. In some embodiments, the human ECs and/or human MCs are from newborns, adults, adolescents or children. In some embodiments, the human ECs and/or human MCs are from adults from age groups of 21-30, 31-40, 41-50, 51-60, 61-70, and above 70. In one embodiment, the human mononuclear cells are human CD33+ and/or CD14+ selected monocytes.

As used herein the term "comprising" or "comprises" when used in reference to the TCs and methods, indicate that the respective components thereof are essential to the TCs and methods respectively, yet the tissue constructs and methods are open to the inclusion of unspecified elements, whether essential or not.

As used herein the term "consisting essentially of" refers to those elements required for a given embodiment of the TCs and methods described. The term permits the presence of elements that do not materially affect the basic and novel or functional characteristic(s) of that embodiment of the TCs and methods.

In one embodiment, provided herein is a TC comprising a cushion of extracellular matrix comprising human collagen, a monolayer of human ECs on the top of the cushion, and human MCs that have extravasated through the monolayer of human ECs and have embedded within and colonized the cushion of extracellular matrix. In one embodiment, the TC comprises primarily of human components: human collagen, human endothelial cells cultured in human plasma, and human MCs or human CD33+ and/or CD14+ selected monocytes cultured in human serum albumin.

In one embodiment, provided herein is a human TC comprising a cushion of extracellular matrix comprising human collagen, a monolayer of human ECs on the top of the cushion, and human CD33+ and/or CD14+ selected monocytes that have extravasated through the monolayer of human ECs and are embedded within and colonized the cushion of extracellular matrix.

In one embodiment, provided herein is a human TC comprising a cushion of extracellular matrix comprising matured human collagen, a confluent monolayer of human ECs on the top of the cushion, and human MCs that have extravasated through the monolayer of human ECs and are embedded within and colonized the cushion of extracellular matrix.

In one embodiment, provided herein is a human TC comprising a cushion of extracellular matrix comprising matured human collagen, a confluent monolayer of human ECs on the top of the cushion, and human MCs that have extravasated through the monolayer of human ECs and are embedded within and colonized the cushion of extracellular matrix, wherein the human ECs and human MCs are obtained from a single donor or from age-matched donors. In one embodiment, the MCs develop and transform to migratory dendritic cells during the process of extravasating the endothelial monolayer and colonization of the extracellular matrix cushion. In one embodiment, the human ECs and human MCs can be from a newborn infant. In other embodiments, the human ECs and human mononuclear cells can be from an adult, adolescent or child. In these embodiments, the human ECs and human MCs of each tissue construct ideally should be at least be age-matched or representative age-group-matched. That is, for example, if the human ECs are from a child, then the human MCs should also be from a child; if the human ECs are from an adult of age 55, then the human MCs should ideally also be from an adult in the age group of 51-60.

In another embodiment of the TCs described, the human ECs and human MCs are not age-matched. For example, the human ECs are from an adult of age 25 and the human MCs are from an adult in the age group of 51-60.

In one embodiment of the TCs described, the human ECs and human MCs are autologous, meaning both the human ECs and human MCs are obtained from the same individual human.

In another embodiment of the TCs described, the human ECs and human MCs are not autologous, meaning both the human ECs and human MCs are not obtained from the same individual human.

In one embodiment, provided herein is a human TC comprising a cushion of extracellular matrix comprising matured human collagen, a confluent monolayer of human ECs on the top of the cushion, and human newborn MCs that have extravasated through the monolayer of human ECs and are embedded and colonized the cushion of extracellular matrix, wherein the human ECs and human newborn MCs are obtained from a single donor or from age-matched donors.

In one embodiment, provided herein is a human TC comprising a cushion of extracellular matrix comprising matured human collagen, a confluent monolayer of human ECs on the top of the cushion, and human MCs that have extravasated through the monolayer of human ECs and are embedded and colonized the cushion of extracellular matrix, wherein the human ECs and human MCs are obtained from a single donor or from age-matched donors, and wherein the human endothelial cells and human MCs are obtained from an umbilical cords.

In one embodiment, provided herein is a human TC comprising a cushion of extracellular matrix comprising matured human collagen, a confluent monolayer of human ECs on the top of the cushion, and human CD33+ and/or CD14+ selected monocytes that have extravasated through the monolayer of human ECs and are embedded and colonized the cushion of extracellular matrix, wherein the human ECs and human CD33+ and/or CD14+ selected are obtained from a single donor or from age-matched donors.

In one embodiment, provided herein is a human TC comprising a cushion of extracellular matrix comprising matured human collagen, a confluent monolayer of human ECs on the top of the cushion, and human newborn CD33+ and/or CD14+ selected monocytes that have extravasated through the monolayer of human ECs and are embedded and colonized the cushion of extracellular matrix, wherein the human ECs and human newborn CD33+ and/or CD14+ selected are obtained from a single donor or from age-matched donors.

In one embodiment, provided herein is a human TC comprising a cushion of extracellular matrix comprising matured human collagen, a confluent monolayer of human ECs on the top of the cushion, and human CD33+ and/or CD14+ selected monocytes that have extravasated through the monolayer of human ECs and are embedded and colonized the cushion of extracellular matrix, wherein the human ECs and human CD33+ selected are obtained from a single donor or from age-matched donors, and wherein the human ECs and human CD33+ and/or CD14+ selected are obtained from an umbilical cord.

In one embodiment, provided herein is a human TC comprising a cushion of extracellular matrix comprising matured human collagen, a confluent monolayer of human ECs on the top of the cushion, and human newborn CD33+ and/or CD14+ selected monocytes that have extravasated through the monolayer of human ECs and are embedded and colonized the cushion of extracellular matrix, wherein the human ECs and human newborn CD33+ and/or CD14+ selected are obtained from a single donor or from age-matched donors.

Also provided are methods of making and methods of using such endothelial TCs for in vitro vaccine, adjuvant, antigen or other immune-response stimulant efficacy evaluation, evaluating for projected stimulating an immune response in an adult immune system, as age-specific non-neonatal immune system or a neonatal immune system.

In one embodiment, provided herein is a method of preparing a TC, the method comprising providing a cushion of extracellular matrix, culturing human ECs on the cushion of extracellular matrix for a period of time sufficient for the cells to form a monolayer in the presence of human plasma, adding human mononuclear cells to the monolayer of human ECs, and culturing the human mononuclear cells in human serum albumin for a period of time sufficient for autonomous extravasation of the MCs through the monolayer of human ECs, colonization the cushion of extracellular matrix beneath the monolayer of human ECs, and with subsequent autonomous differentiation of MCs to migratory dendritic cells.

In one embodiment of any of the methods or TCs described, the cushion of extracellular matrix comprises collagen. In one embodiment, the collagen has been induced to congeal under alkaline condition. For example, in the presence of 0.1N NaOH described in the Example section.

In another embodiment of any of the methods or TCs described, the cushion of extracellular matrix further comprises fibronectin. In one embodiment, the fibronectin is human fibronectin.

In some embodiments of any of the methods or TCs described, the collagen used for the cushion of extracellular matrix can come from a variety of sources, non-limiting examples are human, cow and pig. Accordingly, in some embodiments of any of the methods or TCs described, the collagen is human collagen, bovine collagen or porcine collagen. Other recombinant collagens are also encompassed herein.

In one embodiment of any of the methods or TCs described, the collagen used for the cushion of extracellular matrix is a Type I collagen. For example, if the human collagen is used, the human collagen is human Type 1 collagen. In other embodiments of any of the methods or TCs described, the collagen used for the cushion of extracellular matrix is a Type II, a Type III, a Type IV, or a Type V collagen. In other embodiments of any of the methods or TCs described, the collagen used can be a mixture of several types of collagen, that is the mixture of the group of collagen selected from Type 1, Type II, Type III, Type IV, and Type V collagen.

Other extracellular matrix materials are also contemplated for use in making the cushion of extracellular matrix upon which the monolayer of endothelial cells are grown. Non-limiting examples of other extracellular matrix materials that can constitute the cushion of extracellular matrix are fibers such as elastin, laminin, proteoglycans, heparan sulfates, chondroitin sulfates, and keratan sulfates.

In one embodiment of any of the methods or TCs described, the collagen used for the cushion of extracellular matrix is glycosylated or glycated. In one embodiment, the collagen used for the cushion of extracellular matrix is not glycosylated or glycated prior to the formation of the matrix in the tissue construct. In order words, the collagen as a source of starting material for making the cushion of extracellular matrix was not glycosylated or glycated, for example, from human cadavers or from bovine. When collagen is glycosylated or glycated, it is considered to be "matured." Matured collagen provides a more suitable cell attachment surface for the endothelial cells which produce a confluent monolayer of cells within a short period of time, e.g., within two days.

In one embodiment of any of the methods or TCs described, the collagen used for the cushion of extracellular matrix is matured in the presence of glucose-6-phosphate. In one embodiment, when human collagen is used for the cushion of extracellular matrix, the human collagen matured in the presence of glucose-6-phosphate.

In one embodiment of any of the methods or TCs described, the glucose-6-phosphate is used at a concentration of about 20 mM to about 500 mM. In other embodiments, the glucose-6-phosphate is used at a concentration of about 50 mM to about 400 mM, about 50 mM to about 350 mM, about 50 mM to about 250 mM, about 100 mM to about 400 mM, about 100 mM to about 250 mM, about 150 mM to about 250 mM, about 150 mM to about 300 mM, or about 200 mM to about 250 mM, including all the concentration between about 20 mM to about 500 mM. In other embodiments, the glucose-6-phosphate is used at a concentration of about 20 mM, about 50 mM, about 70 mM, about 100 mM, about 120 mM, about 150 mM, about 170 mM, about 190 mM, about 210 mM, about 225 mM, about 250 mM, about 275 mM, about 290 mM, about 315 mM, about 325 mM, about 350 mM, about 370 mM, about 390 mM, about 400 mM, about 420 mM, about 440 mM, about 460 mM, about 485 mM, about 500 mM, including all the concentration between about 20 mM to about 500 mM.

In one embodiment of any of the methods or TCs described, the glucose-6-phosphate is pH-neutralized prior to use.

In one embodiment of any of the methods or TCs described, the collagen used for the cushion of extracellular matrix is matured in the presence of glucose-6-phosphate for at least 48 h. In some embodiments of any of the methods or TCs described, the collagen used for the cushion of extracellular matrix is matured in the presence of glucose-6-phosphate for 2, 2.5, 3, 3.5, 4, 4.5, or 5 days. Fractions of days between about 2 to about 5 days are also contemplated. In one embodiment of any of the methods or TCs described, when human collagen is used for the cushion of extracellular matrix, the human collagen is matured in the presence of glucose-6-phosphate for at least 48 h. In one embodiment of any of the methods or TCs described, the time period allowed for maturation in the presence of glucose-6-phosphate is at least 48 h and up to 5 days. In some embodiments, the time period is from 2-5 days, from 2-3 days, from 2-4 days, from 3-4 days, from 4-5 days, or from 3-5 days.

In one embodiment of any of the methods or TCs described, the human ECs are human primary ECs. In one embodiment, the human ECs are from a human adult, a human adolescent, a human child or from a human newborn. It is encompassed here that human ECs from a various sources can be used. Non-limiting examples are human pulmonary ECs from adult lung tissues, human endothelial cells from human umbilical cord after the birth of a baby, and human ECs from adult bone marrow. In one embodiment of any of the methods or TCs described, the human primary endothelial cells are obtained from human umbilical cord or vein. Commercial sources of human ECs such as human umbilical vein ECs (HUVECs) from MILLIPORE® and Cell Application Inc. are also encompassed herewith.

In one embodiment of any of the methods or TCs described, the human primary ECs are obtained from one single donor. For example, from a single human umbilical cord or vein, or bone marrow from a single adult, adolescent or child.

In one embodiment of any of the methods or TCs described, the human plasma has been previously been cryopreserved.

In one embodiment of any of the methods or TCs described, all the cells, serum and extracellular matrix materials for making the TCs have been previously been cryopreserved. For examples, the human ECs, human plasma, human MCs, human CD33+ and/or CD14+ monocytes, human serum albumin, and human umbilical cord blood.

In one embodiment of any of the methods or TCs described, the human ECs are cultured in the presence of human plasma. In one embodiment, the human plasma is human newborn plasma or non-newborn plasma such as plasma obtained from an adult, an adolescent or a child. In one embodiment, the human plasma is intact plasma, i.e., the plasma has not been depleted of any components naturally occurring in the plasma. For example, the plasma has not been depleted divalent ions, complement components or adenosine-generating purinergic enzymes, all important to immune activation and elicitation of an immune response. In one embodiment, the intact human plasma has not been depleted of platelets and/or divalent ions.

In one embodiment of any of the methods or TCs described, the human plasma is heat inactivated or not heat inactivated. In one embodiment, the human plasma is plasma pooled from more than one donor. In one embodiment, the human newborn plasma is obtained from human umbilical cord blood. The human newborn plasma can be from one human umbilical cord blood or from several human umbilical cord bloods, i.e., pooled from the cord blood from several newborns.

In one embodiment of any of the methods or TCs described, the human plasma is prepared with heparin that does not contain chelating agents, such that the divalent ions in the blood have not been chelated. Examples of divalent ions that are usually being chelated are magnesium and calcium. In one embodiment, the human plasma is not substantially depleted of endogenous divalent ions such as magnesium and calcium ions which are important to leukocyte activation and the production of immune responses. In one embodiment of any of the methods or TCs described, the human plasma is not substantially depleted of endogenous divalent ions magnesium and/or calcium ions.

As used herein, the term "substantially depleted" in reference to the divalent ions such as magnesium and calcium ions in human plasma and/or human serum means that the concentrations of the respective divalent ions therein are not less than about 75%, about 80%, about 85%, about 90%, about 95%, about 98%, about 99%, or about 100% of the concentrations naturally occurring in the human plasma and/or human serum from the particular donor or of the average concentrations naturally occurring in the human plasma and/or human serum from the population of donors. In another embodiment, "substantially depleted" refer to any other concentration lower than those concentrations of ions that allow spontaneous coagulation of plasma.

As used herein, the term "endogenous" in reference to the divalent ions such as magnesium and calcium ions refers to the naturally occurring amount of divalent ions in human plasma and/or human serum that is withdrawn from a donor.

In one embodiment of any of the methods or TCs described, the human ECs are not cultured in the presence of fetal bovine serum, fetal bovine calf serum or horse serum. In other words, the human ECs are not cultured in the presence of any other xenologous (i.e., non-human) serum or plasma. In another embodiment, the human ECs are not cultured in the presence of non-human derived serum or plasma.

In one embodiment of any of the methods or TCs described, the human primary ECs are cultured in the presence of at least 40% of human plasma, i.e. the cell culture media used in culturing human ECs on the cushion of extracellular matrix comprises at least 40% of human plasma. In another embodiment, the cell culture media comprises at least 50% of human plasma. In one embodiment, the cell culture media comprises about 50% of human plasma. In other embodiments, about 55%, about 60%, about 65%, about 70%, about 75%, about 80%, about 85%, about 90%, about 95%, about 100% of human plasma is used to culture the human ECs, including all the possible percentages between 50% and 100%. In other embodiments, the cell culture media comprises about 40%-100% of human plasma. In other embodiments, the cell culture media comprises about 40%-90%, about 40%-80%, about 40%-70%, about 40%-60% about 40%-50%, about 45%-95%, about 45%-85%, about 45%-75%, about 45%-65%, about 45%-

55%, about 50%-90%, about 50%-80%, about 50%-70%, about 50%-60%, about 55%-95%, about 55%-85%, about 55%-75%, about 55%-65%, about 55%-60% and all the possible ranges between about 40%-100% of human plasma.

In one embodiment of any of the methods or TCs described, the ECs are cultured to a confluent monolayer on the cushion of extracellular matrix. In another embodiment, the human primary ECs are cultured to a confluent monolayer on the cushion of extracellular matrix.

In one embodiment of any of the methods or TCs described, the confluent monolayer of ECs is at least 90% confluent. In other embodiments, the confluent monolayer is at least 91% confluent, at least 92% confluent, at least 93% confluent, at least 94% confluent, at least 95% confluent, at least 96% confluent, at least 97% confluent, at least 98% confluent, at least 99% confluent, or at least 100% confluent.

In another embodiment of any of the methods or TCs described, the confluent monolayer of ECs is about 92%-100% confluent. In other embodiments, the confluent monolayer is about 94%-about 100% confluent, about 96%-about 100% confluent, about 98%-about 100% confluent, about 92%-about 98% confluent, about 92%-about 96% confluent, about 92%-about 94% confluent, about 91%-about 100% confluent, about 91%-about 99% confluent, about 91%-about 97% confluent, about 91%-about 95% confluent, about 91%-about 93% confluent, about 93%-about 99% confluent, about 93%-about 97% confluent, about 93%-about 95% confluent, about 93%-about 94% confluent, about 95%-about 100% confluent, about 95%-about 98% confluent, about 95%-about 99% confluent, about 95%-about 97% confluent, about 95%-about 96% confluent, and all the possible ranges between about 90%-about 100%.

In one embodiment of any of the methods or TCs described, the period of time sufficient for the ECs to form a monolayer in the presence of human plasma is at least 24 h. In other embodiments, the period of time sufficient for the ECs to form a monolayer in the presence of human plasma is at least 30 h, at least 36 h, at least 42 h, at least 48 h, at least 54 h, at least 60 h, at least 66 h, at least 72 h, and at least all the possible integer hours between about 24 h-about 72 h. In other embodiments, the period of time sufficient for the ECs to form a monolayer in the presence of human plasma is about 30 h, about 36 h, about 42 h, about 48 h, about 54 h, about 60 h, about 66 h, about 72 h, and all the possible integer hours between about 24 h to about 72 h.

In one embodiment of any of the methods or TCs described, the period of time sufficient for the ECs to form a monolayer is about 24 h to about 5 days. In other embodiments, the period of time to obtain a monolayer is about 24 h to about 2 days, about 24 h to about 1.5 days, about 30 h to about 3 days, about 30 h to about 2 days, about 30 h to about 1.5 days, about 36 h to about 3 days, about 36 h to about 2 days, about 36 h to about 2.5 days, about 1.5 to about 3 days, about 1.5 to about 2 days, about 2 to about 5 days, and all the possible integer hours between about 24 h to about 5 days.

In one embodiment of any of the methods or TCs described, the human MCs that undergo autonomous extravasation of the monolayer of human ECs to colonize the cushion of extracellular matrix beneath the monolayer of human ECs are human newborn MCs. In one embodiment, the human newborn MCs are obtained from human umbilical cord blood. In one embodiment, the human newborn MCs are from a single donor, e.g., human umbilical cord blood from a single newborn. In another embodiment, the human newborn MCs are pooled from more than one donor, e.g., human umbilical cord blood or placental blood from several newborns. For example, discarded human umbilical cords from maternity wards can be collected, and the cord blood from these discarded umbilical cords can be harvested and pooled for the isolation of MCs. In one embodiment, the human newborn MCs are pooled from more than one donor, the donors are genetically identical or genetically related. For example, the donors are identical twins, triplets or quadruplets; these donors would be genetically identical. For example, the donors are fraternal twins, triplets, quadruplets, quintuplets, sextuplets, septuplets, octuplets, nonuplets or decaplets etc. These donors would be genetically related, but are not genetically identical. For example, the donors are siblings born at different time and year. These donors would be genetically related, but are not genetically identical. The human newborn MCs are harvested from a first sibling and cryopreserved. Then when a second sibling is born, its newborn MCs are harvested. The newborn MCs from the second child can subsequently be are cryopreserved. When needed to seed the cushion of extracellular matrix, the newborn MCs from the first and second child can be thawed, pooled and used accordingly.

In one embodiment of any of the methods or TCs described, the human mononuclear cells (MC) that undergo autonomous extravasation of the monolayer of human ECs to colonize the cushion of extracellular matrix beneath the monolayer of human ECs are derived from an adult, a newborn, an infant, an adolescent or a child. In one embodiment, the human MCs are obtained from circulating peripheral blood. In one embodiment, the human MCs are from a single donor, e.g., circulating peripheral blood from a single adult, newborn, infant, adolescent or child. In another embodiment, the human MCs are pooled from more than one donor, e.g., circulating peripheral blood collected from several adults, adolescents or children. In one embodiment, the pooled human MCs are pooled from one representative class of donors, meaning the pooled human MCs are from only adults, from only adolescents or only children. That is, the pooled human MCs do not contain human MCs pooled from adults and adolescents, pooled from adults, adolescents or children, pooled from adults and children, or pooled from adolescents or children. In some embodiments, when the pooled human MCs are pooled from one representative age-group of donors, i.e., the donors are age-matched.

Human MCs can be isolated from circulating peripheral blood, bone marrow or umbilical cord blood. Methods of preparing MCs are known in the art, for example, from a sample of blood, the MC fraction of the blood can be obtained by PERCOLL or FICOL density gradient centrifugation as described in the example section.

In one embodiment of any of the methods or TCs described, the human MCs are derived from one donor. In another embodiment, the human MCs are not pooled from more than one donor.

In one embodiment of any of the methods or TCs described, the human MCs are cells previously cryopreserved.

In one embodiment of any of the methods or TCs described, the human MCs are human CD33+ monocytes. In another embodiment, the human MCs are human CD14+ monocytes. In yet another embodiment, the human MCs are human CD33+ and CD14+ monocytes. In other words, the human MCs are selected positively for CD33 and/or CD14 cell surface markers. Human CD33+ and/or CD14+ monocytes can come from several sources; non-limiting examples sources of CD33+ and/or CD14+ monocytes are human umbilical cord blood, circulating peripheral blood and bone marrow. In some embodiments, human CD33+ and/or CD14+ monocytes can be obtained from the circulating peripheral blood or bone marrow of a human adult, a human adolescent or a human child. In another embodiment, the human CD 33+ and/or CD14+ monocytes can be obtained from human umbilical cord blood of a newborn, therefore it is termed human newborn CD33+ monocytes, human newborn CD33+, CD14+ monocytes or human newborn CD14+ monocytes. Several techniques are known for rapid isolation of CD33+ and/or CD14+ cells such as, but not limited to, leucopheresis, density gradient fractionation, immunoselection, differential adhesion separation, and the like. As a non-limiting example, MC can be obtained by density gradient centrifugation and labeled with magnetic bead-conjugated anti-CD33 or anti-CD14+ antibody and passed through one or more magnetic columns to yield positively selected CD33+ or CD14+ cells respectively. Additionally or alternatively, MCs can be labeled with a fluorescent antibody to CD33 or CD14 and sorted by a fluorescence activated cell sorter (FACS) to obtain CD33+ or CD14+ cells respectively. Yields and purity of the obtained CD33+ cells or CD14+ cells can vary, depending on the source and the methods used to purifying the cells. Purity obtained after one passage of labeled cells through a magnetic column can be, for example, 75%-95% and, after subsequent FACS, the purity could be increased to 95%-100%.

In one embodiment of any of the methods or TCs described, the human CD33+ monocytes are purified positive isolated CD33+ monocytes.

In one embodiment of any of the methods or TCs described, the human newborn MCs are CD33+ selected monocytes.

In one embodiment of any of the methods or TCs described, the human CD33+ monocytes still preserve some monocyte heterogeneity (e.g. CD14-dim/negative CD16+ monocytes).

In one embodiment of any of the methods or TCs described, the human newborn CD33+ monocytes are allowed to extravasate in the TC.

In one embodiment of any of the methods or TCs described, the extravasated human newborn CD33+ autonomously differentiation into mature reverse transmigrated dendritic cells (DCs) in the TC.

In one embodiment of any of the methods or TCs described, the dendritic cells are at least HLA-DR+ and/or CD86high and/or CCR7+.

In one embodiment of any of the methods or TCs described, the human CD33+ and/or CD14+ monocytes are cells that have been previously cryopreserved. All cryopreserved cells described herein can be thawed according to standard methods known in the art and use in the methods described herein.

In one embodiment of any of the methods or TCs described, the human CD33+ and/or CD14+ monocytes are newborn CD33+ and/or CD14+ monocytes, i.e., obtained from a newborn. In one embodiment, the human newborn CD33+ and/or CD14+ monocytes are obtained from one or more newborns, and then pooled together. In one embodiment, the human newborn CD33+ monocytes are obtained from the human umbilical cord blood of one or more newborns and then pooled together.

In another embodiment of any of the methods or TCs described, the human CD 33+ and/or CD14+ monocytes are obtained from a human non-newborn. In some embodiments, the human CD33+ and/or CD14+ monocytes are obtained from an adult, an adolescent or a child. In some embodiments, the human CD33+ monocytes are obtained and pooled from one or more adult, one or more adolescent or one or more children.

In one embodiment of any of the methods or TCs described, the human CD33+ and/or CD14+ monocytes or CD33 and/or CD14-selected monocytes are derived from one donor, i.e., adult-, adolescent-, child- or newborn-derived human CD33+ and/or CD14+ monocytes are obtained from one single donor. In another embodiment, the adult-, adolescent-, child- or newborn-derived human CD33+ and/or CD14+ monocytes or CD33 and/or CD14-selected monocytes are not pooled from more than one donor.

In another embodiment of any of the methods or TCs described, the adult-, adolescent-, child- or newborn-derived human CD33+ and/or CD14+ monocytes are pooled from more than one donor. In one embodiment, the pooled human CD33+ and/or CD14+ monocytes are pooled from one representative age-group or class of donors, meaning the pooled human CD33+ and/or CD14+ monocytes are from only adults, from only adolescents or only children. That is, the pooled human CD33+ and/or CD14+ monocytes is not a mixture of human CD33+ and/or CD14+ monocytes pooled from adults and adolescents, pooled from adults, adolescents or children, pooled from adults and children, or pooled from adolescents or children. In some embodiments, when the pooled human CD33+ and/or CD14+ monocytes are pooled from one representative class or age-group of donors, the donors are age-matched. For example, if the pooled human CD33+ and/or CD14+ monocytes are pooled from only adults, the monocytes are from adults of only the 21-30 age group adults, only the 31-40 age group adults, only the 41-50 age group adults, only the 51-60 age group adults, only the 61-70 age group adults, or only the above 70 age group adults.

In one embodiment of any of the methods or TCs described, the human MCs or CD33+ and/or CD14+ monocytes are cultured in the presence of human serum albumin. In one embodiment, the human serum albumin is clinical grade human serum albumin. In one embodiment, the human serum albumin is not heat inactivated. In one embodiment, the human serum albumin is pyrogen-free. In one embodiment, the human serum albumin has previously been cryopreserved or frozen.

In one embodiment of any of the methods or TCs described, the human serum albumin is prepared with heparin that does not contain chelating agents, such that the divalent ions in the blood have not been chelated. Examples of divalent ions that are usually being chelated are magnesium and calcium. In one embodiment, the human serum albumin is not substantially depleted of endogenous divalent ions such as magnesium and calcium ions. In one embodiment, the serum albumin is not substantially depleted of endogenous divalent ions magnesium and/or calcium ions.

In one embodiment of any of the methods or TCs described, the human MCs or CD33+ and/or CD14+ monocytes are cultured in the presence of at least 0.05% human serum albumin. In one embodiment, the human MCs or CD33+ and/or CD14+ monocytes are cultured in the presence of about 0.05% to about 10% human serum albumin. In some embodiments, the human MCs or CD33+ and/or CD14+ monocytes are cultured in the presence of about 0.1% to about 10%, about 0.1% to about 5%, about 0.1% to about 1%, about 0.1% to about 0.5%, about 0.1% to about 0.6%, about 0.1% to about 0.7%, about 0.1% to about 0.8%, about 0.1% to about 0.9%, about 0.2% to about 1%, about 0.4% to about 1%, about 0.6% to about 1%, about 0.8% to about 1%, about 0.1% to about 0.4%, about 0.1% to about 0.3%, about 0.1% to about 0.2%, about 0.5% to about 1%, about 0.5% to about 2%, about 0.05% to about 0.4%, about 0.05% to about 0.3%, about 0.05% to about 0.2%, about 0.05% to about 1%, about 0.05% to about 2%, including all possible range of percent between about 0.05% to about 10% of human serum albumin. In one embodiment, the human MCs or CD33+ and/or CD14+ monocytes are cultured in the presence of at least 0.1% human serum albumin. In other embodiments, the human MCs or CD33+ and/or CD14+ monocytes are cultured in the presence of about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, or about 0.15% human serum albumin.

In one embodiment of any of the methods or TCs described, the human MCs or CD33+ and/or CD14+ monocytes are not cultured in the presence of exogenously added cytokines or immune response stimulating agents. Non-limiting examples of exogenous cytokines or immune response stimulating agent are granulocyte-macrophage colony-stimulating factor (GM-CSF) and interleukin-4 (IL-4). In one embodiment, the human MCs or CD33+ and/or CD14+ monocytes are not cultured in the presence of exogenously added GM-CSF. In one embodiment, the human MCs or CD33+ and/or CD14+ monocytes are not cultured in the presence of exogenously added IL-4. In one embodiment, the human MCs or CD33+ and/or CD14+ monocytes are not cultured in the presence of exogenously added GM-CSF and IL-4.

As used herein, the term "exogenously added" when used in reference to cytokines or immune response stimulating agents means specifically adding the cytokines or agents from an external source into the culture media thereby artificially increasing the concentration of such cytokines or agent over that if no specific addition was made. In one embodiment, "exogenously added" does not encompass the cytokines or immune response stimulating agents naturally found in the serum or plasma that is added to the culture media and constitute the culture media.

In one embodiment of any of the methods or TCs described, the human MCs or CD33+ and/or CD14+ monocytes are allowed to autonomous extravasation of the monolayer of ECs to colonize the cushion of extracellular matrix in the absence of serum.

In one embodiment of any of the methods or TCs described, the period of time sufficient to allow the human MCs or CD33+ and/or CD14+ monocytes to autonomous extravasation of the monolayer of ECs and to colonize the cushion of extracellular matrix is at least 0.5 h. In one embodiment, the period of time is about 0.5 h, about 0.6 h, about 0.7 h, about 0.8 h, about 0.9 h, about 1.0 h, about 1.1 h, about 1.2 h, about 1.3 h, about 1.4 h, about 1.5 h, about 1.6 h, about 1.7 h, about 1.8 h, about 1.9 h, or about 2.0 h.

In one embodiment of any of the methods or TCs described, the period of time sufficient to allow the human MCs or CD33+ and/or CD14+ monocytes to autonomous extravasation of the monolayer of ECs and to colonize the cushion of extracellular matrix is about 0.5 h to about 4 h, about 0.5 h to about 3 h, about 0.5 h to about 2 h, about 0.5 h to about 1 h, about 1 h to about 4 h, about 1 h to about 3 h, about 1 h to about 2 h, about 1.5 h to about 4 h, about 1.5 h to about 3 h, about 1.5 h to about 2 h, about 2 h to about 4 h, or about 2 h to about 3 h. Fractions of an hour are also encompassed here.

In one embodiment of any of the methods or TCs described, the period of time sufficient to allow the human MCs or CD33+ and/or CD14+ monocytes to autonomous extravasation of the monolayer of ECs and to colonize the cushion of extracellular matrix is about 1.5 h to about 2 h. In one embodiment, the period of time sufficient to allow the human MCs or CD 33+ and/or CD14+ monocytes to autonomous extravasation of the monolayer of ECs and to colonize the cushion of extracellular matrix is no more than about 2 h. Not wishing to be bound by theory, it is believed that during this period of autonomous extravasation or shortly thereafter, the human MCs or CD 33+ and/or CD14+ monocytes transform or differentiate into migratory dendritic cells. At the end of this period of autonomous extravasation, the cushion of extracellular matrix is colonized by a population of human migratory dendritic cells. Cells that have extravasated into and those retained inside the cushions after 48 hours of culture show very low expression of cell markers consistent with dendritic cell development. After extravasation into the extracellular matrix, these cells autonomously can reverse-transmigrated back across the endothelial monolayer into the luminal compartment of the tissue construct as dendritic cells. Reverse transmigration occurs even without stimulation, yielding largely immature migratory dendritic cells. However, both the extent of reverse transmigration and the immunophenotype (e.g., degree of maturity and bioactivity) of the reverse transmigrated dendritic cells are markedly modulated by exposure to stimuli such as immunomodulatory agents, adjuvants, and vaccine formulations. Accordingly, these cells can reverse-transmigrated in the presence of an immune response stimulating agent or when exposed to an immune response stimulating agent.

In one embodiment of any of the methods or TCs described, the TC described is prepared in a tissue culture well. In another embodiment, the tissue construct in located at the bottom of a tissue culture well.

In some embodiments of any of the methods or TCs described, multiple TCs are made in multiple tissue culture wells which make up a 6-well, 12-well, 24-well, 48-well, or 96-well tissue culture plate.

In one embodiment of any of the methods or TCs described, the extracellular matrix cushion of the TC is prepared in advance and stored prior to the subsequent steps of culturing the monolayer of endothelial cells and autonomous extravasation of human MCs or CD 33+ and/or CD14+ monocytes. In one embodiment, the extracellular matrix cushion described can be stored at about 4° C. for a period of time before further use. In one embodiment, the storage time can be up to about a week. In some embodiments, the TC described is used within about a week after preparation.

Also provided are methods of using the endothelial TCs described for in vitro testing of vaccine efficacy in stimulating an adult immune system or a neonatal immune system. The method comprises using the endothelial tissue constructs described for preparing a population of human dendritic cells in vitro. In one embodiment, the population of human dendritic cells thus produced comprises dendritic cells that are exposed to a specific antigen, vaccine or immune response stimulating agent. In one embodiment, the population of human dendritic cells thus produced comprises dendritic cells that are challenged by a specific antigen, vaccine or immune response stimulating agent. In one embodiment, the population of human dendritic cells thus produced comprises dendritic cells that are matured in response to a specific antigen, vaccine or immune response stimulating agent. Alternatively, the dendritic cells are exposed, challenged and/or matured in response to a group or collection of specific antigens, vaccines or immune response stimulating agents. In other embodiments, an adjuvant is being tested in conjunction with the specific antigen, vaccine or immune response stimulating agent tested.

As used herein, the term "antigen" is any substance that induces an immune response in the body, for example but not limited to the production of antibodies. In another embodiment, an "antigen" is any substance that is suspected of inducing an immune response in the body. In one embodiment, the antigen can be a foreign substance, i.e., a substance that is not naturally found in the body of a subject. For example, bacteria, viruses, fungi, parasites, and substances that appear foreign and harmful to the body. In another embodiment, the antigen can be a non-foreign substance, i.e., a substance that is naturally found in the body of the subject. Non-living substances such as toxins, chemicals, drugs, and foreign particles (such as a splinter) can also be antigens. The immune system recognizes and destroys substances that contain these antigens.

The immune response induced in the body include the adaptive immune response which comprises (1) antigen presentation by certain immune cells, (2) the production of antibodies that specifically recognize and bind the antigen, (3) production and proliferation of antibody-producing cells, and (4) the production of antibody-producing memory cells which give rise to immunological memory. Alternatively, the immune response induced in the body include the innate immune response which comprises recruitment of immune cells to sites of infection, activation of the complement cascade, and the identification and removal of foreign substances present in organs, tissues, the blood and lymph, by specialized white blood cells.

As used herein, the term "vaccine" is a substance that is used to stimulate the production a memory response such as memory T cells and/or B cells resulting in cell mediated and antibody-mediated long-term protection of a subject, thereby providing immunity against one or several diseases. In some embodiments, a vaccine is prepared from the causative agent of a disease, its products, or a synthetic substitute, treated to act as an antigen without inducing the disease. For example, a vaccine can consist of a suspension of weakened or dead pathogenic microbial or cancer cells injected in order to stimulate the production of antibodies in the subject.

As used herein, the term "immune response stimulating agent" refers to any agent that induces an immune response in a subject. In one embodiment, the agent induces a non-specific innate immune response. In another embodiment, the agent induces a specific adaptive immune response that results in either one or more of the following phenomena: phagocytosis of antigen by immune cells such as dendritic cells, antigen presentation by immune cells as dendritic cells, the production of antibodies that specifically recognize and bind the antigen, production and proliferation of antibody-producing cells, and the production of antibody-producing memory cells which give rise to immunological memory.

An "immunomodulator" as used herein is an agent that causes or facilitates a qualitative or quantitative change, alteration, or modification in an immune system, for example, eliciting an immune response. In some embodiment, the immune response can encompass production of cytokines, chemokines, antibodies and increase cell proliferation.

The term "agent" refers to any entity that is normally not present or not present at the levels being administered to a cell, tissue or subject. Agent can be selected from a group comprising: chemicals; small molecules; nucleic acid sequences; nucleic acid analogues; proteins; peptides; aptamers; nanoparticles; antibodies; or functional fragments thereof. In some embodiments, the agent is any chemical, entity or moiety, including without limitation synthetic and naturally-occurring non-proteinaceous entities. In certain embodiments, the agent is a small molecule having a chemical moiety.

In one embodiment, by "stimulating an adult immune system" or "stimulating a neonatal immune system" by antigen, vaccine or immune response stimulating agent means the induction of an immune response in a subject, the subject being an adult, an adolescent, a child or a newborn. In another embodiment, "stimulating an adult immune system" or "stimulating a neonatal immune system" can mean promoting or supporting the induction of an immune response in a subject.

In one embodiment, the induction of an immune response is not in a subject, but rather the induction is ex vivo. For example, the immune response is induced in a cell derived from the subject and the immune response is induced is ex vivo, for example, in a tissue culture conditions. In one embodiment, the cell, derived from the subject and which responses to an antigen or a vaccine, is a cell that is part of the immune system of the subject. In one embodiment, the cell can be an immature cell or a mature cell that is part of the immune system of the subject. Non-limiting cells that is part of the immune system of the subject include, for example, immature dendritic cell and mature dendritic cell, macrophages, B-lymphocytes, T-lymphocytes, and T-helper cells. The immune response induced can be a non-specific innate immune response or a specific adaptive immune response. In some embodiments, the immune response stimulated encompasses either one or more of the following phenomena: phagocytosis of antigen by immune cells such as dendritic cells, antigen presentation by immune cells as dendritic cells, the production of antibodies that specifically recognize and bind the antigen, production and proliferation of antibody-producing cells, and the production of memory T lymphocytes and/or antibody-producing memory B cells which give rise to immunological memory.

Accordingly, provided herein is a method of preparing a population of human dendritic cells in vitro, the method comprising introducing an adjuvant/antigen/vaccine/immune response stimulating agent in the presence of human plasma to a TC described herein, incubating the TC with the adjuvant/antigen/vaccine/immune response stimulating agent in the presence of human plasma for a period of time sufficient to allow reverse-transmigrated of the human MCs from the monolayer of ECs, and collecting the reverse-transmigrated MCs which have developed into matured dendritic cells in the presence of the antigen/vaccine/immune response stimulating agent.

Accordingly, provided herein is a method of preparing a population of human dendritic cells in vitro, the method comprising first preparing or providing a TC comprising extravasated human MCs in a cushion of extracellular matrix, then introducing an antigen/vaccine/immune response stimulating agent in the presence of human plasma to the TC, incubating the TC with the antigen/vaccine/immune response stimulating agent in the presence of human plasma for a period of time sufficient to allow reverse-transmigrated of the human MCs from the monolayer of ECs, and collecting the reverse-transmigrated MCs that have developed into antigen-presenting dendritic cells in the presence of the antigen/vaccine/immune response stimulating agent. The TC is prepared by a method comprising culturing human ECs on a cushion of extracellular matrix for a period of time sufficient to obtain a monolayer in the presence of human plasma, introducing human MCs to the monolayer of human ECs, culturing the human MCs for a period of time sufficient to allow the human MCs to autonomous extravasation of the monolayer of ECs and colonize the cushion of extracellular matrix, and removing non-extravasated MCs after the period of time in the immediate preceding step.

In one embodiment, provided herein is a method of preparing a population of human dendritic cells in vitro, the method comprising: introducing an antigen/vaccine/immune response stimulating agent in the presence of human plasma to a TC, wherein the TC was previously prepared by: providing a cushion of extracellular matrix comprising human collagen, incubating the extracellular matrix in the presence of glucose-6-phosphate for a sufficient period of time to allow the collagen to mature, seeding the cushion of extracellular matrix with human endothelial cells, culturing the human ECs to a confluent monolayer in the presence of human plasma, introducing human MCs to the confluent monolayer of human ECs in the presence of non-heat inactivated human serum albumin, incubating for a period of time sufficient to allow the MCs to undergo autonomous extravasation of the confluent monolayer of human ECs, and removing the non-extravasated human MCs; incubating the TC with the adjuvant/antigen/vaccine/immune response stimulating agent in the presence of human plasma for a period of time sufficient for the extravasated human MCs to reverse-transmigrated the confluent monolayer of human ECs; and collecting the reverse-transmigrated MCS which have developed into matured dendritic cells in the presence of the antigen/vaccine/immune response stimulating agent.

Not wishing to be bound by theory, the human MCs or CD33+ and/or CD14+ monocytes are progenitor cells of the immune system. These progenitor cells initially transform into migratory dendritic cells in the presence of endothelial cells. The migratory dendritic cells are characterized by high endocytic activity and low T-cell activation potential. Migratory dendritic cells constantly sample the surrounding environment for pathogens such as viruses and bacteria. This is done through pattern recognition receptors (PRRs) such as the Toll-like receptors (TLRs). TLRs recognize specific chemical signatures found on subsets of pathogens. Migratory dendritic cells may also phagocytize small quantities of membrane from live own cells, in a process called nibbling. Once they have come into contact with a presentable antigen, they become activated into mature dendritic cells and begin to migrate to the lymph node. Migratory dendritic cells phagocytose pathogens and degrade their proteins into small pieces and upon maturation present those fragments at their cell surface using MHC molecules, becoming an antigen-presenting dendritic cell. Simultaneously, they up-regulate cell-surface receptors that act as co-receptors in T-cell activation such as CD80 (B7.1), CD86 (B7.2), and CD40 greatly enhance their ability to activate T-cells. They also up-regulate CCR7, a chemotactic receptor that induces the dendritic cell to travel through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen specific co-stimulatory signals.

In some embodiments of any of the methods described, the human plasma used with the adjuvant/antigen/vaccine/immune response stimulating agent is human plasma obtained from a newborn, an adult, an adolescent or a child. In other embodiments, the human plasma used with the adjuvant/antigen/vaccine/immune response stimulating agent is human platelet poor plasma derived from a newborn, an adult, an adolescent or a child. Accordingly, in one embodiment, the human plasma used with the antigen/vaccine/immune response stimulating agent is human newborn platelet poor plasma. In another embodiment, the human plasma used with the antigen/vaccine/immune response stimulating agent is human adult platelet poor plasma. In other embodiments, the human plasma used with the adjuvant/antigen/vaccine/immune response stimulating agent is human adolescent or child platelet poor plasma.

Platelet-Poor Plasma (PPP) is blood plasma with very low number of platelets ($<10 \times 10^3/\mu L$). A variety of methods can be used to prepare PPP. For example, PPP is produced by separating plasma from red blood cells using a high spin to pellet platelets with the red cells. Separation of platelets is desirable because they provide an additional source of foreign antigens. Devices can be used to achieve separation, e.g. the Gravitation Platelet System GPS® III System.

In one embodiment of any of the methods described, the human PPP used with the antigen/vaccine/immune response stimulating agent is not heat inactivated.

In one embodiment of any of the methods described, the human PPP used with the antigen/vaccine/immune response stimulating agent is at least 50%, i.e. the cell culture media comprising the adjuvant/antigen/vaccine/immune response stimulating agent comprises at least 50% of human PPP. In one embodiment, the human PPP used with the antigen/vaccine/immune response stimulating agent is at about 50%. In one embodiment, the human PPP used with the adjuvant/antigen/vaccine/immune response stimulating agent is at about 100%. In other embodiments, the human PPP used with the antigen/vaccine/immune response stimulating agent is at about 55%, about 60%, about 65%, about 70%, about 75%, about 80%, about 85%, about 87%, about 90%, about 92%, about 95%, about 97%, including all the possible percentages between 50% and 100%. In one embodiment, the human PPP used with the adjuvant/antigen/vaccine/immune response stimulating agent is used at about 50%-100%. In other embodiments, the human PPP used with the antigen/vaccine/immune response stimulating agent is at about 50%-90%, about 50%-80%, about 50%-70%, about 50%-60%, about 55%-95%, about 55%-85%, about 55%-75%, about 55%-65%, about 55%-60%, about 60%-100%, about 60%-99%, about 60%-95%, about 60%-90%, about 60%-80%, about 60%-70%, about 70%-80%, about 70%-85%, about 70%-90%, about 70%-95%, about 70%-99%, about 70%-100%, about 80%-90%, about 80%-92%, about 80%-95%, about 80%-97%, about 80%-99%, about 80%-100%, about 85%-90%, about 85%-92%, about 85%-95%, about 85%-97%, about 85%-99%, about 85%-100%, about 90%-92%, about 90%-95%, about 90%-97%, about 90%-99%, about 90%-100%, about 92%-95%, about 92%-95%, about 92%-97%, about 92%-99%, about 92%-100%, about 95%-97%, about 95%-100%, about 97%-100% and all the possible ranges between about 50%-100% of human PPP. In one embodiment, the PPP used with the adjuvant/antigen/vaccine/immune response stimulating agent is used at 100%.

In one embodiment of any of the methods described, the human PPP used with the adjuvant/antigen/vaccine/immune response stimulating agent is prepared with heparin that does not contain chelating agents, such that the divalent ions in the blood have not been chelated. Examples of divalent ions that are usually being chelated are magnesium and calcium. In one embodiment, the human PPP used with the adjuvant/antigen/vaccine/immune response stimulating agent is not substantially depleted of endogenous divalent ions such as magnesium and calcium ions. In one embodiment, the human PPP used with the adjuvant/antigen/vaccine/immune response stimulating agent is not substantially depleted of endogenous divalent ions magnesium and/or calcium ions.

In one embodiment of any of the methods or TCs described herein, the human plasma, human platelet-poor plasma or human serum albumin is heat inactivated.

In another embodiment of any of the methods or TCs described herein, the human plasma, human PPP or human serum albumin is not heat inactivated.

In one embodiment of any of the methods or TCs described herein, the human plasma, human PPP or human serum albumin does not contain a chelating agent.

In one embodiment of any of the methods or TCs described herein, the human newborn plasma, human newborn PPP or human newborn serum albumin does not contain a chelating agent.

In one embodiment of any of the methods or TCs described herein, the human plasma, human platelet-poor plasma or human serum albumin is prepared with heparin.

In one embodiment of any of the methods or TCs described herein, the human newborn plasma, human newborn PPP or human newborn serum albumin is prepared with heparin.

In one embodiment of any of the methods or TCs described herein, the human plasma, human PPP or human serum albumin is prepared in the absence of a chelating agent.

In one embodiment of any of the methods or TCs described herein, the human newborn plasma, human newborn PPP or human serum albumin is prepared in the absence of a chelating agent.

In one embodiment of any of the methods or TCs described herein, the chelating agent chelates divalent ions from the plasma or serum, such as magnesium and/or calcium ions.

In one embodiment of any of the methods described, the period of time sufficient to allow reverse-transmigrated of the migratory dendritic cells from the cushion of extracellular matrix and the monolayer of ECs is at least about 24 h. In other embodiments, the period of time sufficient for reverse-transmigrated of the migratory dendritic cells is at least about 26 h, at least about 28 h, at least about 30 h, at least about 32 h, at least about 34 h, at least about 36 h, at least about 38 h, at least about 40 h, at least about 42 h, at least about 44 h, at least about 46 h, at least about 48 h, including at least about all the possible integer hours between about 24 h-about 48 h.

In one embodiment of any of the methods described, the period of time sufficient to allow reverse-transmigrated of the migratory dendritic cells from the cushion of extracellular matrix and the monolayer of ECs is about 24-about 48 h. In other embodiments, the period of time sufficient for reverse-transmigrated of the migratory dendritic cells is about 48 hrs.

In one embodiment of any of the methods described, the period of time sufficient to allow reverse-transmigrated of the migratory dendritic cells from the cushion of extracellular matrix and the monolayer of ECs is about 24 h. In other embodiments, the period of time sufficient for reverse-transmigrated of the migratory dendritic cells is about 28 h, about 30 h, about 32 h, about 34 h, about 36 h, about 38 h, about 48 h, about 42 h, about 44 h, about 46 h, about 48 h, and about all the possible integer hours between about 24 h-about 48 h.

In one embodiment of any of the methods described, the human CD33+ and/or CD14+ monocytes or human MCs in the TC and the human newborn PPP used with the adjuvant/antigen/vaccine/immune response stimulating agent are autologous, meaning they come from one donor. The inventors showed demonstrated that autologous plasma on the autonomous development of newborn and adult Mo-DCs, and show that the use autologous materials can accurately reproduce in vivo immune responses.

In one embodiment of any of the methods described, the adjuvant/antigen/vaccine/immune response stimulating agent is any agent that can induce or stimulate the development and transformation of the migratory dendritic cells in the tissue construct described herein to antigen-presenting dendritic cells. In another embodiment, the adjuvant/antigen/vaccine/immune response stimulating agent is any agent that activates migratory dendritic cells in the TC described herein to develop and transform to antigen-presenting dendritic cells.

In one embodiment of any of the methods described, the adjuvant/antigen/vaccine/immune response stimulating agent is any agent that is to be tested for its ability to induce or stimulate development of migratory dendritic cells in the tissue construct described herein to antigen-presenting dendritic cells. In another embodiment, the adjuvant/antigen/vaccine/immune response stimulating agent is any agent that is to be tested for its ability to activate migratory dendritic cells in the TC described herein to antigen-presenting dendritic cells.

In one embodiment of any of the methods described, the antigen/vaccine/immune response stimulating agent is a vaccine. For example, a known vaccine, but known to be effective only in adults.

In one embodiment of any of the methods described, the antigen/vaccine/immune response stimulating agent is an adjuvant.

In one embodiment of any of the methods described, the antigen/vaccine/immune response stimulating agent is a pathogen. In one embodiment, the pathogen is a fragment or an incomplete portion thereof or a whole intact pathogen.

In one embodiment of any of the methods described, the reverse-transmigrated migratory dendritic cells have been activated and transformed to human antigen-presenting dendritic cells in the presence of the adjuvant/antigen/vaccine/immune response stimulating agent introduced into the TC. These human antigen-presenting dendritic cells are collected and can be used in co-cultures with naïve T cells. In one embodiment of any of the methods described, these human antigen-presenting dendritic cells are antigen-specific human dendritic cells, i.e., these cells were induced with a specific adjuvant/antigen/vaccine/immune response stimulating agent, and would themselves induced, stimulate, activate and/or transform other naïve T cells to response to the same specific adjuvant/antigen/vaccine/immune response stimulating agent. Not wishing to be bound by theory, in one embodiment, the human antigen-presenting dendritic cells display a fragment of the specific adjuvant/antigen/vaccine/immune response stimulating agent on their cell surfaces.

In one embodiment of any of the methods described, when the reverse-transmigrated human antigen-presenting dendritic cells collected from tissue constructs are co-cultured with naïve T cells, the naïve T cells and the reverse-transmigrated matured human dendritic cells are autologous (ie, not from the same individual donor). Not wishing to be bound by theory, the matured human dendritic cells "signals" to the naïve T cells to mature such that the resultant matured T cells can elicit an immune respond to the initial antigen/vaccine/immune response stimulating agent that induced the transformation of the migratory dendritic cells to matured dendritic cells in the TCs. In one embodiment, the matured human dendritic cells activate the naïve T cells to mature T cells. In one embodiment, the matured human dendritic cells activate the naïve T cells to mature T cells by way of the fragment of the specific antigen/vaccine/immune response stimulating agent on its cell surface. The matured T cells have increased cell proliferation capability and also produce several cytokines. In one embodiment, the activated mature T cells recognize the initial antigen/vaccine/immune response stimulating agent and response to its presence by cell proliferation and/or production of cytokines.

In one embodiment of any of the methods described, the "signaling" between the matured, autologous human dendritic cells and the naïve autologous T cells captures the in vivo cell-to-cell interactions during an immunization procedure by vaccination.

Accordingly, provided herein are methods of using the TCs or reverse-transmigrated mature dendritic cells for in vitro vaccine efficacy evaluation.

In one embodiment, provided herein is an in vitro method for evaluating the effectiveness of a vaccine in eliciting an immune response to the vaccine, the method comprising: co-culturing human CD4+ CD45RA+ naïve T cells with a first population of human dendritic cells in the presence of human plasma, wherein the human dendritic cells were developed and transformed to antigen-presenting dendritic cells in the presence of a vaccine in the presence of human plasma; incubating the co-culture of human dendritic cells and human CD4+ CD45RA+ naïve T cells in the presence of human plasma for a period of time sufficient to cause activation of the CD4+ CD45RA+ naïve T cells; introducing to the resultant activated human CD4+ CD45RA+ T cells in culture to a second population of human dendritic cells in the presence of human plasma; co-culturing the second population of human dendritic cells and the activated human CD4+ CD45RA+ T cells for a period of time sufficient to cause further activation and proliferation of the CD4+ CD45RA+ T cells in culture; and analyzing for the production of cytokines wherein the presence of cytokines over that in the absence of added dendritic cells indicates that the vaccine is an effective vaccine in stimulating a human immune response. In one embodiment, the activated CD4+ CD45RA+ T cells subsequently differentiate into CD45RO+ T cells. In one embodiment, the human plasma is human PPP.

In one embodiment, provided herein is an in vitro method for evaluating the effectiveness of a vaccine in eliciting an immune response to the vaccine, the method comprising: providing a first and second population of human dendritic cells that are developed and transformed to antigen-presenting dendritic cells in the presence of an adjuvant/antigen/vaccine/immune response stimulating agent and human plasma; co-culturing human CD4+ CD45RA+ naïve T cells with the first population of human dendritic cells in the presence of human platelet poor plasma; incubating the co-culture of human dendritic cells and human CD4+ CD45RA+ naïve T cells in the presence of human plasma for a period of time sufficient to cause activation of the CD4+ CD45RA+ naïve T cells; introducing to the resultant activated human CD4+ CD45RA+ T cells in culture to the second population of human dendritic cells in the presence of human plasma; co-culturing the second population of human dendritic cells and the activated human CD4+ CD45RA+ T cells for a period of time sufficient to cause further activation and proliferation of the CD4+ CD45RA+ T cells in culture; and analyzing for the production of cytokines wherein the presence of cytokines over that in the absence of added dendritic cells indicates that the vaccine is an effective vaccine in stimulating a human immune response. In one embodiment, the activated CD4+ CD45RA+ T cells subsequently differentiate into CD45RO+ T cells. In one embodiment, the human plasma is human PPP.

In one embodiment, provided herein is an in vitro method for evaluating the effectiveness of a vaccine in eliciting an immune response to the vaccine, the method comprising: introducing a vaccine to a tissue construct in the presence of human plasma, wherein the tissue construct was previously prepared by: providing a cushion of extracellular matrix comprising human collagen, incubating the extracellular matrix in the presence of glucose-6-phosphate for a sufficient period of time to allow the collagen to mature, seeding the cushion of extracellular matrix with human endothelial cells, culturing the human ECs to a confluent monolayer in the presence of human plasma, introducing human MCs or CD33+ and/or CD14+ monocytes to the confluent monolayer of human endothelial cells in the presence of non-heat inactivated human serum albumin, incubating for a period of time sufficient to allow the MCs or monocytes to undergo autonomous extravasation of the confluent monolayer of human endothelial cells and colonization of the cushion of extracellular matrix, and removing the non-extravasated human MCs or monocytes; incubating the tissue construct for a period of time sufficient for the extravasated human MCs or monocytes to reverse-transmigrated the confluent monolayer of human ECs; collecting the reverse-transmigrated MCs which have developed into antigen-presenting dendritic cells in the presence of the vaccine; co-culturing the human dendritic cells with human CD4+ CD45RA+ naïve T cells in the presence of human plasma; incubating the co-culture of dendritic cells and naïve T cells in the presence of human plasma for a period of time sufficient to cause activation of the CD4+ CD45RA+ naïve T cells; introducing the activated human CD4+ CD45RA+ T cells to a second population of human dendritic cells in the presence of human plasma; co-culturing the dendritic cells and activated human CD4+ CD45RA+ T cells in the presence of human plasma for a period of time sufficient to cause further activation and proliferation of the activated human CD4+ CD45RA+ T cells in culture; and analyzing for the production of cytokines wherein the presence of cytokines over that in the absence of added dendritic cells indicates that the vaccine is an effective vaccine in stimulating a human immune response. In one embodiment, the activated CD4+ CD45RA+ T cells subsequently differentiate into CD45RO+ T cells. In one embodiment, the human plasma is human PPP.

In other embodiments of the in vitro efficacy test methods described herein, other immune cells can be used in place of CD4+ CD45RA+ naïve T cells. Non-limiting examples are B cells, CD8+ T cells (naïve CD45RA+ and memory/activated CD45RO+) and CD4+ T cells (naïve CD45RA+ and memory/activated CD45RO+), natural killer (NK) T cells, and regulatory T cells.

In one embodiment of any of the methods described, the populations of human dendritic cells used in the in vitro vaccine efficacy tests described are produced using the TCs and methods of making tissue constructs described herein. In one embodiment of any of the methods described, the populations of human dendritic cells are produced in the presence of an adjuvant/antigen/vaccine/immune response stimulating agent in the presence of human plasma using the TCs and methods of making tissue constructs described herein. In one embodiment, the populations of human dendritic cells used in the in vitro vaccine efficacy tests described are antigen-presenting dendritic cells.

In one embodiment of any of the methods described, the populations of human dendritic cells used in the in the in vitro vaccine efficacy tests described were previously cryopreserved.

In one embodiment of any of the methods described, the first, second, or additional populations of human dendritic cells used in the in the in vitro vaccine efficacy tests are produced using the same adjuvant/antigen/vaccine/immune response stimulating agent.

In one embodiment of any of the methods described, the populations of human dendritic cells, human CD4+ CD45RA+ naïve T cells and the human PPP are autologous, meaning they are derived or obtained from one donor; in other words, from the same individual donor.

In other embodiments of any of the methods described, the human platelet poor plasma is not autologous with the populations of human dendritic cells and human CD4+ CD45RA+ naïve T cells. In one embodiment, the human dendritic cells, human CD4+ CD45RA+ naïve T cells and the human platelet poor plasma are from an age-matched donor. For example, the human platelet poor plasma is allogeneic or xenogeneic to the populations of matured human dendritic cells and human CD4+ CD45RA+ naïve T cells used in the in vitro vaccine efficacy tests described.

In one embodiment of any of the in vitro vaccine efficacy tests described, the human CD4+ CD45RA+ naïve T cells are CD45RO negative.

In one embodiment of any of the in vitro vaccine efficacy tests described, the populations of human dendritic cells, human CD4+ CD45RA+ naïve T cells and the human PPP are obtained or derived from a newborn, or an adult, or an adolescent, or a child. In other words, the populations of human dendritic cells, human CD4+ CD45RA+ naïve T cells and the human PPP are obtained or derived from one individual, that individual being a newborn, an adult, an adolescent, a child. In one embodiment, when the human dendritic cells, human CD4+ CD45RA+ naïve T cells and the human PPP are obtained or derived from an adult or an adolescent, the cells and plasma are from age-matched donors. In other words, the cells and plasma are from adults of only the 21-30 age group adults, or only the 31-40 age group adults, or only the 41-50 age group adults, or only the 51-60 age group adults, or only the 61-70 age group adults, or only the above 70 age group adults.

In one embodiment of any of the in vitro vaccine efficacy tests described, the autologous human CD4+ CD45RA+ naïve T cells, the human dendritic cells and the human PPP are obtained or derived from a newborn, meaning they come from one human newborn donor. Accordingly, in one embodiment of any of the in vitro vaccine efficacy tests described, human newborn CD4+ CD45RA+ naïve T cells are used. In another embodiment of any of the in vitro vaccine efficacy tests described, human dendritic cells derived from human newborn MCs or human newborn CD33+ and/or CD14+ selected monocytes are used. In another embodiment of any of the in vitro vaccine efficacy tests described, human newborn PPP is used.

In one embodiment of any of the in vitro vaccine efficacy tests described, the cells and plasma are obtained or derived from the umbilical cord of a newborn. In one embodiment, the umbilical cord of the newborn was previously cryopreserved.

In one embodiment of any of the in vitro vaccine efficacy tests described, the human platelet poor plasma is not heat inactivated. By "not heat inactivated" mean not incubating at 56° C. for at least about 30 minutes.

In one embodiment of any of the in vitro vaccine efficacy tests described, the period of time sufficient to cause activation of the CD4+ CD45RA+ naïve T cells in culture or further activation of the CD4+ CD45RA+ activated T cells in culture is at least one day. In other embodiments of any of the in vitro vaccine efficacy tests described, the period of time is at least two days, at least three days, at least four days, at least five days, at least six days, at least seven days, at least eight days, at least nine days, at least ten days, at least 11 days, at least 12 days, at least 13 days, at least 14 days, at least 15 days, at least 16 days, at least 17 days, at least 18 days, at least 19 days, at least 20 days, or at least 21 days.

In other embodiments of any of the in vitro vaccine efficacy tests described, the period of time sufficient to cause activation of the CD4+ CD45RA+ naïve T cells in culture or further activation of the CD4+ CD45RA+ activated T cells in culture is about two days, about three days, about four days, about five days, about six days, about seven days, about eight days, about nine days, about ten days, about 11 days, about 12 days, about 13 days, about 14 days, about 15 days, about 16 days, about 17 days, about 18 days, about 19 days, about 20 days, or about 21 days.

In other embodiments of any of the in vitro vaccine efficacy tests described, the period of time sufficient to cause activation of the CD4+ CD45RA+ naïve T cells in culture or further activation of the CD4+ CD45RA+ activated T cells in culture is at least 7 days, about 7 days, or about 7-about 21 days.

In one embodiment of any of the in vitro vaccine efficacy tests described, the vaccine being evaluated is the vaccine used in vitro used to produce the first and second population of human dendritic cells wherein tissue constructs described herein are used. It is contemplated that any adjuvant, antigen, vaccine formulation or immune response stimulating agent can be evaluated in the in vitro vaccine efficacy tests described.

In one embodiment of any of the in vitro vaccine efficacy tests described, the method further comprises analyzing the proliferation of the activated CD4+ CD45RA+ T cells in culture wherein an increase in cell proliferation or cell number over that in the absence of added human dendritic cells indicates that the adjuvant, antigen, vaccine formulation or immune response stimulating agent is effective in stimulating a human immune response.

In one embodiment of any of the in vitro vaccine efficacy tests described, the method further comprising challenging the activated CD4+ CD45RA+ T cells in culture with a third population of human dendritic cells in the presence of human plasma prior to the cytokines analysis and cell proliferation, wherein the third population of human dendritic cells were exposed to the same adjuvant, antigen, vaccine formulation or immune response stimulating agent as the first and second population of human dendritic cells.

In one embodiment of any of the in vitro vaccine efficacy tests described, the first, second and third populations of human dendritic cells are produced with the same adjuvant, antigen, vaccine formulation or immune response stimulating agent being evaluated.

In one embodiment of any of the in vitro vaccine efficacy tests described, the first, second and third populations of human dendritic cells are autologous, meaning they are derived or obtained from one donor.

In one embodiment of any of the in vitro vaccine efficacy tests described, the first, second and third populations of human dendritic cells, human CD4+ CD45RA+ naïve T cells, B cells, CD8+ T cells, CD4+ T cells, NK T cells, regulatory T cells, and the human platelet poor plasma are autologous, meaning they are derived or obtained from one donor.

In one embodiment of any of the in vitro vaccine efficacy tests described, first, second and third populations of human dendritic cells, human CD4+ CD45RA+ naïve T cells and the human PPP are obtained or derived from a newborn, an adult, an adolescent, or a child. In one embodiment, when the human dendritic cells, human CD4+ CD45RA+ naïve T cells and the human PPP are obtained or derived from an adult or an adolescent, the cells and plasma are from age-matched donors. For example, human dendritic cells, human CD4+ CD45RA+ naïve T cells and the human PPP are obtained or derived from only the 21-30 age group adults, or only the 31-40 age group adults, or only the 41-50 age group adults, or only the 51-60 age group adults, or only the 61-70 age group adults, or only the above 70 age group adults.

In one embodiment of any of the in vitro vaccine efficacy tests described, the autologous human CD4+ CD45RA+ naïve T cells, the first, second and third populations of human dendritic cells and the human PPP are obtained or derived from a newborn, meaning they come from one human newborn donor. Accordingly, in one embodiment of any of the in vitro vaccine efficacy tests described, human newborn CD4+ CD45RA+ naïve T cells are used. In another embodiment of any of the in vitro vaccine efficacy tests described, the first, second and third populations of human dendritic cells are derived from human newborn MCs or human newborn CD33+ and/or CD14+ selected monocytes. In another embodiment of any of the in vitro vaccine efficacy tests described, human newborn PPP is used. In one embodiment, the human CD4+ CD45RA+ naïve T cells, the first, second and third populations of human dendritic cells and the human PPP are autologous.

In one embodiment of any of the in vitro vaccine efficacy tests described, the autologous human newborn CD4+ CD45RA+ naïve T cells, the first, second and third populations of human newborn dendritic cells and the human newborn PPP are obtained or derived from the umbilical cord of a newborn. In one embodiment, the umbilical cord of the newborn was previously cryopreserved.

In one embodiment of any of the in vitro vaccine efficacy tests described, the cytokine analyzed is selected from a non-limiting group consisting of IL-1, IL-10, IL-12, IL-2, IL-4, IFN-gamma and TNF-alpha.

Various methods of measuring cytokines that is produced by the activated T cells are known in the art, for example, Enzyme-linked immunosorbent assay (ELISA). In one embodiment, the cytokines that is produced by the activated T cells are secreted into the cell culture media used in the co-culture. Where the amount cytokines produced by the activated T cells is increased over that in the absence of added matured human dendritic cells indicates that the vaccine is an effective vaccine in stimulating a human immune response. In some embodiments, the increased in cytokines produced is at least 10%, at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, or more over the amount of cytokines produced by the T cells in the absence of added matured human dendritic cells.

Various methods of measuring cell proliferation are known in the art, for example, by cell counting and by $H^3$-thymidine incorporation. An increased in cell proliferation of the T cells co-cultured with matured human dendritic cells over the cell proliferation of T cells in the absence of added matured human dendritic cells indicates that the vaccine is an effective vaccine in stimulating a human immune response. In some embodiments, an increased in cell proliferation is at least 10%, at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, or more over the amount of cell proliferation of T cells not co-cultured with matured human dendritic cells.

In one embodiment, provided herein is a kit for making a TC described herein. The kit comprises the components necessary to prepare a TC, the components include but are not limited to at least a container for holding or containing the TC, e.g., tissue culture vessel, at least one extracellular matrix, human ECs, and glucose-6-phosphate. Accordingly, provided herein is a kit comprises at least a container for holding or containing a TC; at least one extracellular matrix; and glucose-6-phosphate.

In one embodiment of the kit described herein, the least one extracellular matrix comprises collagen. In one embodiment, the collagen is human collagen. In one embodiment, the human collagen is Type I collagen. In another embodiment, the human collagen is glycosylated or glycated.

In one embodiment of any method or TC or kit described, the human collagen is derived for human fibroblast.

In another embodiment of the kit described herein, the least one extracellular matrix comprises fibronectin. In one embodiment, the fibronectin is human fibronectin.

In one embodiment of the kit described herein, the kit further comprises human ECs. In one embodiment, the human endothelial cell is human primary EC. In one embodiment, the human ECs of the kit are from a single donor.

In another embodiment of the kit described herein, the kit further comprises instructions and components for harvesting and/or preparing human primary ECs such as tissue culture dishes, cell culture media, and enzymes to digest tissues e.g., collagenase.

In one embodiment of the kit described herein, the kit further comprises human MCs or human CD33+ and/or CD14+ selected monocytes. In one embodiment, the human MCs or human CD33+ and/or CD14+ selected monocytes are from a single donor. In another embodiment of the kit described herein, the human MCs or human CD33+ and/or CD14+ selected monocytes are obtained or derived from a newborn or adult. In another embodiment of the kit described herein, the human MCs or human CD33+ sand/or CD14+ elected monocytes are obtained or derived from an adolescent or a child.

In another embodiment of the kit described herein, the kit further comprises instructions and components for harvesting and/or preparing human MCs or human CD33+ and/or CD14+ selected monocytes for a human sample of bone marrow, circulating peripheral blood or umbilical cord blood. In another embodiment of the kit described herein, the kit further comprises instructions and components for collecting a human sample of bone marrow, circulating peripheral blood or umbilical cord blood. In one embodiment, the kit further comprises components to isolate cells from a human sample of bone marrow, circulating peripheral blood or umbilical cord blood, and components to isolate blood plasma.

In one embodiment of the kit described herein, the kit further comprises human plasma which can be derived from a newborn or an adult. In other embodiment, the human plasma is from an adolescent or a child. In other embodiment, the human plasma is from a single donor. In another embodiment, the human plasma is from pooled from more than one donor. In one embodiment, the human plasma is plasma pooled from more than one newborn. In one embodiment, the human plasma has been previously been cryopreserved. In one embodiment, the human plasma is not heat inactivated. In another embodiment, the kit the human plasma is heat inactivated. In a further embodiment, the human plasma is intact, i.e., not substantially depleted of platelets and divalent cations.

In one embodiment of the kit described herein, the kit further comprises human serum albumin. In other embodiment, the human serum albumin is from a newborn or an adult. In other embodiment, the human serum albumin is from an adolescent or a child. In another embodiment, the human serum albumin is from pooled from more than one donor. In one embodiment, the human serum albumin is plasma pooled from more than one newborn. In one embodiment, the human serum albumin has been previously been cryopreserved. In one embodiment, the human serum albumin is not heat inactivated. In one embodiment, the human serum albumin is pyrogen-free.

In one embodiment of the kit described herein, the kit further comprises human PPP. In other embodiment, the human PPP is from a newborn or an adult. In other embodiment, the human PPP is from an adolescent or a child. In other embodiment, the human PPP is from a single donor. In another embodiment, the human PPP is from pooled from more than one donor. In one embodiment, the human PPP is plasma pooled from more than one newborn. In one embodiment, the human PPP has been previously been cryopreserved. In one embodiment, the human PPP is not heat inactivated. In another embodiment, the kit the human PPP is heat inactivated.

In one embodiment of the kit described herein, the human endothelial cells, human MCs and human CD33+ and/or CD14+ selected monocytes are from one representative class of donors, meaning the human ECs, human MCs and human CD33+ and/or CD14+ selected monocytes of each kit are from only adults, from only adolescents, from only newborns, or only children. In one embodiment, the adult or children of donors are age-matched. Alternatively, the kit provides the human ECs, human MCs and human CD33+ and/or CD14+ selected monocytes are from more than one representative class of donors, e.g., human ECs, human MCs and human CD33+ and/or CD14+ selected monocytes are from adult in the age 51-60 age group and also human ECs, human MCs and human CD33+ and/or CD14+ selected monocytes are from a newborn. This alternative allows the user of the kit to make adult tissue constructs for testing vaccine efficacy in an adult immune system and also make neonatal tissue constructs for testing vaccine efficacy in a neonatal immune system.

In one embodiment of the kit described herein, the human serum albumin, human PPP or human plasma is not substantially depleted of divalent ions such as calcium or magnesium. In one embodiment, the human serum albumin, human PPP or human plasma is not prepared in the presence of a chelating agent. In one embodiment, the human serum albumin, human PPP or human plasma is prepared in the presence of heparin.

In one embodiment of the kit described herein, the human MCs, human CD33+ and/or CD14+ selected monocytes and human platelet poor plasma are autologous and from one donor.

The present invention can be defined in any of the following numbered paragraphs:

[1] A method comprising:
   (a) culturing endothelial cells on a cushion of extracellular matrix for a period of time sufficient to obtain a monolayer;
   (b) introducing human mononuclear cells (MCs) to the monolayer of endothelial cells;
   (c) culture for a period of time sufficient to allow the human MCs to autonomous extravasation of the monolayer of endothelial cells and colonize the cushion of extracellular matrix;
   (d) removing non-extravasated MCs after the period of time in step c;
   (e) introducing an agent in the presence of human platelet poor plasma to the culture and cushion of extracellular matrix of step d;
   (f) incubating the culture for a period of time sufficient to allow reverse-transmigration of the human MCs from the monolayer of endothelial cells; and
   (g) collecting the reverse-transmigrated human MCS which have developed into migratory dendritic cells in the presence of the agent.

[2] The method of claim 1, wherein the cushion of extracellular matrix comprising collagen.

[3] The method of claim 2, wherein the collagen is human collagen.

[4] The method of claim 2, wherein the collagen is bovine collagen.

[5] The method of claim 2, wherein the collagen is porcine collagen.

[6] The method of any one of claims 2-5, wherein the collagen is Type 1 collagen.

[7] The method of claim 3, wherein the human collagen is human Type 1 collagen.

[8] The method of any one of claims 2-7, wherein the collagen is glycated.

[9] The method of any one of claim 3, 6, 7 or 8, wherein the human collagen is human collagen matured in the presence of glucose-6-phosphate.

[10] The method of claim 9, wherein the human collagen is matured in the presence of glucose-6-phosphate for at least 48 h.

[11] The method of claim 1, 2 or 3, wherein the human collagen is human collagen matured in the presence of glucose-6-phosphate for up to 5 days.

[12] The method of any one of claims 2-7, wherein the cushion of extracellular matrix further comprising fibronectin.

[13] The method of claim 12, wherein the fibronectin is human fibronectin.

[14] The method of any one of claims 1-13, wherein the endothelial cells are human primary endothelial cells.

[15] The method of claim 14, wherein the human primary endothelial cells are cultured in the presence of human newborn plasma.

[16] The method of claim 14 or 15, wherein the human primary endothelial cells are obtained from one single donor.

[17] The method of claim 14, 15 or 16, wherein the human primary endothelial cells are obtained from human umbilical cord.

[18] The method of any one of claims 14-17, wherein the human primary endothelial cells are cultured to a confluent monolayer.

[19] The method of claim 18, wherein the confluent monolayer is at least 90% confluent.

[20] The method of claim 18 or 19, wherein the confluent monolayer is about 90%-100% confluent.

[21] The method of any one of claims 1-20, wherein the period of time to obtain a monolayer is at least 24 h.

[22] The method of any one of claims 1-21, wherein the period of time to obtain a monolayer is about 24 h to 3 days.

[23] The method of any one of claims 15-22, wherein the human plasma is not heat inactivated.

[24] The method of any one of claims 15-22, wherein the human plasma is heat inactivated.

[25] The method of any one of claims 15-24, wherein the human plasma is from a newborn, an adult, an adolescent or a child.

[26] The method of any one of claims 15-25, wherein the human plasma is plasma pooled from more than one donor.

[27] The method of any one of claims 15-26, wherein the human plasma is obtained from human umbilical cord blood, placental blood or circulating peripheral blood.

[28] The method of any one of claims 15-27, wherein the human plasma has been previously been cryopreserved.

[29] The method of any one of claims 1-28, wherein the human plasma is used at least 40%.

[30] The method of any one of claims 1-29, wherein the human plasma at about 40%-100%.

[31] The method of any one of claims 1-30, wherein the human plasma at about 50%

[32] The method of any one of claims 1-31, wherein the human plasma is human newborn plasma.

[33] The method of any one of claims 1-32, wherein the human MCs are from a newborn, an adult, an adolescent or a child.

[34] The method of any one of claims 1-33, wherein the human MCs are derived from one donor.

[35] The method of any one of claims 1-33, wherein the human MCs are not pooled from more than one donor.

[36] The method of any one of claims 1-35, wherein the human MCs cells are cells previously cryopreserved.

[37] The method of any one of claims 1-36, wherein the human MCs are obtained from human umbilical cord blood, placental blood or bone marrow.

[38] The method of any one of claims 1-37, wherein the human MCs are human newborn MCs.

[39] The method of any one of claims 1-37, wherein the human MCs are human CD 33+ and/or CD14+ monocytes.

[40] The method of claim 39, wherein the human CD33+ and/or CD14+ monocytes are from one donor.

[41] The method of claim 39, wherein the human CD33+ and/or CD14+ monocytes are not pooled from more than one donor.

[42] The method of any one of claims 39-41, wherein the human CD33+ and/or CD14+ monocytes are obtained from human umbilical cord blood, placental blood or bone marrow.

[43] The method of any one of claims 1-42, wherein the human MCs or human CD 33+ and/or CD14+ monocytes are cultured in the presence of human serum albumin.

[44] The method of any one of claims 39-43, wherein the human CD33+ and/or CD14+ monocytes are human newborn CD 33+ and/or CD14+ monocytes.

[45] The method of claim 44, wherein the human serum albumin is not heat inactivated.

[46] The method of claim 45, wherein the human serum albumin is pyrogen-free.

[47] The method of any one of claims 45-46, wherein the human serum albumin is clinical grade human serum albumin.

[48] The method of any one of claims 1-47, wherein the human MCs are not cultured in the presence of exogenous cytokines or immune response stimulating agent.

[49] The method of any one of claims 1-48, wherein the human MCs are not cultured in the presence of GM-CSF.

[50] The method of any one of claims 1-48, wherein the human MCs are not cultured in the presence of IL-4.

[51] The method of any one of claims 1-50, wherein the human CD 33+ and/or CD14+ monocytes or human MCs and the human platelet poor plasma are autologous, meaning they come from one donor.

[52] The method of any one of claims 39-51, wherein the human CD 33+ and/or CD14+ monocytes are obtained from human umbilical cord blood, placental blood or bone marrow.

[53] The method of any one of claims 39-52, wherein the human CD 33+ and/or CD14+ monocytes has been previously been cryopreserved.

[54] The method of any one of claims 1-53, wherein the period of time sufficient to allow the human MCs to autonomous extravasation of the monolayer of endothelial cells and colonize the cushion of extracellular matrix is at least 0.5 h.

[55] The method of any one of claims 1-54, wherein the period of time sufficient to allow the human MCs to autonomous extravasation of the monolayer of endothelial cells and colonize the cushion of extracellular matrix is about 0.5 h to 4 h.

[56] The method of any one of claims 1-55, wherein the period of time sufficient to allow the human MCs to autonomous extravasation of the monolayer of endothelial cells and colonize the cushion of extracellular matrix is about 1.5 h to 2 h.

[57] The method of any one of claims 1-56, wherein the agent is any agent that can induce or stimulate development of the human MCs to mature to dendritic cells.

[58] The method of any one of claims 1-57, wherein the agent is any agent that is to be tested for its ability to induce or stimulate development of the human MCs to mature to dendritic cells.

[59] The method of claim 57, the agent is a vaccine formulation.

[60] The method of claim 57, the agent is an adjuvant.

[61] The method of claim 57, 58 or 59, the agent is a pathogen.

[62] The method of claim 61, the pathogen is a fragment/incomplete portion thereof or a whole intact pathogen.

[63] The method of any one of claims 1-63, wherein the human newborn platelet poor plasma is not heat inactivated.

[64] The method of any one of claims 1-63, wherein the human newborn platelet poor plasma is used at least at 50% in step d.

[65] The method of any one of claims 1-64, wherein the human newborn platelet poor plasma is used at about 50%-100% in step d.

[66] The method of any one of claims 1-65, wherein the human newborn platelet poor plasma is used at about 100% in step d.

[67] The method of any one of claims 1-66, wherein the period of time sufficient to allow reverse-transmigrated of the human MCs from the monolayer of endothelial cells is at least 24 h.

[68] The method of any one of claims 1-67, wherein the period of time sufficient to allow reverse-transmigrated of the human MCs from the monolayer of endothelial cells is about 24-48 h.

[69] The method of any one of claims 1-68, wherein the period of time sufficient to allow reverse-transmigrated of the human MCs from the monolayer of endothelial cells is about 48 h.

[70] The method of any one of claims 1-69, wherein the human plasma, human platelet poor plasma or human serum albumin does not contain a chelating agent.

[71] The method of any one of claims 1-70, wherein the human plasma, human platelet poor plasma or human serum albumin is prepared with heparin.

[72] The method of any one of claims 1-71, wherein the human plasma, human platelet poor plasma or human serum albumin is prepared in the absence of a chelating agent.

[73] An in vitro method of preparing a population of human newborn dendritic cells comprising:
(a) introducing an agent in the presence of human platelet-poor plasma to a tissue construct, wherein the tissue construct was previously prepared by:
providing a cushion of extracellular matrix;
incubating the extracellular matrix in the presence of glucose-6-phosphate for a sufficient period of time to allow the collagen to mature;
seeding the cushion of extracellular matrix with human endothelial cells;
culturing the human endothelial cells to a confluent monolayer in the presence of human plasma;
introducing human mononuclear cells (MCs) to the monolayer of human endothelial cells in the presence of human serum albumin;
incubating for a period of time sufficient to allow human MCs to undergo autonomous extravasation of the monolayer of human endothelial cells; and
removing the non-extravasated human MCs;
(b) incubating the tissue culture for a period of time sufficient for the extravasated human MCs to reverse-transmigrate across the monolayer of human endothelial cells; and
(c) collecting the reverse-transmigrated human MCs which have developed into antigen-presenting dendritic cells in the presence of the agent.

[74] The method of claim 73, wherein the human MCs are human CD 33+ and/or CD14+ monocytes.

[75] The method of claim 74, wherein the human CD 33+ and/or CD14+ monocytes are from one donor.

[76] The method of claim 75, wherein the human CD 33+ and/or CD14+ monocytes are not pooled from more than one donor.

[77] The method of any one of claims 73-76, wherein the human CD 33+ and/or CD14+ monocytes are obtained from human umbilical cord blood.

[78] The method of any one of claims 73-77, wherein the human serum albumin is pyrogen-free.

[79] The method of any one of claims 73-78, wherein the human serum albumin is clinical grade human serum albumin.

[80] The method of any one of claims 73-80, wherein the human MCs are not cultured in the presence of exogenous cytokines or immune response stimulating agent.

[81] The method of any one of claims 73-80, wherein the human MCs are not cultured in the presence of GM-CSF.

[82] The method of any one of claims 73-81, wherein the human MCs are not cultured in the presence of IL-4.

[83] The method of any one of claims 73-82, wherein the human CD 33+ and/or CD14+ monocytes or human MCs and the human platelet poor plasma are autologous, meaning they come from one donor.

[84] The method of any one of claims 73-83, wherein the human CD 33+ and/or CD14+ monocytes are obtained from human umbilical cord blood.

[85] The method of any one of claims 73-84, wherein the human CD 33+ and/or CD14+ monocytes has been previously been cryopreserved.

[86] The method of any one of claims 73-85, wherein the agent is any agent that can induce or stimulate development and transformation of the human MCs to antigen-presenting dendritic cells.

[87] The method of any one of claims 73-86, wherein the agent is any agent that is to be tested for its ability to induce or stimulate development and transformation of the human MCs to antigen-presenting dendritic cells.

[88] The method of claim 86, the agent is a vaccine.

[89] The method of claim 87, the agent is an adjuvant.

[90] The method of claim 86, 87 or 88, the agent is a pathogen.

[91] The method of claim 90, the pathogen is a fragment or an incomplete portion thereof or a whole intact pathogen.

[92] The method of any one of claims 73-91, wherein the human platelet poor plasma is not heat inactivated.

[93] The method of any one of claims 73-92, wherein the human platelet poor plasma is used at least at 50% in step b.

[94] The method of any one of claims 73-93, wherein the human platelet poor plasma is used at about 50%-100% in step b.

[95] The method of any one of claims 73-94, wherein the human platelet poor plasma is used at 100% in step b.

[96] The method of any one of claims 73-95, wherein the period of time sufficient to allow reverse-transmigration of the MCs across the monolayer of endothelial cells is at least 24 h.

[97] The method of any one of claims 73-96, wherein the period of time sufficient to allow reverse-transmigration of the MCs across the monolayer of endothelial cells is about 24-48 h.

[98] The method of any one of claims 73-97, wherein the period of time sufficient to allow reverse-transmigration of the MCs across the monolayer of endothelial cells is 48 h.

[99] The method of any one of claims 73-98, wherein the human plasma, human newborn platelet poor plasma or human serum albumin does not contain a chelating agent.

[100] The method of any one of claims 73-99, wherein the human plasma, human platelet poor plasma or human serum albumin is prepared with heparin.

[101] The method of any one of claims 73-100, wherein the human plasma, human platelet poor plasma or human serum albumin is prepared in the absence of a chelating agent.

[102] An in vitro method for evaluating the effectiveness of an agent in eliciting a human antigen-specific immune response to the antigen, the method comprising:
  (a) co-culturing human CD4+ CD45RA+ naïve T cells with a first population of human dendritic cells of claims 1-101 in the presence of human platelet-poor plasma;
  (b) incubating the co-culture of dendritic cells and naïve T cells for a period of time sufficient to cause activation of the CD4+ CD45RA+ naïve T cells;
  (c) introducing to the activate T cells from the culture of step b to a second population of human dendritic cells of claims 1-101 in the presence of human platelet-poor plasma;
  (d) co-culturing the dendritic cells and activated T cells of step c for a period of time sufficient to further activate the activate T cells in culture of step b; and
  (e) analyzing the co-culture media for a cytokine wherein increased presence of the cytokine over that in the absence of added dendritic cells indicates that the antigen is effective in stimulating human naïve antigen-specific immune response.

[103] The method of claim 102, wherein the human newborn CD4+ CD45RA+ naïve T cells are CD45RO negative.

[104] The method of claim 103, wherein the human newborn CD4+ CD45RA+ naïve T cells, the dendritic cells and the human newborn platelet poor plasma are autologous, meaning they come from one donor.

[105] The method of claim 102, 103 or 104, wherein the human platelet poor plasma is not heat inactivated.

[106] The method of any one of claims 102-105, wherein the period of time sufficient to cause activation of the naïve T cells in culture is at least one day.

[107] The method of any one of claims 102-106, wherein the period of time sufficient to cause activation of the newborn naïve T cells in culture is at least 7 days, about 7 days, or about 7-15 days.

[108] The method of any one of claims 102-107, wherein the agent being evaluated is the agent used in vitro to produce the first and second population of human dendritic cells of claims 1-101.

[109] The method of any one of claims 102-105 further comprising analyzing the cells of step (e) for cell proliferation wherein an increase in cell proliferation or cell number over that in the absence of added dendritic cells indicates that the antigen is effective in stimulating human naïve antigen-specific immune response.

[110] The method of any one of claims 102-109 further comprising challenging the cells in culture of step (d) with a third population of human dendritic cells of claims 1-101 prior to analysis for cytokines and/or cell proliferation, wherein the third population of human dendritic cells were exposed to the same agent as the first and second population of human newborn dendritic cells in steps (a) and (d).

[111] The method of claim 110, wherein the third population of human dendritic cells is also produced with the same agent being evaluated.

[112] The method of any one of claims 102-111, wherein the cytokine analyzed is selected from a group consisting of IL-1, IL-10, IL-12, IL-2, IL-4, IFN-gamma and TNF-alpha.

[113] An in vitro method for evaluating the effectiveness of an agent in eliciting a human naïve antigen-specific immune response to the antigen, the method comprising:
  (a) introducing an agent in the presence of human platelet poor plasma to a tissue construct, wherein the tissue construct was previously prepared by:
    providing a cushion of extracellular matrix comprising;
    incubating the extracellular matrix in the presence of glucose-6-phosphate for a sufficient period of time to allow the collagen to mature;
    seeding the cushion of extracellular matrix with human endothelial cells;
    culturing the human primary endothelial cells to a monolayer in it the presence of human plasma;
    introducing human mononuclear cells (MCs) to the culture well having the monolayer of human endothelial cells in the presence of human serum albumin;
    incubating for a period of time sufficient to allow the human MCs to undergo autonomous extravasation of the monolayer of human endothelial cells; and
    removing the non-extravasated human MCs;
  (b) incubating the tissue construct for a period of time sufficient for the extravasated human MCs to reverse-transmigrate across the monolayer of human endothelial cells;
  (c) collecting the reverse-transmigrated human MCs which have developed into matured dendritic cells in the presence of the agent;
  (d) co-culturing the matured dendritic cells of step (c) with human CD4+ CD45RA+ naïve T cells in the presence of human platelet poor plasma;
  (e) incubating the co-culture of dendritic cells and naïve T cells for a period of time sufficient to cause activation of the CD4+ CD45RA+ naïve T cells;
  (f) introducing to the activated T cells in culture of step e a second population of human matured dendritic cells of step c;
  (g) co-culturing the human matured dendritic cells and activated T cells of step f for a period of time sufficient to cause further activation of the previously activated T cells in culture of step e; and
  (h) analyzing the co-culture media for a cytokine wherein an increase presence of cytokine over that in the absence of added dendritic cells indicates that the agent is effective in stimulating human naïve newborn antigen-specific immune response.

[114] The method of claim 113 further comprising analyzing the cells of step (h) for cell proliferation wherein an increase in cell proliferation over that in the absence of added dendritic cells indicates that the antigen is effective in stimulating human immune response.

[115] The method of claim 114 further comprising introducing a third batch of reverse-transmigrated dendritic cells prepared according to step (a) to step (e) to the cells in culture of step (h) prior to analysis for cytokines and cell proliferation.

[116] A method of preparing a tissue construct, the method comprising:
(a) providing a cushion of extracellular matrix;
(b) culturing human endothelial cells on the cushion of extracellular matrix in the presence of human plasma for a period of time sufficient for the cells to form a monolayer;
(c) adding human MCs to the monolayer of human endothelial cells;
(d) culturing the MCs for a period of time sufficient for autonomous extravasation of the MCs through the monolayer of human endothelial cells and colonize the cushion of extracellular matrix.

[117] The method of claim 116, wherein the cushion of extracellular matrix comprising collagen.

[118] The method of claim 117, wherein the collagen is human collagen.

[119] The method of claim 117, wherein the collagen is bovine collagen.

[120] The method of claim 117, wherein the collagen is porcine collagen.

[121] The method of any one of claims 116-120, wherein the collagen is Type 1 collagen.

[122] The method of claim 121, wherein the human collagen is human Type 1 collagen.

[123] The method of any one of claims 116-121, wherein the collagen is glycated.

[124] The method of any one of claim 116, 120, 121 or 122, wherein the human collagen is human collagen matured in the presence of glucose-6-phosphate.

[125] The method of claim 124, wherein the human collagen is matured in the presence of glucose-6-phosphate for at least 48 h.

[126] The method of claim 124, wherein the human collagen is human collagen matured in the presence of glucose-6-phosphate for up to 5 days, from 2-5 days, from 2-3 days, from 2-4 days, from 3-4 days, from 4-5 days, or from 3-5 days.

[127] The method of any one of claims 116-126, wherein the cushion of extracellular matrix further comprising fibronectin.

[128] The method of claim 127, wherein the fibronectin is human fibronectin.

[129] The method of any one of claims 116-128, wherein the endothelial cells are human primary endothelial cells.

[130] The method of claim 129, wherein the human primary endothelial cells are cultured in the presence of human plasma.

[131] The method of claim 129 or 130, wherein the human primary endothelial cells are obtained from one single donor.

[132] The method of claim 129, 130 or 131, wherein the human primary endothelial cells are obtained from human umbilical cord.

[133] The method of any one of claims 129-132, wherein the human primary endothelial cells are cultured to a confluent monolayer.

[134] The method of claim 133, wherein the confluent monolayer is at least 90% confluent.

[135] The method of claim 133 or 134, wherein the confluent monolayer is about 90%-100% confluent.

[136] The method of any one of claims 116-135, wherein the period of time to obtain a monolayer is at least 24 h.

[137] The method of any one of claims 116-136, wherein the period of time to obtain a monolayer is about 24 h to 5 days.

[138] The method of any one of claims 116-137, wherein the human plasma is newborn or adult plasma.

[139] The method of claim 138, wherein the human plasma is not heat inactivated.

[140] The method of claim 138, wherein the human plasma is heat inactivated.

[141] The method of any one of claims 138-140, wherein the human plasma is plasma pooled from more than one donor.

[142] The method of any one of claims 138-141, wherein the human newborn plasma is obtained from human umbilical cord blood.

[143] The method of any one of claims 138-142, wherein the human plasma has been previously been cryopreserved.

[144] The method of any one of claims 116-143, wherein the human plasma is used at at least 40%.

[145] The method of any one of claims 116-144, wherein the human plasma is used at about 40%-100%.

[146] The method of any one of claims 116-145, wherein the human plasma is used at about 50%.

[147] The method of any one of claims 116-146, wherein the human MCs are newborn or adult mononuclear cells.

[148] The method of any one of claims 116-147, wherein the human MCs are derived from one donor.

[149] The method of any one of claims 116-148, wherein the human MCs are not pooled from more than one donor.

[150] The method of any one of claims 116-149, wherein the human MCs are cells previously cryopreserved.

[151] The method of any one of claims 147-150, wherein the human newborn MCs are obtained from human umbilical cord blood.

[152] The method of any one of claims 116-151, wherein the human MCs are human CD 33+ and/or CD14+ monocytes.

[153] The method of claim 152, wherein the human CD 33+ and/or CD14+ monocytes are from one donor.

[154] The method of claim 152, wherein the human CD 33+ and/or CD14+ monocytes are not pooled from more than one donor.

[155] The method of any one of claims 152-154, wherein the human newborn CD 33+ and/or CD14+ monocytes are obtained from human umbilical cord blood.

[156] The method of any one of claims 116-155, wherein the human MCs are cultured in the presence of human serum albumin.

[157] The method of claim 156, wherein the human serum albumin is not heat inactivated.

[158] The method of claim 155 or 156, wherein the human serum albumin is pyrogen-free.

[159] The method of any one of claims 155-158, wherein the human serum albumin is clinical grade human serum albumin.

[160] The method of any one of claims 116-159, wherein the human MCs are not cultured in the presence of exogenous cytokines or immune response stimulating agent.

[161] The method of any one of claims 116-160, wherein the human MCs are not cultured in the presence of GM-CSF.

[162] The method of any one of claims 116-161, wherein the human MCs are not cultured in the presence of IL-4.

[163] The method of any one of claims 116-162, wherein the period of time sufficient to allow the human MCs to autonomously extravasate through the monolayer of endothelial cells and colonize the cushion of extracellular matrix is at least 0.5 h.

[164] The method of any one of claims 116-163, wherein the period of time sufficient to allow the MCs to autonomously extravasate through the monolayer of endothelial cells and colonize the cushion of extracellular matrix is about 0.5 h to 4 h.

[165] The method of any one of claims 116-164, wherein the period of time sufficient to allow the human MCs to autonomously extravasate through the monolayer of endothelial cells and colonize the cushion of extracellular matrix is about 1.5 h to 2 h.

[166] The method of any one of claims 116-165, wherein the human plasma is intact plasma.

[167] The method of any one of claims 116-166, wherein the intact human plasma has not been depleted of platelets.

[168] A tissue construct produced according to the method according to claims 116-167.

[169] A tissue construct comprising:
 (a) a cushion of extracellular matrix;
 (b) a monolayer human endothelial cells on the top of the cushion; and
 (c) human mononuclear cells that have extravasated through the monolayer of human endothelial cells and are embedded and colonized the cushion of extracellular matrix.

[170] The tissue construct of claim 169, wherein the collagen is human collagen.

[171] The tissue construct of claim 170, wherein the human collagen is Type I.

[172] The tissue construct of claim 171, wherein the human collagen is glycated.

[173] A kit comprising:
 (a) a tissue culture well;
 (b) an extracellular matrix comprising collagen; and
 (c) glucose-6-phosphate.

[174] The kit of claim 173, further comprising human primary endothelial cells.

[175] The kit of claim 174, further comprising human plasma which can be newborn or adult.

[176] The kit of claim 175, further comprising human serum albumin.

[177] The kit of claim 176, wherein the human plasma is not heat inactivated.

[178] The kit of claim 176, wherein the human plasma is heat inactivated.

[179] The kit of claim 176, wherein the human plasma is plasma pooled from more than one newborn.

[180] The kit of claim 176, wherein the human plasma has been previously been cryopreserved.

[181] The kit of claim 175, wherein the human serum albumin is not heat inactivated.

[182] The kit of claim 175, wherein the human serum albumin is pyrogen-free.

[183] The kit of claim 173, comprising the extracellular matrix is human collagen.

[183] The kit of claim 183, wherein the human collagen is Type I.

[185] The apparatus of claim 184, wherein the human collagen is glycated.

[186] A method of preparing matured collagen comprising incubating collagen with glucose-6-phosphate for a period of time sufficient for effectuating glycosylation of the collagen.

[187] The method of claim 186, wherein the collagen is human collagen.

[188] The method of claim 187, wherein the human collagen is Type I.

[189] The method of claim 186, wherein the period of time sufficient for effectuating glycation of the collagen is at least 48 h.

[190] The method of claim 186, wherein the period of time sufficient for effectuating glycation of the collagen at least 48 h and up to 5 days, from 2-5 days, from 2-3 days, from 2-4 days, from 3-4 days, from 4-5 days, or from 3-5 days.

[191] A matured collagen prepared according the method of claims 186-190.

[192] A matured collagen of claim 191, wherein the collagen is glycated.

The embodiments of the tissue constructs and methods are further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

Example

Materials and Methods

Abbreviations used in this study are found in Table 1.

Vaccines

Vaccines employed in the exemplary study included 13 valent pneumococcal conjugate vaccine (PCV) PREVNAR13™ (Wyeth Pharmaceuticals Inc., Philadelphia, Pa.), hepatitis B vaccine (HBV) was RECOMBIVAX® (Merck & Co., Inc.; Whitehouse Station, N.J.), diphtheria, tetanus and acellular pertussis (DTaP; TRIPEDIA®, Sanofi Pasteur Inc.; Swiftwater, Pa.), EASYFIVE® (a combination of five vaccines: diptheria, tetanus, whole cell pertussis, hepatitis B (rDNA), and *haemophilus* Type b conjugate vaccine; Panacea Biotec Ltd., India), and BCG (*Mycobacterium bovis* Danish strain 1331; Statens Serum Institut, Copenhagen, Denmark). Vaccines were administered to adult tissue cultures (ATCs) and neonatal tissue cultures (NTCs) at doses of 1:10 or 1:100 (vol/vol) by dilution in autologous plasma autologous plasma. Known newborn vaccines are shown in Table 2.

Adjuvants

Aluminum hydroxide (Statens Serum Institut; Copenhagen, Denmark) was administered to the ATC or NTC with a dose of 5 µg/µL or 50 µg/µL. Aluminum hydroxide was diluted with platelet poor plasma (PPP) autologous plasma. Toll-like receptors (TLR) agonists employed in this study included $Pam_3CysK_4$ (TLR2; InVivogen) studied at 10 µg/µL, as well as the imidazoquinolines R848 (Resiquimod; TLR7/8) and 3M-002 (TLR8/7; 3M Pharmaceuticals, St Paul, Minn.) studied at 5 and 50 µM. NTCs and ATCs were stimulated with adjuvants for 48 hours prior to harvesting reverse transmigratory leukocytes and conditioned media.

Endotoxin Testing

Endotoxin contamination was excluded by Kinetic turbidimetric (KTA) LAL using the KTA2 reagent (Charles River Laboratories International, Inc., Wilmington, Mass.). All reagents used in this study contained <0.2 EU/μL.

Blood

Adult blood was collected by a single peripheral venipuncture in increments of 200-300 mL from adults ranging in age of 26 to 45 years of age that were currently not infected with any acute or chronic pathogens. Cord blood was collected from umbilical cords and placentas delivered via cesarean section. Births to mothers known to have fever, acute or chronic infections, or HIV infection were excluded from the study.

Plasma

Plasma was harvested from whole blood fractions by centrifugation of fresh blood at 0.5 relative centrifugal force (RCF) for 10 minutes at room temperature. Plasma was separated from the cellular fraction and was subsequently centrifuged again for 30 minutes at 3.0 RCF at room temperature. The clear plasma from this centrifugation (platelet-poor plasma; PPP) was stored at −20° C. until thawed for use on TCs. To remove any debris after thaw, plasma samples were centrifuged at 3.0 RCF for 30 min and the supernatants added used for TCs.

Mononuclear Cell (MC) Isolation and Cryopreservation

Cellular fractions in the pellet from plasma preparation were used for mononuclear cell isolation by Ficoll density gradient separation. 15 mL FICOLL-PAQUE™ PREMIUM (1.077±0.001 g/ml) was layered on top of sterile ACCUSPIN™ (SIGMA ALDRICH®, St. Louis, Mo.) conical tubes and spun at 0.8 RCF for 30 seconds. Adult peripheral blood or cord blood was resuspended with an equal volume of 1×DPBS (GIBCO®, Carlsbad, Calif.) to the amount of plasma harvested from the blood. This resuspended blood cell fraction was layered on top of the ACCUSPIN™ tubes and centrifuged at 0.5 RCF for 30 minutes. The MCs were taken from the middle buffy coat layer of the FICOLL density gradient. These cells were washed twice with 1×DPBS (GIBCO®, Carlsbad, Calif.) and counted for viability using Trypan blue (0.2%) (SIGMA ALDRICH®, St. Louis, Mo.) by means of a hemocytometer. Viable cells were cryopreserved in 10% DMSO (SIGMA ALDRICH®, St. Louis, Mo.), and 90% autologous PPP at a viable MC concentration of $100 \times 10^6$ in 1 mL of solution in cryogenic 1.8 mL tubes (Nunc; Rochester, N.Y.). These tubes were placed into a cryopreservation container ("Mr. Frosty", Nalgene; ThermoFisher Scientific Rochester, N.Y.) then at −80° C. for 24 hours prior to storage in the gas phase of a liquid nitrogen storage tank until use for TC colonization.

CD 33+ Monocytes (Mos) and Naïve CD4+ Isolation

Cryopreserved MCs were thawed and washed with 1×DPBS (GIBCO®, Carlsbad, Calif.). Viable MCs were then counted using Trypan blue exclusion (0.2%, SIGMA ALDRICH®; St. Louis, Mo.). Viable MCs were then labeled with anti-CD 33 magnetic microbeads (MACS, Miltenyi Biotech GmbH, Bergisch Gladbach, FRG) for 15 minutes, washed and then passed over a magnetic LS column (MACS, Miltenyi Biotech GmbH, Bergisch Gladbach, FRG) for positive selection of CD 33+ cells. CD 33+ cells were then washed with 1×DPBS (GIBCO®, Carlsbad, Calif.) to remove any residual microbeads and viable CD 33+ cells were counted using Trypan blue (0.2%) exclusion. Viable CD 33+ cells were then added to TCs as described below. Alternatively, cryopreserved MCs were thawed and washed with 1×DPBS (GIBCO®, Carlsbad, Calif.). Viable MCs were counted by Trypan blue exclusion then labeled with MACS® Naïve CD4+ T Cell Isolation Kit II (Miltenyi). CD4+ Naïve T-cells were negatively selected on an LS magnetic column (Miltenyi), washed with 1×DPBS, and viable cells enumerated using Trypan blue exclusion prior to culture.

Tissue Constructs (TCs)

Human umbilical vein endothelial cells (HUVEC) (Lonza, Walkersville, Md. USA) were grown using M199 (INVITROGEN™ Carlsbad, Calif.) containing 1% penicillin/streptomycin/L-glutamine (PSG) (100× Stock) (INVITROGEN™ Carlsbad, Calif.) and 50% defined fetal bovine serum (FBS) (Hyclone, Logan, Utah) in a 5% $CO^2$ incubator at 37° C. HUVECs were derived from a single donor and were grown to confluency in a T-75 flask, then a T-150 flask prior to seeding them onto TCs. Media were changed every 2nd day and passages were performed using 0.25% Trypsin with EDTA (INVITROGEN™ Carlsbad, Calif.). Approximately $10^5$ cells/cm$^2$ (32,000 HUVECs/well) were seeded on top of a pre-cast extracellular matrix gel in a flat-bottom 96-well plate. The extracellular matrix gel was cast using PURECOL® ® as per the manufacturer's recommendation (Advanced Biomatrix, San Diego, Calif.) using a 8:1:5 ratio of Type 1 Collagen (PURECOL® or VITRACOL®), 10×M199 (INVITROGEN™ Carlsbad, Calif.), and 0.1N NaOH added in order, respectively. Alternatively, human extracellular matrix gels were formed using VITRACOL® cast by manufacturer's recommendations (Advanced Biomatrix, San Diego, Calif.) as described above. Human extracellular matrix gels were modified using 225 mM neutralized (pH 7.0) Glucose-6-Phosphate (SIGMA ALDRICH® St. Louis, Mo.) for 5 days prior to use for HUVEC culture. HUVECs were allowed to grow to 95-100% confluency on the extracellular matrix (~5 days for bovine or 1 day for human matrices) in the presence of M199 (INVITROGEN™ Carlsbad, Calif.) containing 1% penicillin/streptomycin/L-glutamine (PSG) (100× Stock) (INVITROGEN™ Carlsbad, Calif.) and 50% FBS (only for TCs not used for CD 33+ monocytes-dendritic cell (MoDC)-lymphocyte co-culture) or 50% pooled heat-inactivated newborn PPP (only for completely human TCs used for MoDC-lymphocyte co-culture studies) in a 5% $CO_2$ incubator at 37° C. Confluent TCs were then used for the extravasation of thawed cryopreserved MCs or CD 33+ Mos. Thawed MCs were washed with 1×DPBS and counted using Trypan blue exclusion. $5 \times 10^5$ viable MCs were added to each TC well for extravasation. Freshly isolated CD 33+ Mos were added at $10^5$ Mos/TC well. Extravasation occurred during 1.5 hr incubation under serum-free conditions with M199 (INVITROGEN™ Carlsbad, Calif.) containing 1% PSG (INVITROGEN™) and 0.1% Human Serum Albumin (Talecris Biotherapeutics; Clayton, N.C.). After extravasation, non-extravasated cells were washed off TCs using 1×DPBS (INVITROGEN™).

DC Generation and Maturation of Migratory RT-APCs and Matrix Resident Leukocytes Colonized TCs were cultured with 100% autologous plasma alone (unstimulated control) or autologous plasma containing a stimulant (eg, adjuvant or vaccine). Stimulation occurred during a 48 hr incubation at 37° C./5% $CO_2$, after which conditioned media was carefully removed from the top of the liquid phase and stored at −20° C. Reverse transmigrated antigen presenting cells (RT-APCs) were harvested off the top of TCs and pooled into a 5 mL round-bottom tube. Viable pooled RT-APCs were enumerated by Trypan blue exclusion, stained for flow cytometry, and stained for confocal microscopy. Harvested TCs were fixed with 10% paraformaldehyde (Electron Microscopy Sciences, Hatfield, Pa.) and stored at 4° C. prior to hematoxylin and eosin (H&E) staining. Phenotyping of extravasated and matrix-resident cells employed 15 min treatment with 50 μL collagenase (Liberase; DL Research Grade; ROCHE®, Indianapolis, Ind.). The liquefied ECM was then harvested separately from the HUVEC monolayer and pooled for flow cytometry staining. This technique was also used for counting of extravasated and resident cells using Trypan blue exclusion.

Flow Cytometry

Immunophenotyping of TC-derived leukocytes employed 6 to 7 color flow cytometry using a Beckman Coulter MoFlo Legacy with Coherent Sapphire 488 nm, Dako red diode 635 nm, Coherent Radius 405 nm lasers and Beckman Coulter Summit v4.3 software. Cells were stained with conjugated Abs at a concentration recommended by manufacturer's specifications. Abs used included: CD14-APC-Cy7, HLA-DR-PE-Cy7, CD16-PE, CD3-APC, CD19-PerCP-Cy5.5, CD123-FITC, CD45RO-PE-Cy7, CD45RA-FITC, CD56-APC, CD8-PE, HLA-DR-PerCP-Cy5.5 (Becton, Dickinson and Company, Franklin Lakes, N.J.). Corresponding isotype control antibodies (Abs) were used in each experiment to determine non-specific binding according to manufacturer's specifications (Becton, Dickinson and Company). Compensation employed ABC™ anti-Mouse Bead Kit (Molecular Probes, Inc. Eugene, Oreg.) bound to the above Abs for each color in the profile as per the manufacturer's recommendations. Staining of leukocytes employed incubation with Abs for 30 min, centrifugation (10 min), washing with 1×DPBS, prior to fixing with 4% paraformaldahyde. Flow cytometry data was acquired using the above MOFLO Legacy system and analyzed using FLOWJO software (Tree Star, Inc. Ashland, Oreg.). Mature DCs were defined as $CD14^{lo}$, $HLA-DR^{hi}$, CCR7+, CD86+ or CD83+ cells.

Cell Viability and Reverse Transmigration (RT) Index

Cell viability was determined via Trypan Blue exclusion on a Nikon TS100 inverted microscope at 10× objective. Using a hemocytometer and 0.2% Trypan blue cells were diluted in a 1:1, 1:5, 1:10, or 1:100 dilution in order to count ~50-150 cells/quadrant. Viable cells were identified by a lack of Trypan blue staining. Dead cells were also counted to obtain total cell counts and % viability. Viable total cell counts were used in conjunction with flow cytometry analyses to determine percent of total cell types (e.g., CD14+ cells) that reverse transmigrated to the luminal compartment.

Endothelial Integrity

Endothelial monolayers of TCs were evaluated by fixing the endothelial layers on top of the collagen cushions with a 10% paraformaldehyde solution. Fixed cushions were stained with hematoxylin and eosin Y per the manufacturer's directions (VWR International, LLC). Cushions were imaged on a Nikon TS100 inverted microscope using the 10× objective (Nikon Instruments Inc., Melville, N.Y.). Endothelial layers were examined for monolayer integrity and cell morphology to assess whether added stimuli resulted in cell activation.

Initial Cell-Migration Index and Cell-Retention Index

TCs were fixed and stained using hematoxylin/eosin as described above, then mounted on glass slides for imaging. Stained cushions were imaged using bright-field microscopy (TE2000 microscope, Nikon Instruments Inc.; Melville, N.Y.) using the 20× objective and software-based image acquisition (Slidebook software; Denver, Colo.). Each condition was imaged by taking five individual stacks of images ranging in 300 μM in length at 30, 10 μM increments. Three cushions were imaged per condition. The resulting stacks of images were processed using ImageJ software by converting them to 8-bit grayscale images and using a threshold setting in order to acquire stained cells. Images were then used to count the number of stained cells that remained inside the cushions. To avoid counting debris, only objects with a diameter in the 25-135 μm and only cells that fell within a standard deviation of the mean size were counted. Cells falling between the standard deviations of the individual counts were then used as normalized counts. Initial cell migration index was determined by counting the number of PBMCs, CMBCs, or CD 33+ Mos that had migrated into TC matrices after the initial 1.5 hr migration. The cell-retention index was determined by counting retained MCs that had not reverse transmigrated during the subsequent 48 hr stimulation.

Confocal Microscopy

For confocal microscopy, reverse transmigrated cells were harvested and seeded onto BD BIOCOAT™ round Poly-L-Lysine Coated Glass Coverslips (12-mm diameter) in a 24-well, flat-bottom, tissue-culture plate (Falcon, Becton Dickinson, Franklin Lakes, N.J., USA). Warmed NTC plates were rapidly processed by gently resuspending the media of each TC well, taking ~70 μi/well from 5-10 TC wells per condition and transferring these to a coverslip circle (total volume ~350-700 μL). Pooled reverse transmigrated antigen presenting cells (RT-APCs) (aka reverse transmigrated dendritic cells) were split to test for isotype control Abs and test Abs. RT-APCs were incubated in 24-well plates at 37° C./5% $CO_2$ for 30-60 min to allow cells to settle and attach. Attached cells were washed with 1×DPBS, then fixed/permeabilized using BD CITOFIX/ CYTOPERM™ (Becton, Dickinson and Company) followed by incubation at 37° C. for 10 min. Subsequent washes employed BD Washing Buffer. 500 μL/well of DPBS/0.5% human serum albumin was added to each well, then 20 μL HLA-DR-FITC conjugated Ab (Becton, Dickinson and Company), 1 μL DRAQ5™ dye (eBiosciences, Inc.; San Diego, Calif.), and 2.5 μL of ALEXA FLUOR® 594 phalloidin F-actin stain (Molecular Probes, Inc.; Eugene, Oreg.) were added to each well. Corresponding isotype control Abs were added to negative control wells. Cells were stained in the dark at 37° C. for 30-60 min. Mounting employed 50% glycerol 50% DPBS. Images were acquired using SLIDEBOOK™ software on a fluorescent microscope (AXIOVERT 200m fluorescent microscope, ZEISS®; Thornwood, N.Y.).

Multiplex Cytokine Analyses

Conditioned media post 48 h culture on top of TCs was used to analyze cytokine profiles. Cytokines were measured using a fluorometric bead-based multiplex assay according to the manufacturer's instructions (MILLIPLEX™ MAP 26-plex Human Cytokine/Chemokine panel, MILLIPORE®; Billerica, Mass.). All conditioned media was tested at neat concentrations after a single freeze-thaw cycle.

Co-Culture of DCs with Autologous Naïve CD4+ Lymphocytes

For experiments whose endpoints included MoDC-lymphocyte co-culture, CD33+ Mo-colonized TCs were employed. Viable RT-APCs (trypan) from unstimulated or vaccine-stimulated CD33+ Mo-colonized TCs were added to fresh, negatively-selected autologous CD4+ CD45RA+ Naïve T cells at a ratio of 1 RT-APC to 10 CD4+ CD45RA+ Naïve T cells. RT-APCs and Naïve CD4+ T-cells were co-cultured in 200 μL of RPMI Medium 1640 (INVITROGEN™; Carlsbad, Calif.) containing 10% autologous plasma in round-bottom 96-well plates. Co-cultures were maintained for 7 days for primary responses at 37° C./5%

CO$_2$. Half of the media was replaced every 3rd day and stored at −20° C. for cytokine analysis. In experiments measuring secondary responses, co-cultures were allowed to rest up to 20 days prior to re-stimulation of T-cells with newly harvested RT-APCs from secondary TCs. For some experiments comparing BCG, PCV and HBV, vaccines were administered relative to the volumes used for clinical dosing in vivo. For example, as the volume dose of BCG (0.05 mL) is 10 fold less than that of PCV (0.5 mL), we administered 10-fold less BCG vol/vol—e.g., 1:20 dilution BCG vs. 1:2 dilution of PCV.

H$^3$-Thymidine Incorporation Assays: Co-cultures of RT-APCs and naïve CD4+ cells were maintained for the desired time at which point 1 μCi of H$^3$-Thymidine (PERKINELMER®; Waltham, Mass.) was added to each well and incubated for 18 hrs prior to cell harvest (HARVESTER96™, TomTec; Hamden, Conn.) onto glass fibre filter mats (PERKINELMER® Waltham, Mass.). Tritium was counted using a 1450 Microbeta (PERKINELMER® Waltham, Mass.). All conditions were studied in triplicate.

Results

Creation of Mononuclear Cell-Colonized Tissue Constructs.

TCs were created employing casted extracellular matrix cushions with an overlaying cultured confluent HUVEC monolayer, thereby modeling a microvascularized interstitium. The casted extracellular matrix (ECM) cushions comprised of human Type 1 Collagen and human fibronectin, prior to culturing HUVECs to confluence above these matrix cushions. Previously cryopreserved mononuclear cells (MCs) were allowed to extravasate inside the TCs. TCs autonomously generate antigen-presenting cells from extravasated monocytes. To develop NTCs and ATCs, CBMCs or PBMCs respectively, were allowed to extravasate and colonize TC matrices over 1.5 hrs (FIG. 1). After removal of non-migrated cells, autologous intact plasma was added to each TC with or without stimuli. TCs were then cultured for 48 hours at 37° C./5% CO$_2$ during which MC-derived APCs autonomously reverse transmigrated to the luminal TC compartment, differentiating into immature MoDCs.

Figure 2:
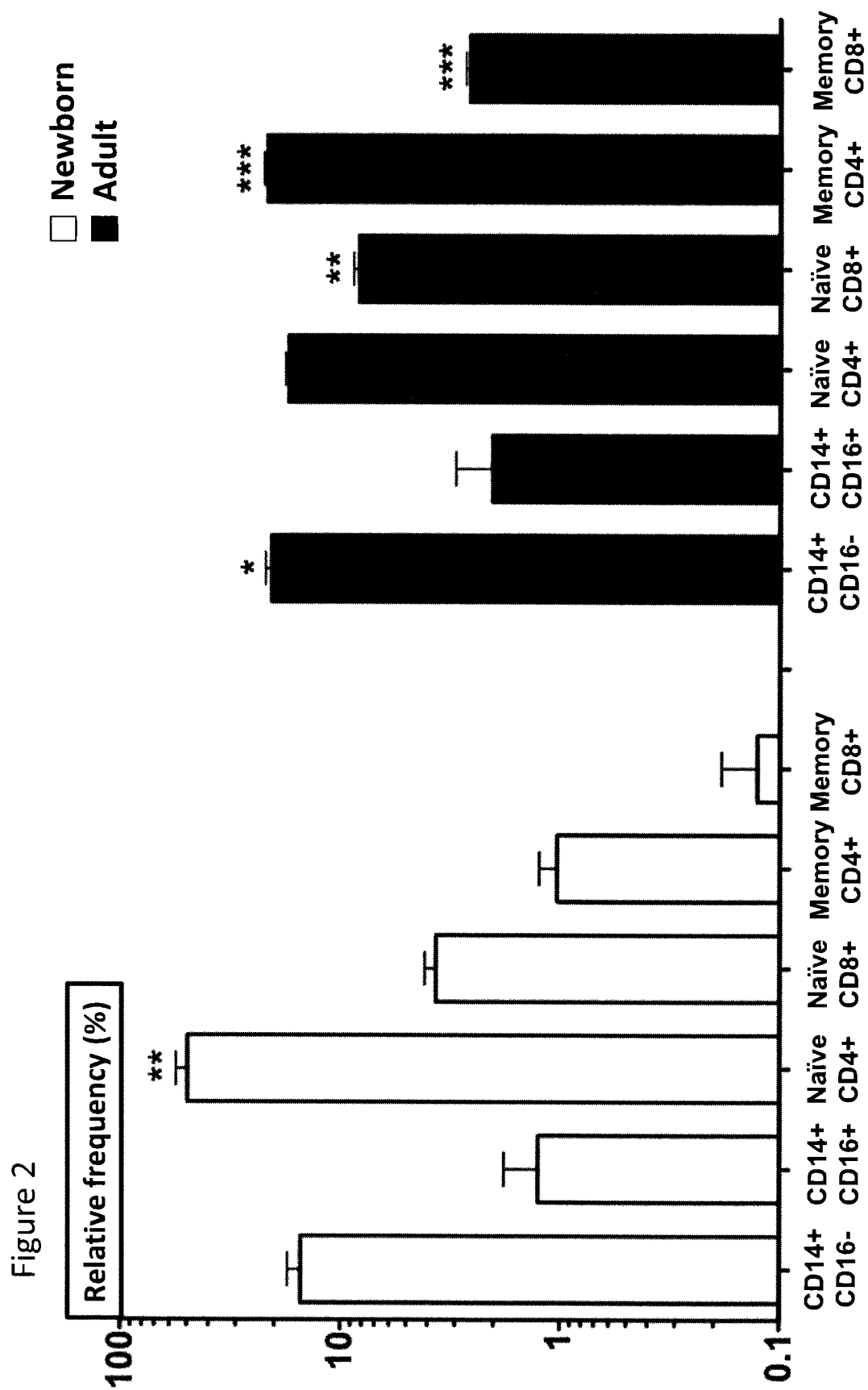
FIG. 2 shows histograms of the distinct proportion of different leukocytes in thawed neonatal cord blood mononuclear cell (CBMCs) and adult peripheral blood mononuclear cell (PBMCs). (N=3; 2-tailed T test; *, $p<0.05$, , $p<0.01$, *, $p<0.001$).
Figure 3:
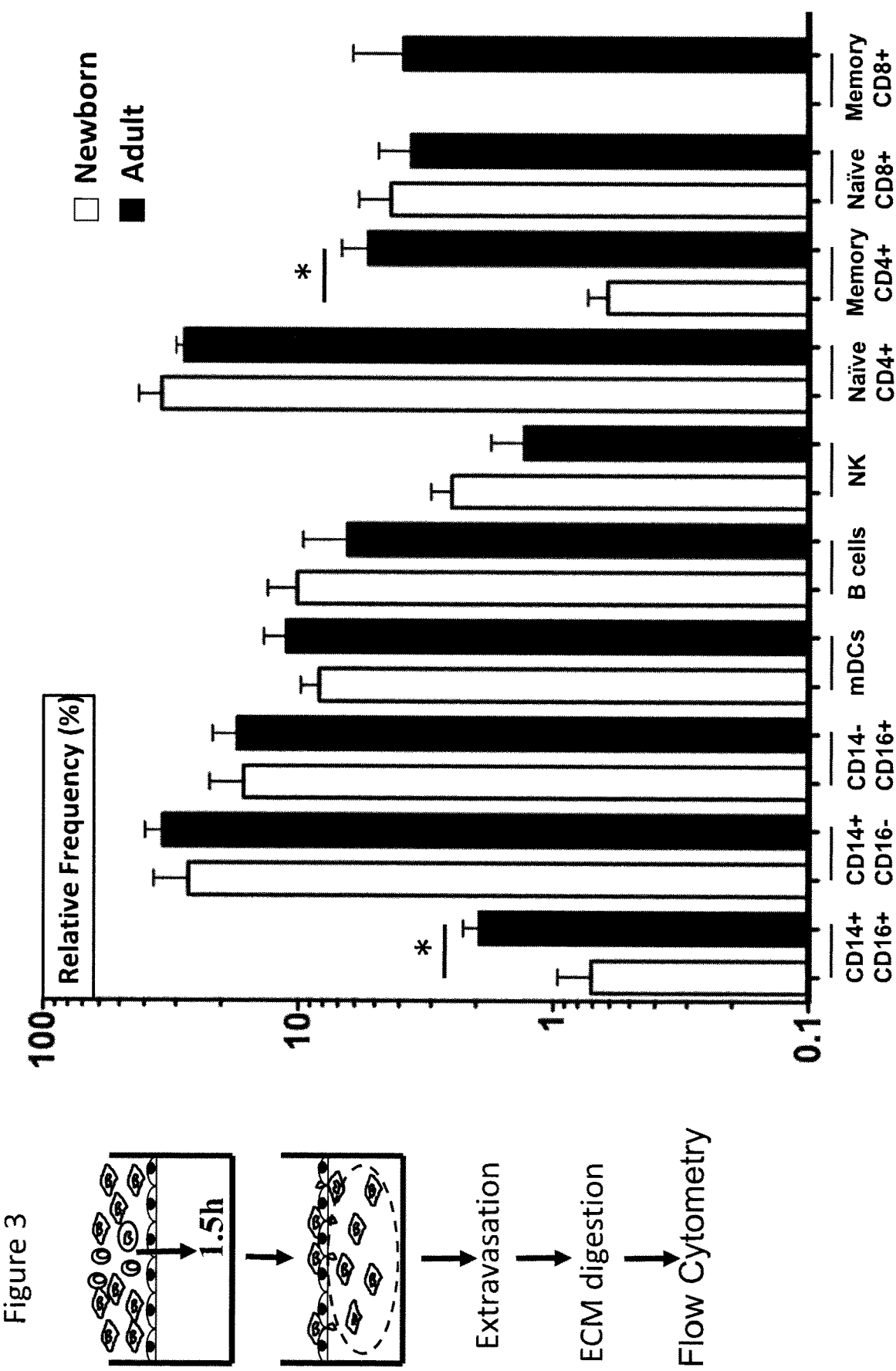
FIG. 3 shows histograms of the distinct population of TC-extravasated MCs having different cell-lineage as assessed by cell surface markers. (N=3, 2-tailed T test; * $p<0.05$).

CBMCs demonstrate impaired extravasation but robust reverse transmigration. As a first step in characterizing neonatal and adult leukocytes in TCs, the extraysation, TC-retention and reverse transmigration of CBMCs and PBMCs were compared. CBMCs contained a relatively high proportion of naïve CD4 T cells and a lower proportion of memory CD4 and CD8 T cells as compared to adult PBMCsAs, whereas adult PBMCs demonstrated greater proportions of CD14+ CD16-Mos, naïve CD8+ T cells and memory CD4+ and CD8+ T cells (FIG. 2). Comparison to clinical reference standards provided by the Children's Hospital Boston Core Lab indicated that cryopreservation did not modify the relative frequency of different MC types. Immunophenotyping of extravasated cells by flow cytometry revealed that NTCs had fewer CD14+ CD16+ Mos and fewer memory CD4+ T lymphocytes relative to ATCs (FIG. 3). As compared to extravasated MCs in adult TCs (ATCs), extravasated newborn MCs in neonatal (NTCs) demonstrate a relatively high proportion of naïve CD4+ T cells and a lower proportion of CD45RO+ memory T cells, CD14+ CD16+ Mos and plasmacytoid dendritic cells (DCs). Phenotype of migratory leukocytes was assessed by 7-color polychromatic flow cytometry as described in Methods section.

Figure 4:
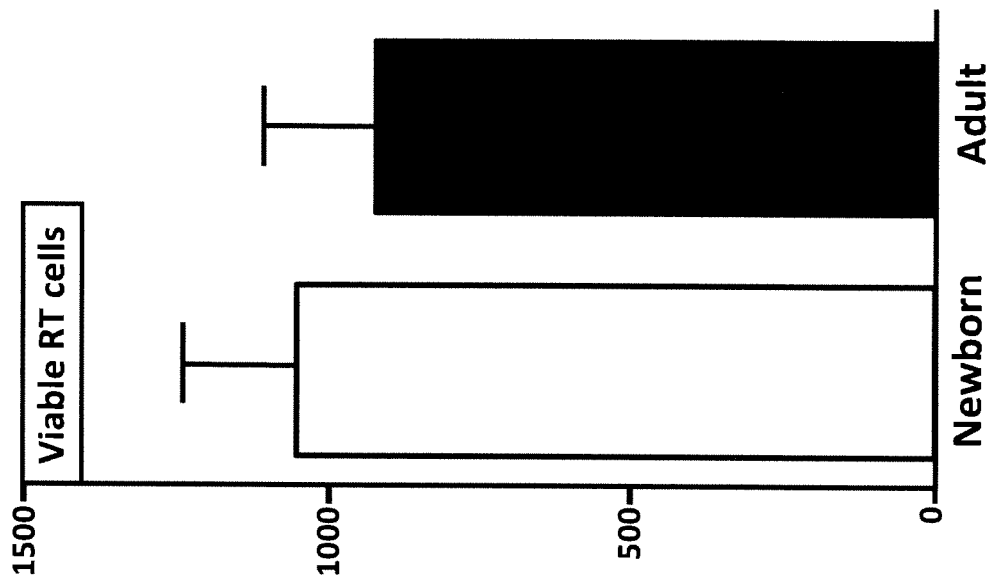
FIG. 4A shows that newborn CD14+ MCs demonstrate impaired extravasation into TCs as compared to adult MCs. (N=6; 2-tailed T test; * $p<0.05$).
FIG. 4B shows that despite lower extravasation of neonatal CD14+ MCs, neonatal tissue constructs (NTCs) and adult tissue constructs (ATCs) generated similar numbers of viable reverse transmigrated (RT) MCs after 48 hours of culture. (N=6; 2-tailed T test; * $p<0.05$).
Figure 4:
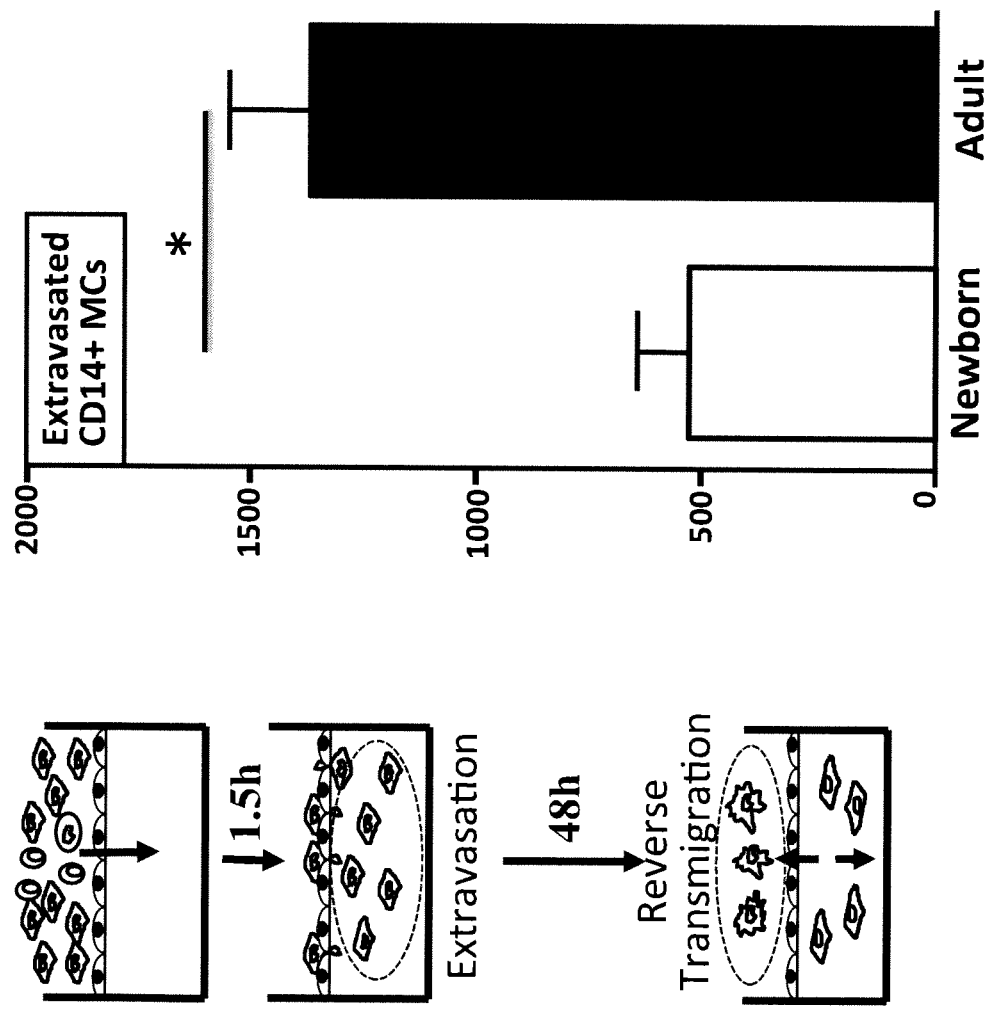

In comparing the overall ability of newborn CBMCs and adult PBMCs to colonize TCs, it was noted that CBMCs demonstrated a significantly lower number of extravasated CD14+ MCs than did PBMCs (FIG. 4A). Extravasated neonatal MCs demonstrated significantly lower number of CD14+ Mos than extravasated adult MCs in ATCs. Cell viability was determined by trypan blue exclusion and immunophenotype by polychromatic flow cytometry as described in Methods section.

Figure 5:
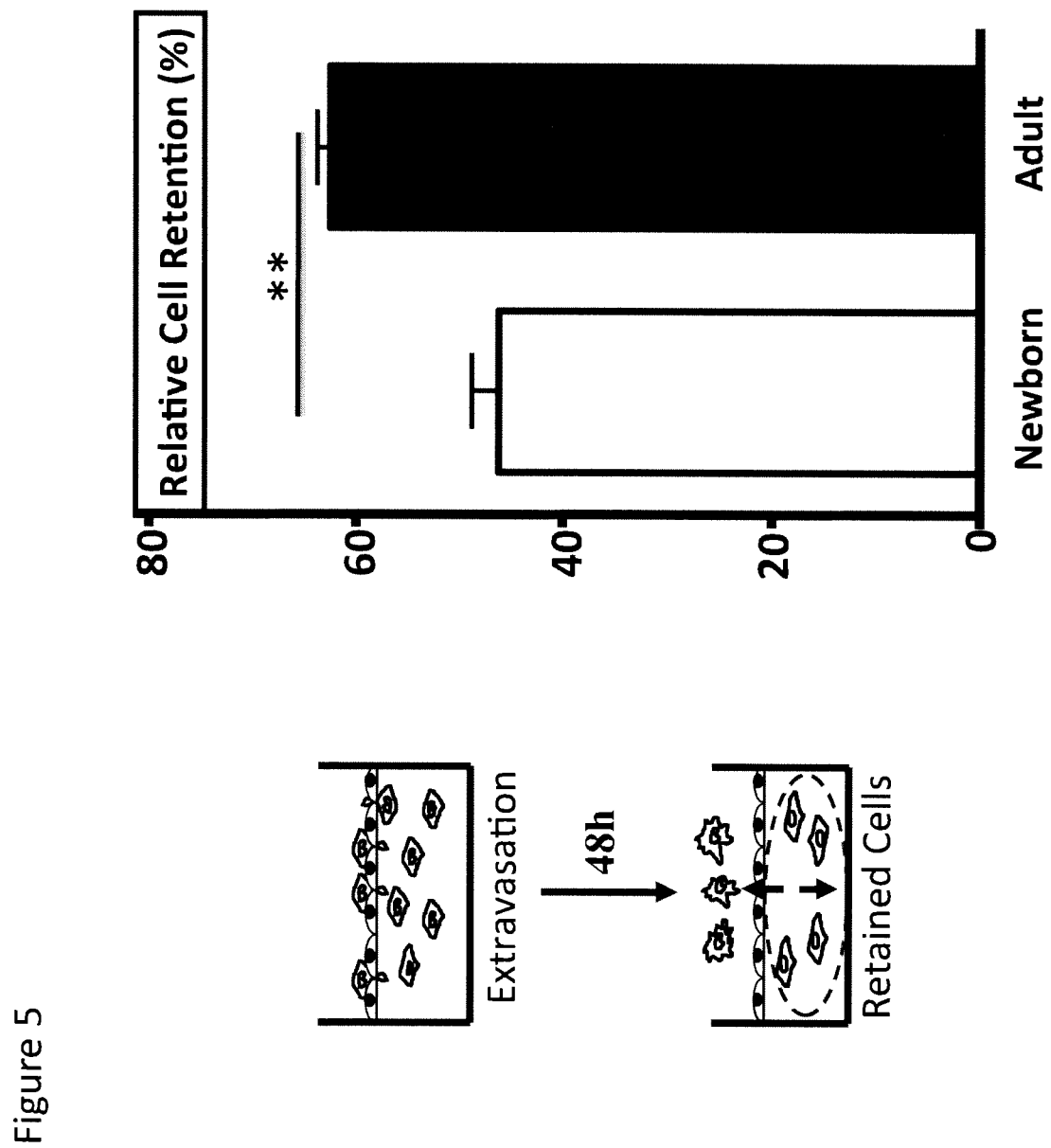
FIG. 5 shows the relative cell retention (%) inside the TCs compared between neonatal and adults MCs after 48 hr of culture. (N=3; 2-tailed T test; ** $p<0.01$).

Nevertheless, after 48 hours of culture, NTCs demonstrated similar numbers of reverse transmigrated cells (FIG. 4B), associated with significantly reduced leukocyte retention in the extracellular matrix compartment of the TC relative to ATCs (FIG. 5). FIG. 4B shows that despite lower extravasation of neonatal MCs, NTCs and ATCs generated similar numbers of reverse transmigrated (RT) MCs after 48 hours of culture, suggesting relatively reduced tissue residency of extravasated neonatal MCs with a robust capacity to traverse endothelium from the abluminal to luminal direction. FIG. 5 shows that after 48 hours of culture, reverse transmigrated cells were removed prior to fixing and staining TCs with hematoxylin and eosin. Cell density was assessed by microscopy and automated cell counting using ImageJ software. These observations indicate a preferential capacity of neonatal CBMCs to reverse migrate out of the TC matrix, traversing the endothelial layer from the abluminal to luminal direction.

Figure 6:
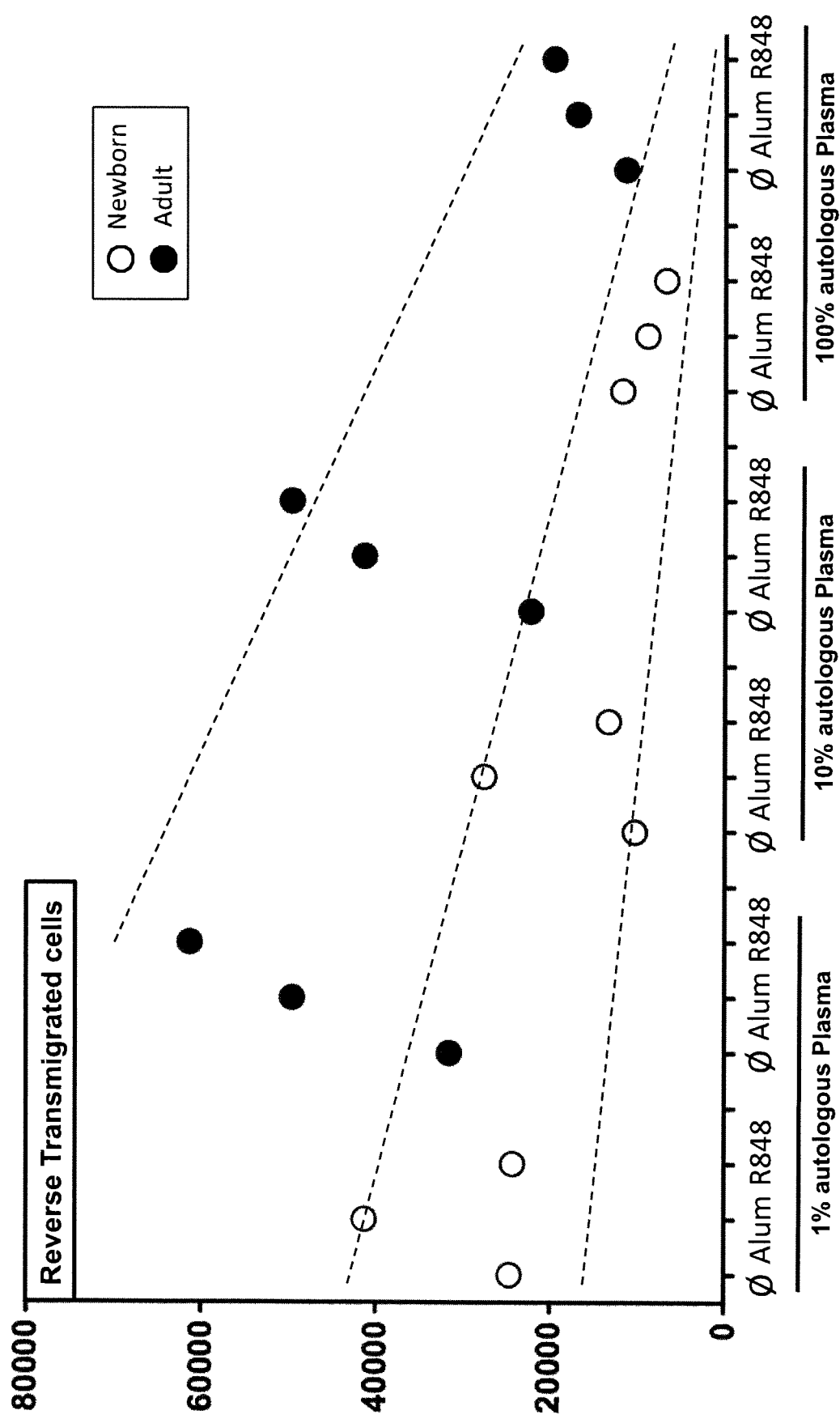
FIG. 6 shows the effects of increasing proportion of autologous plasma on reverse transmigration of leukocytes in TCs. TCs colonized by MCs were left untreated (0) or stimulated with Alum (50 μg/μL) or R848 (TLR7/8; 50 μM) in the presence of 1%, 10% or 100% (vol/vol) autologous plasma. (N=1).
Figure 7:
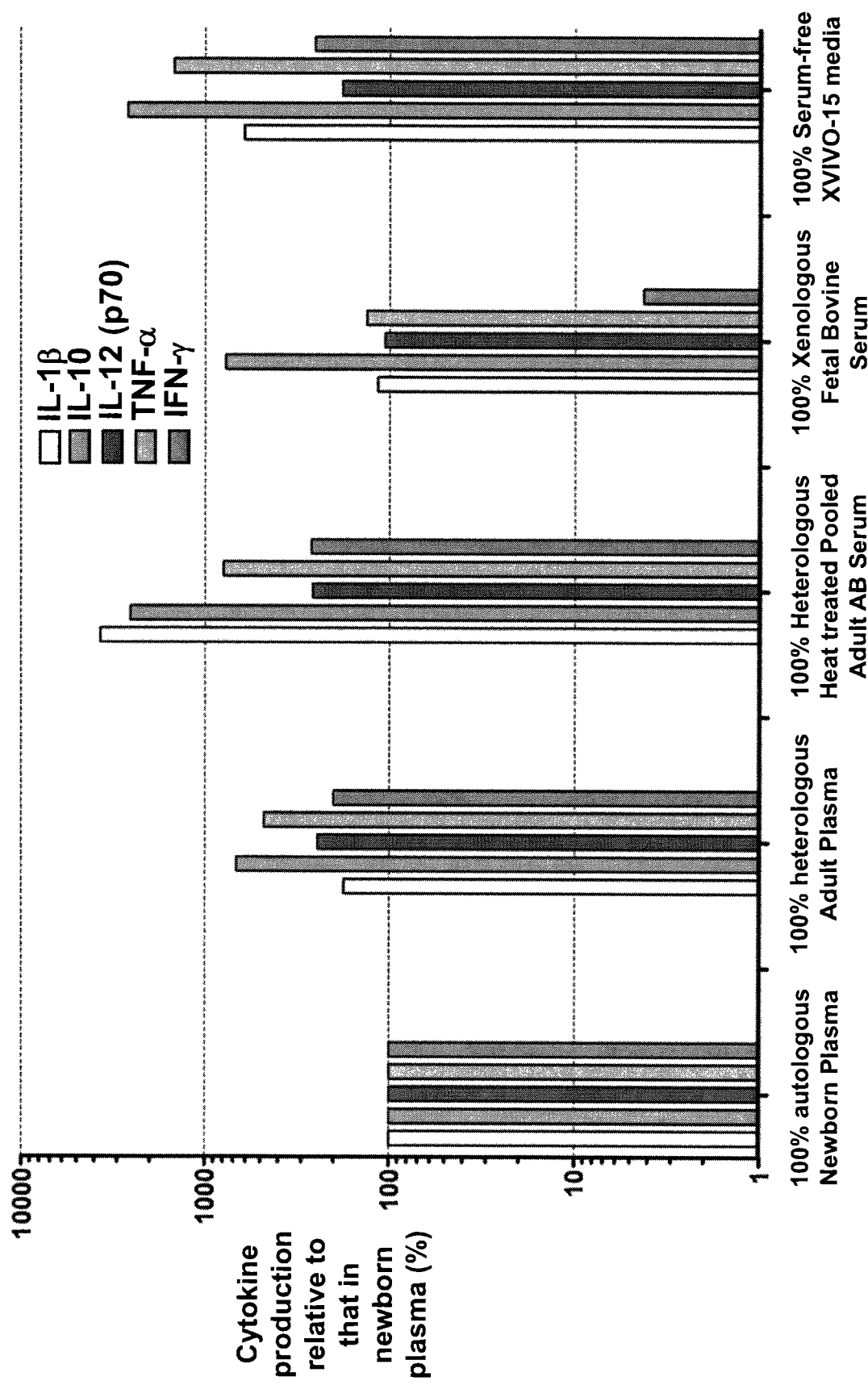
FIG. 7 shows that the types and quality of the fluid phase media have marked effects on TLR-mediated cytokine induction in an MC-colonized NTC. (N=1).

Extracellular media exert profound effects on MoDC migration and TC cytokine production. Soluble factors in neonatal blood plasma can modulate immune responses in whole blood [2, 6, 16], raising the possibility that extracellular media may also modulate leukocyte function in TCs. To this end, bioactivity of leukocytes in TCs cultured in different proportions of autologous plasma were compared. Increasing the proportion of neonatal or adult plasma in the extracellular medium from 1 to 10 to 100% (vol/vol) was associated with lower numbers of reverse transmigrated cells (FIG. 6). TCs colonized by MCs were left untreated (0) or stimulated with Alum (50 μg/μL) or R848 (TLR7/8; 50 μM) in the presence of 1%, 10% or 100% (vol/vol) autologous plasma. After 48 hours of culture, reverse transmigrated cells were harvested and counted using Trypan blue. Higher concentration of autologous plasma appeared to associate with the lower levels of reverse transmigration As another measure of the impact of fluid phase on leukocyte function, the impact of a variety of non-autologous media were assessed, as compared to autologous neonatal plasma, on TLR-mediated cytokine induction in the NTC (FIG. 7). MC-colonized NTC was stimulated TLR2-agonist Pam$_3$Cysk$_4$ (TLR2; 10 μg/μL) for 48 hours in 100% of autologous intact plasma, heterologous adult plasma, heterologous heat-treated pooled commercial adult AB serum, fetal bovine serum or serum-free commercial XVIVO-15 medium. Conditioned media were harvested and cytokine concentrations of IL-1B, IL-10, IL-12(p70), TNF-α and IFN-γ determined using a multiplex fluorescent bead-based array system. To highlight the change induced by non-autologous conditions, results were plotted as a percentage of that in autologous plasma. All non-microphysiological conditions increased the capacity of Pam$_3$Cysk$_4$ to induce cytokines. Non-autologous media conditions appeared to increase cytokine induction, except for fetal bovine serum that appeared to reduce IFN-γ. All non-microphysiological conditions increased the capacity of Pam$_3$Cysk$_4$ to induce cytokines. Non-autologous media conditions appeared to increase cytokine induction, except for fetal bovine serum that appeared to reduce IFN-γ. Accordingly, subsequent experiments employed autologous plasma conditions.

Figure 8:
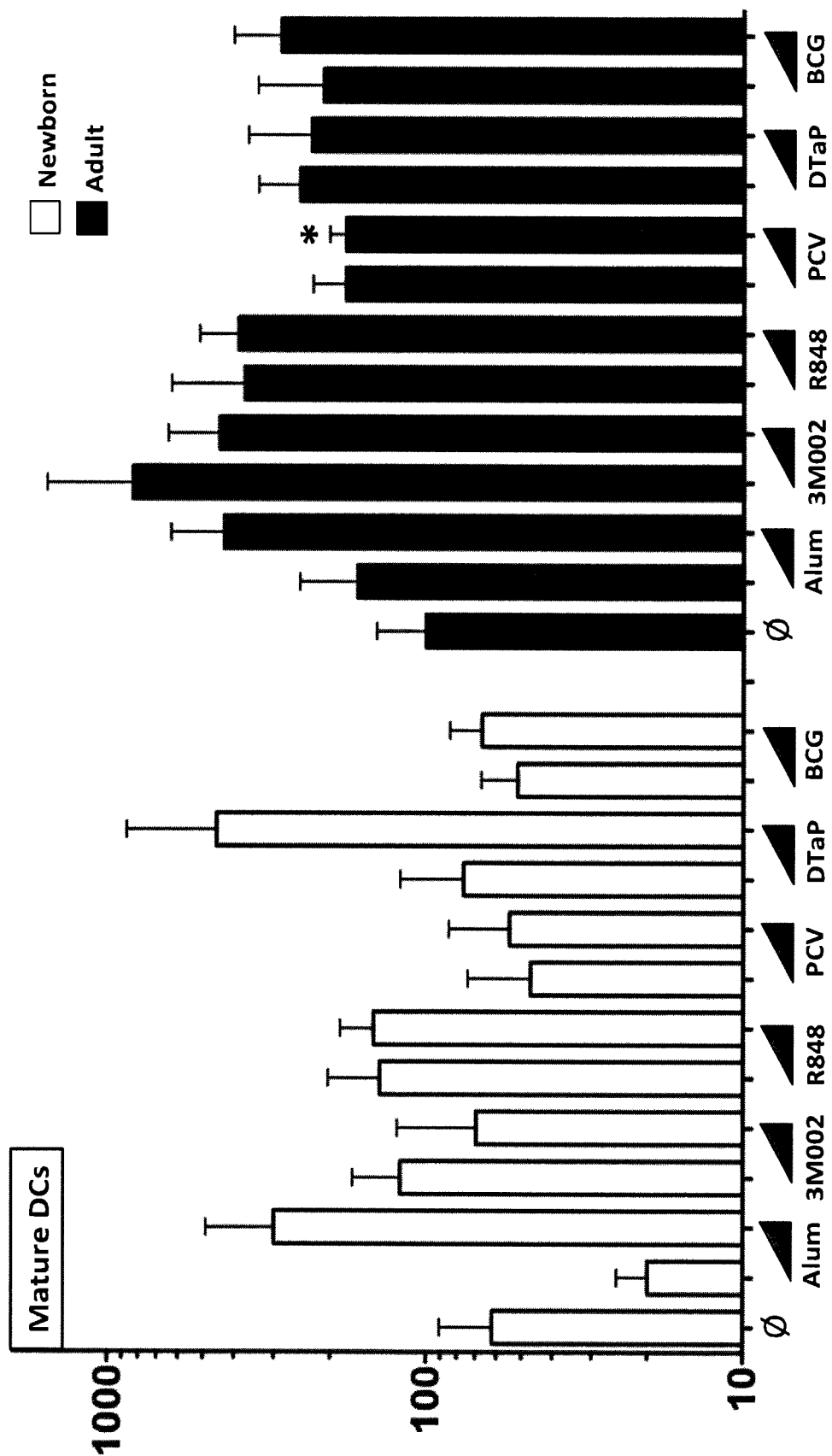
FIG. 8 shows that different doses of adjuvants and vaccines modulate the number of reverse transmigratory monocyte-derived dendritic cells (MoDCs) in tissue constructs. (N=3-4; 2-tailed T test; *, $p<0.05$, ** $p<0.01$).

MC-colonized TCs respond to adjuvants and vaccines. In seeking validation of the NTC model created here, the NTC were tested to evaluate whether the NTC can recapitulate known newborn immune responses to vaccines? To assess the ability of adjuvants and vaccines to induce maturation of TC-derived DCs, the common vaccine adjuvant Alum was compared with two TLR agonist candidate adjuvants: the small synthetic imidazoquinolines R-848 (TLR7/8) and 3M-002 (TLR8/7) as well as several approved vaccines routinely given to newborns (BCG) and infants (DTaP and PCV). BCG vaccine was chosen as a benchmark or reference to validate the NTC because BCG is administered as single dose, is safe, well tolerated and effective, newborn vaccine that is known to induce CD4+ T cell responses. All the adjuvants and vaccines tested appeared to increase the number of mature MoDCs from the NTC (FIG. 8). ATCs and NTCs were colonized with MCs and stimulated with the following adjuvants or vaccines: alum hydroxide (5 and 50 µg/µL); 3M-002 (TLR8/7; 5 and 50 µM); R848 (TLR7/8; 5 and 50 µM); PCV, DTaP and BCG vaccines (all at dilutions of 1:100 and 1:10 vol/vol). After 48 hrs of incubation, reverse transmigrated mature DCs were harvested and enumerated as described in Methods section. These studies revealed that adjuvants and vaccines can effect reverse transmigration of MoDCs from both NTCs and ATCs.

Figure 9:
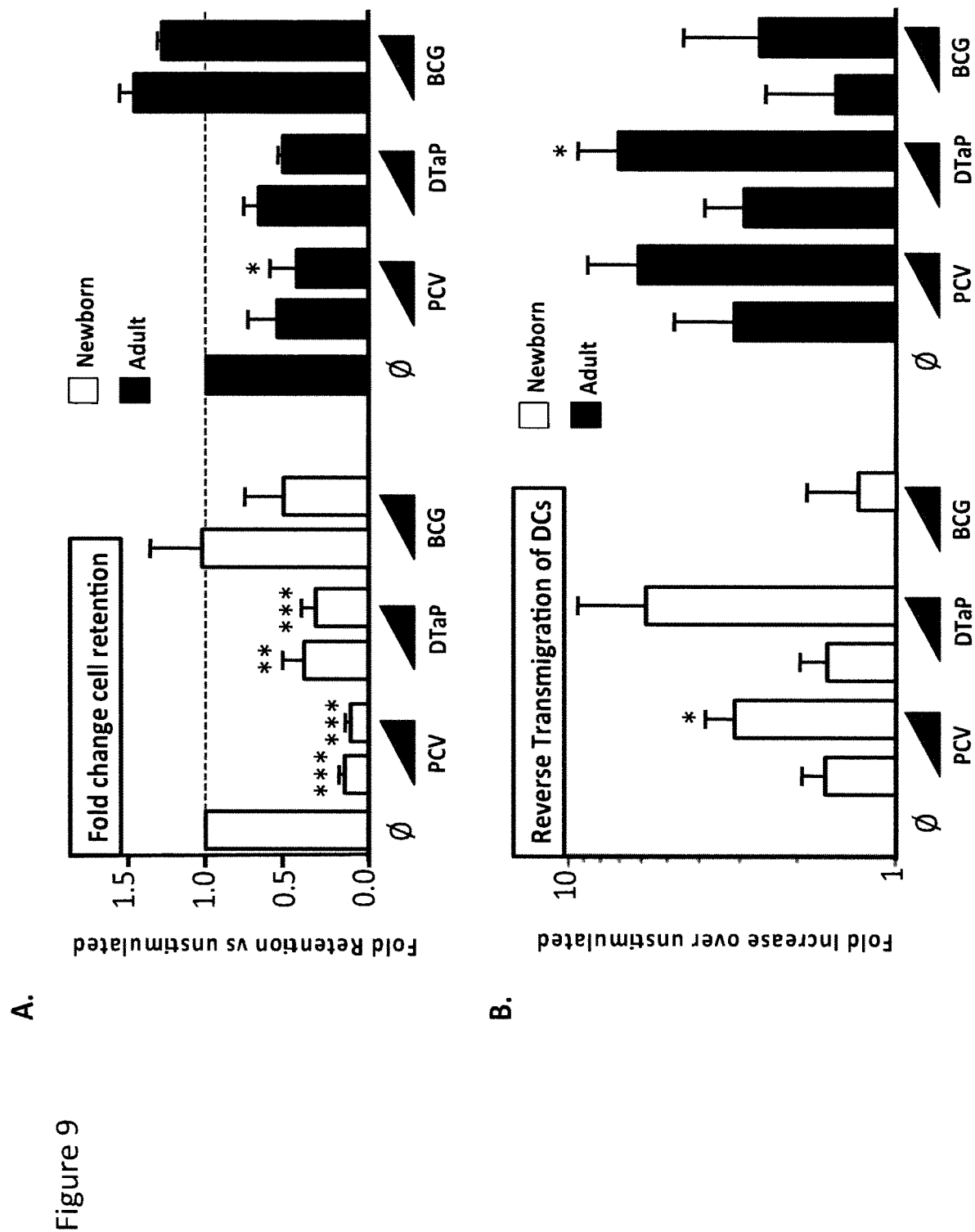
FIG. 9A shows the relative changes in cell retention in the tissue construct induced by different doses of vaccines in newborn and adults TCs. (N=2-4, 1-way ANOVA, Kruskal-Wallis test, Dunn's Multiple Comparison Test; * p<0.05,  p<0.01, * p<0.001).
FIG. 9B shows the relative changes on reverse transmigration of DCs induced by different doses of vaccines in newborn and adults TCs. (N=2-3; 1-way repeated measures-ANOVA, * p<0.05,  p<0.01, * p<0.001).
Figure 10:
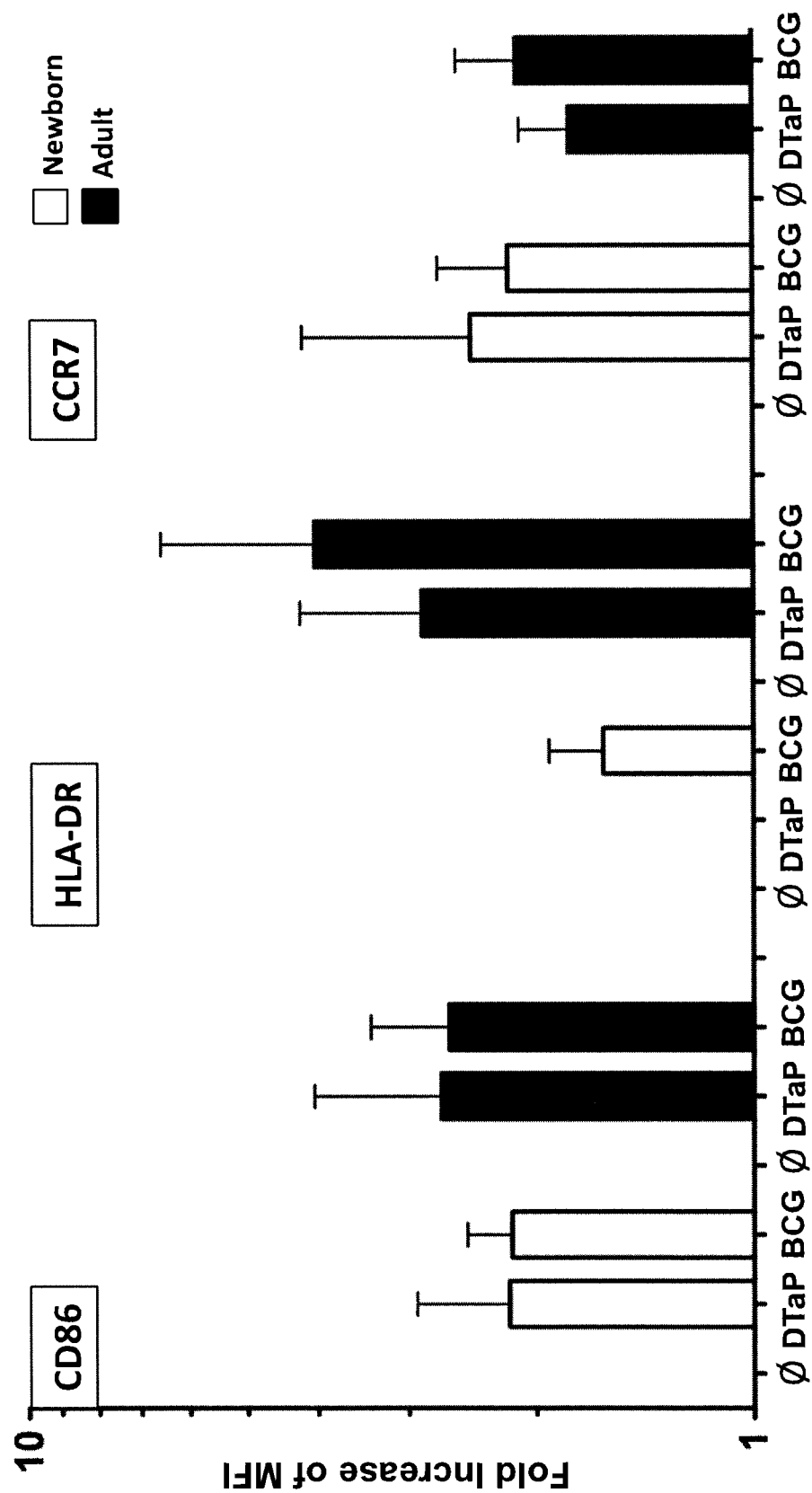
FIG. 10 shows that different doses of vaccines increase maturation markers on the cell surface of reverse transmigrated newborn and adult MoDCs. (N=2-3).

Of note, the vaccines tested had distinct effects on the number of retained and reverse transmigratory MCs. The impact of PCV, DTaP and BCG were compared on retention of MCs in TC matrices (FIG. 9). The subunit vaccines PCV and DTaP reduced retention of MCs in the matrix (FIG. 9A) with corresponding increases in total DCs per TC well (FIG. 9B). In contrast, BCG did not reduce retention index (FIG. 9A) nor increased the total of DCs per TC well (FIG. 9B). In FIG. 9A, after 48 hours of culture, reverse transmigrated cells were harvested and the number of DCs enumerated via flow cytometry and vital staining as described in Methods section. In FIG. 9B, after 48 hours of culture, reverse transmigrated cells were harvested and the number of retained cells inside TCs was obtained by staining TCs with hematoxylin and eosin and by assessing cell density with microscopy and automated cell counting analysis using ImageJ software. The relative number of retained cells was normalized to that in the unstimulated group, defined as 1. The relative number of reverse migratory DCs were normalized to that in the unstimulated group, defined as 1. DTaP and BCG induced significant increases in mature DCs, increasing expression of HLA-DR, CD86, and CCR7 (FIG. 10). ATCs and NTCs were colonized with MCs and stimulated with DTaP (1:100 vol/vol) and BCG (1:10 vol/vol). After 48 hrs of incubation, reverse transmigrated mature DCs were harvested and immunophenotyped for CD86, HLA-DR and CCR7 by polychromatic flow cytometry as described in Methods section. Data are expressed as a ratio to the unstimulated condition defined as 1.

Effects of a Reactogenic Vaccine on ATCs and NTCs.

Figure 11:
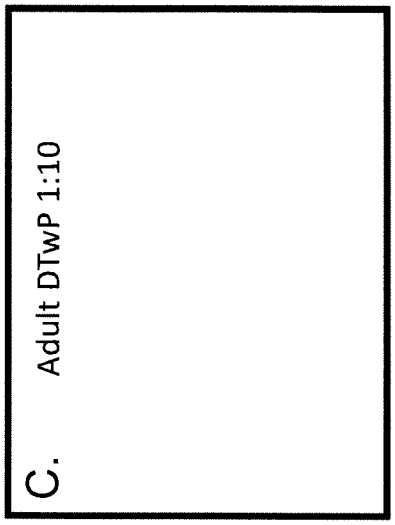
FIGS. 11A-11E show that low doses of diphtheria, tetanus whole cell pertussis (DTwP)-containing vaccine induces greater damage to ATC endothelial monolayers than does DTaP. ATCs were colonized with cryopreserved MCs and left unstimulated (A) or were stimulated with (B) DTwP 1:100, (C) DTwP 1:10, (D) DTaP 1:100, or (E) DTaP 1:100.
Figure 11:
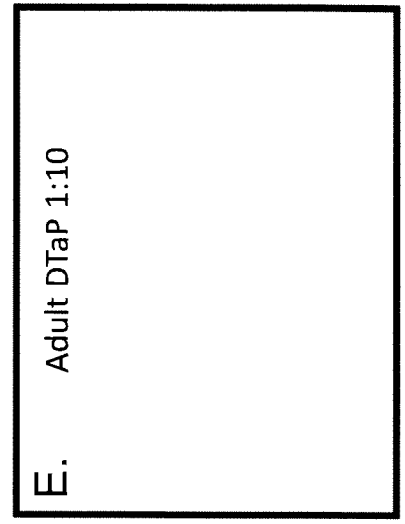
Figure 11:
Figure 11:
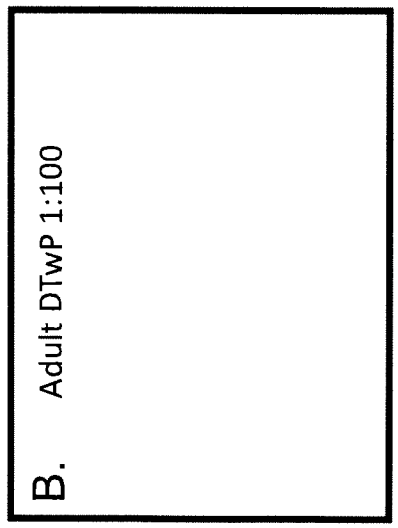
Figure 11:
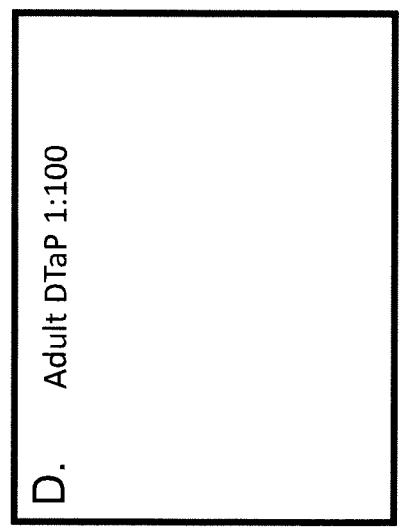

To assess the impact of a vaccine with relatively high reactogenicity in the TCs, the pentavalent combination vaccine ("EASYFIVE") containing whole cell pertussis (wP) was employed in the study. Note that the wP was removed from the U.S. market due to its reactogenicity. After 48 h, monolayers were washed with 1×DPBS to remove any residual MC debris. TC endothelial monolayers/matrix cushions were fixed with 10% paraformaldehyde and imaged on a Nikon TS100 inverted microscope using the 4× objective. Endothelial layers were examined for monolayer integrity and cell morphology. TCs stimulated with DTwP-containing EasyFive vaccine demonstrated non-confluent patches of missing endothelial cells suggestive of high reactogenicity. Whereas unstimulated ATC HUVEC monolayers appeared intact (FIG. 11A), addition of the EasyFive vaccine containing DTwP at 1:100 and 1:10 (vol/vol) resulted in evident damage to the TCs as evidenced by marked damage to the endothelial monolayer (FIGS. 11B and C) that was not observed in the DTaP condition (FIGS. 11D & E). Higher damage is noted by the loss of endothelial cells. This end-point can be suitable for assessing vaccine reactogenicity/toxicity. Damaging effects of the DTwP-containing EasyFive™ vaccine on NTCs were even more pronounced (FIGS. 12B & C). In FIG. 12, after 48 h, monolayers were washed with 1×DPBS to remove any residual MC debris. TC endothelial monolayers/matrix cushions were fixed with 10% paraformaldehyde and imaged on a Nikon TS100 inverted microscope using the 4× objective. Endothelial layers were examined for monolayer integrity and cell morphology. TCs stimulated with DTwP-containing EASYFIVE vaccine demonstrated non-confluent patches of missing endothelial suggestive of high reactogenicity.

Figure 13:
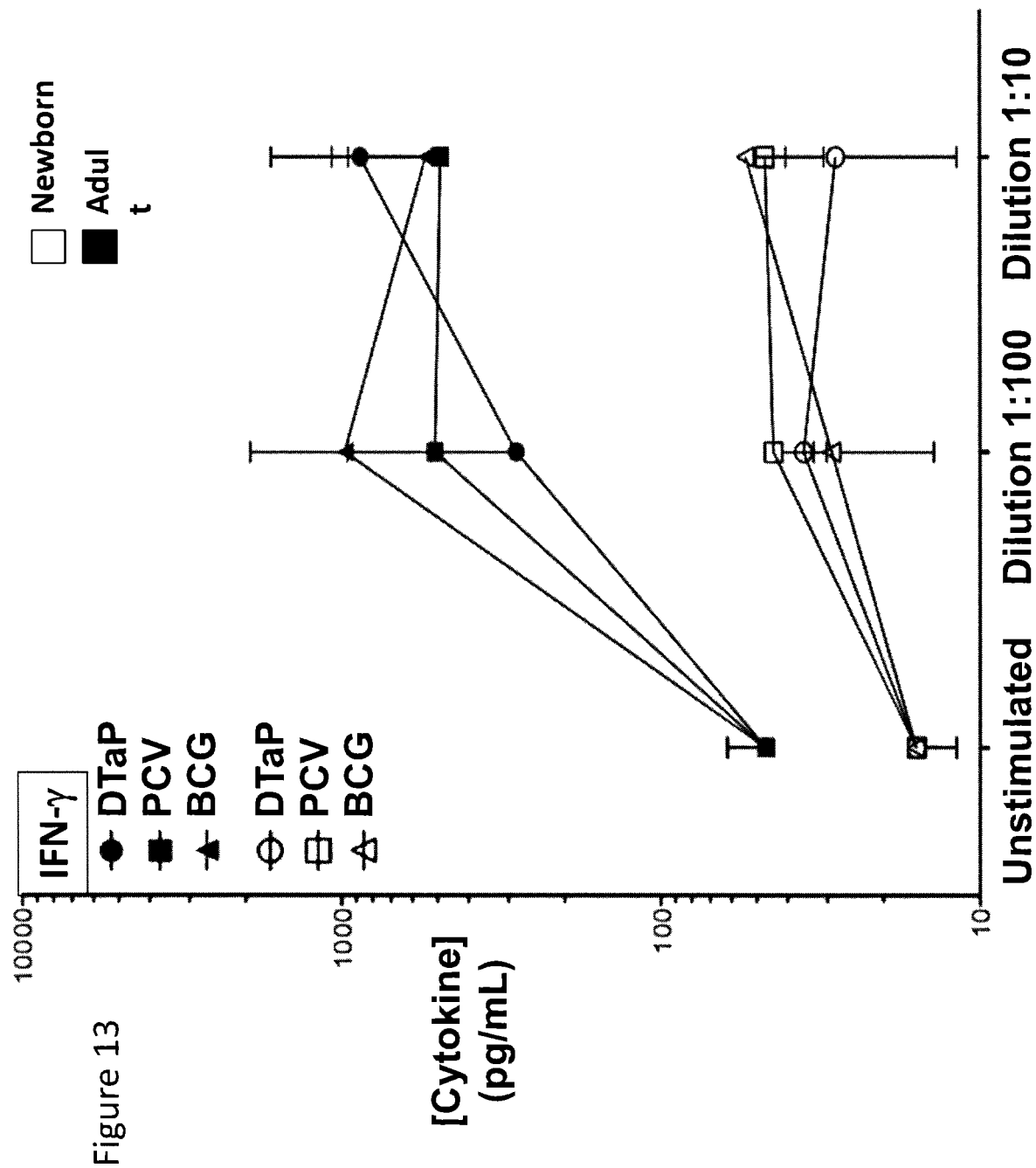
FIG. 13 shows that neonate tissue constructs (NTCs) demonstrate impaired IFN-γ response to different doses of vaccines compared to adult tissue constructs (ATCs). (N=2-4).

Cytokine responses of MC-colonized TCs to BCG, PCV and DTaP vaccines. The impact of vaccines on cytokine generation by MC-colonized TCs was next assessed by harvesting conditioned media after 48 hours stimulation. Substantial impairments in neonatal IFN-γ production were noted for NTCs as compared to ATCs, both under basal conditions (no stimulus added) and upon stimulation with PCV, DTaP and BCG (FIG. 13). In FIG. 13, MC-colonized NTCs and ATCs were stimulated for 48 hrs with 1:100 or 1:10 (vol/vol) of DTaP-, PCV- or BCG-vaccinated prior to harvest of conditioned media for measuring IFN-γ as descried in Methods. Impairments in vaccine-induced IFN-γ production under both unstimulated and vaccine-stimulated conditions.

Figure 14:
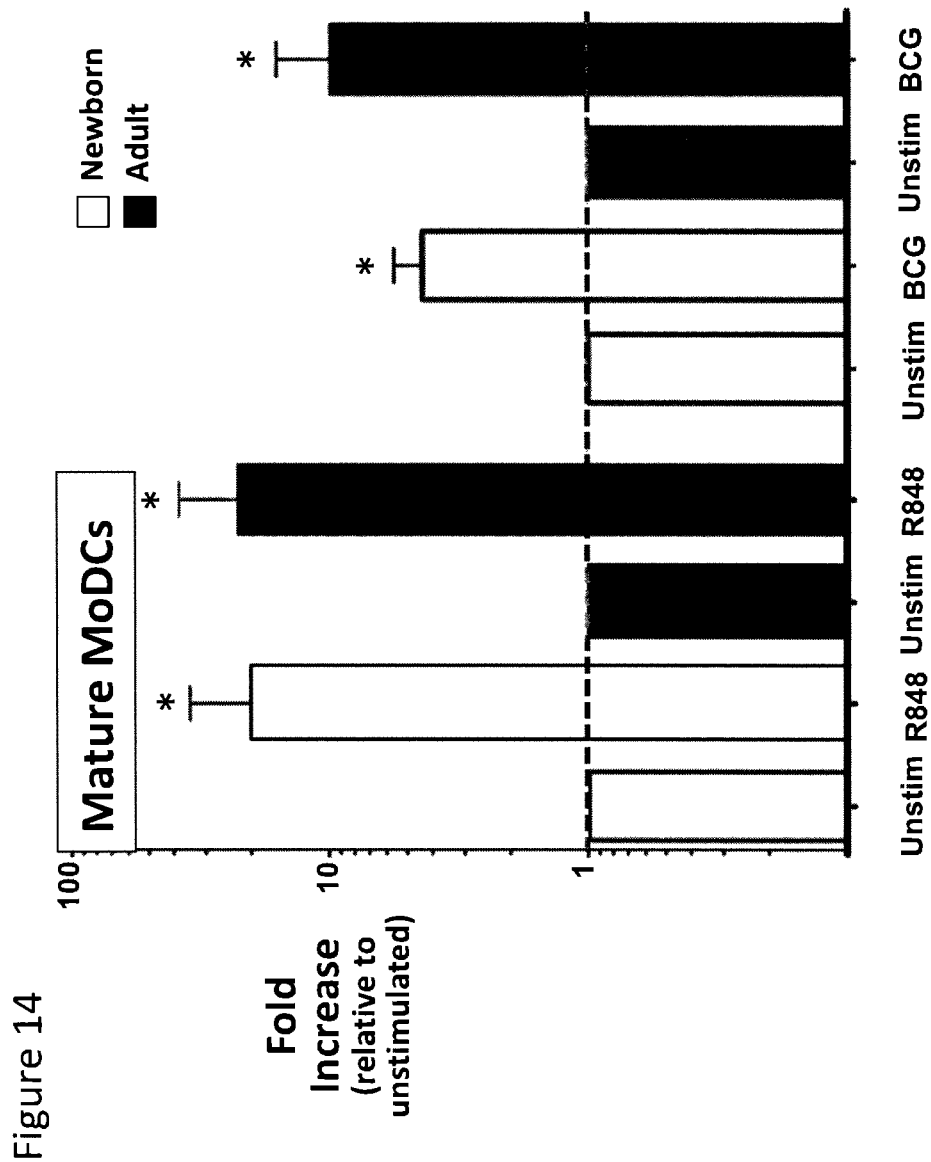
FIG. 14 shows that R848 and BCG induce maturation of CD33+ and/or CD14+ monocyte-derived DCs in NTCs and ATCs. Data are expressed as fold increase over the unstimulated condition. (N=3, paired 2-tailed T test; * P<0.05).

CD 33+ monocytes can colonize tissue constructs to generate MoDCs. A key aspect of DC function is their ability to activate naïve lymphocytes as a step towards adaptive immunity. However, MC-colonized TCs generate unequal numbers of neonatal and adult reverse transmigrated MoDCs and also allow lymphocyte extravasation into TCs, potentially confounding downstream lymphocyte co-culture. In order to enable assessment of pure NTC-derived MoDCs, devoid of co-migrated lymphocytes, for downstream lymphocyte activation studies, positively selected CD 33+ Mos were employed for TC colonization instead of mixed MCs. CD 33+ Mo-colonized TCs were stimulated with BCG or R848 (TLR7/8) to assess DC development and maturation prior to T cell-stimulation studies. R848 (50 µM) and BCG (1:10) significantly induced mature MoDCs from NTCs and ATCs (FIG. 14). FIG. 14 shows that maturation manifested in a fold increase of reverse migrated mature MoDCs over unstimulated tissue constructs (TCs). Purified newborn and adult CD 33+ Mos extravasated into TC and were cultured for 48 h either unstimulated or with R848 (TLR7/8; 50 µM) or BCG vaccine (1:10 vol/vol). The number of reverse transmigrated viable mature DCs per TC were enumerated by flow cytometry and vital staining as described in Methods.

Figure 15:
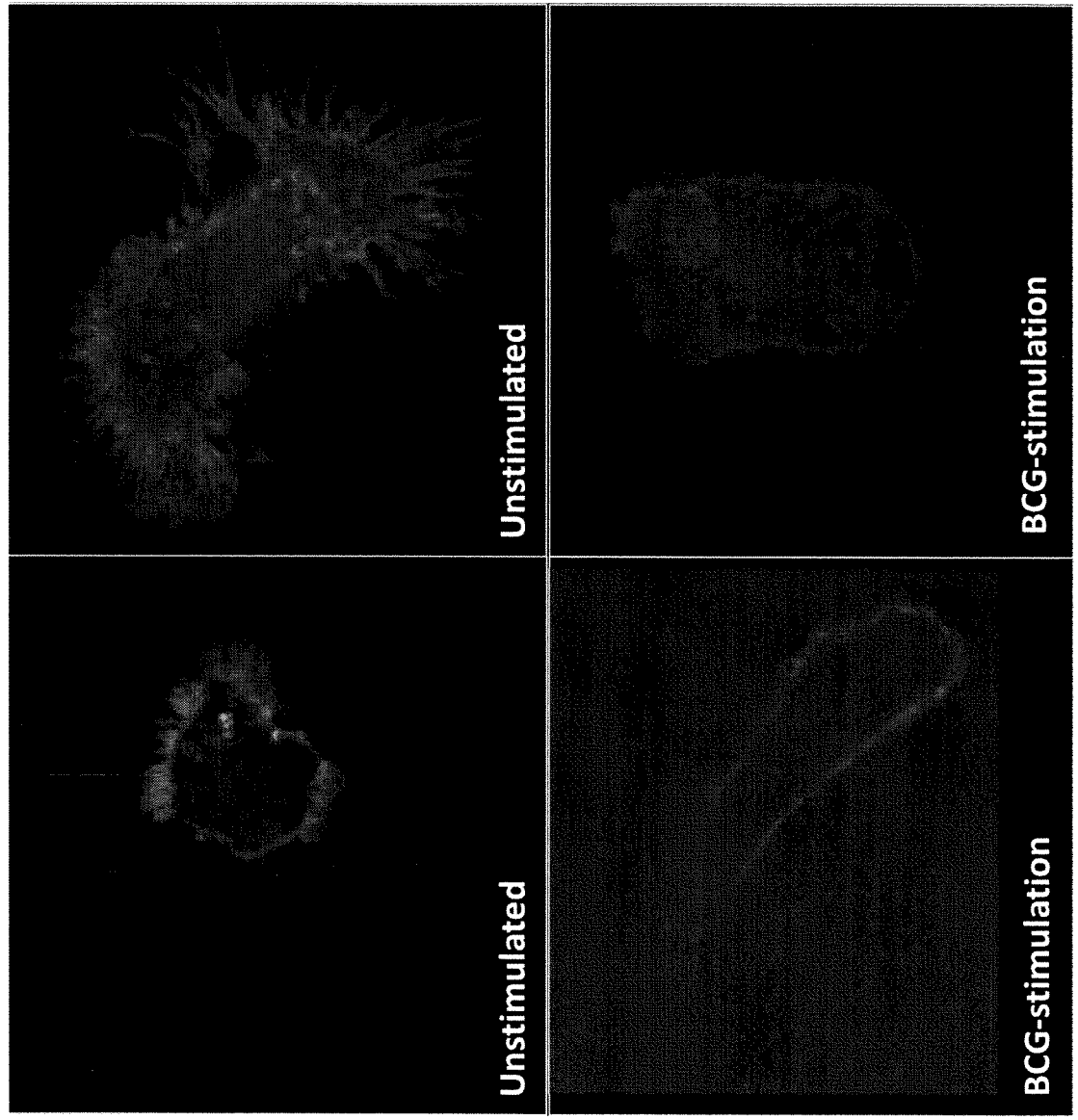
FIG. 15 shows that CD33+ MoDCs from NTCs and ATCs have the characteristic dendritic cell morphology and that BCG induces up-regulation of surface HLA-DR expression on these cells.

Confocal microscopy demonstrated that BCG-pulsed NTC-derived MoDCs had a dendritic morphology and upregulated HLA-DR surface expression (FIG. 15). NTCs and ATCs were colonized with purified neonatal and adult CD 33+ Mos then cultured in plasma without stimulation or with addition of BCG (1:10 vol/vol). After 48 hr, reverse transmigrated MoDCs were harvested, permeabilized and stained for HLA-DR, Actin filaments and DNA and analyzed by confocal microscopy as described in Methods. BCG-stimulation was associated surface localization of HLA-DR molecules consistent with induction of MoDC maturation.

Figure 23:
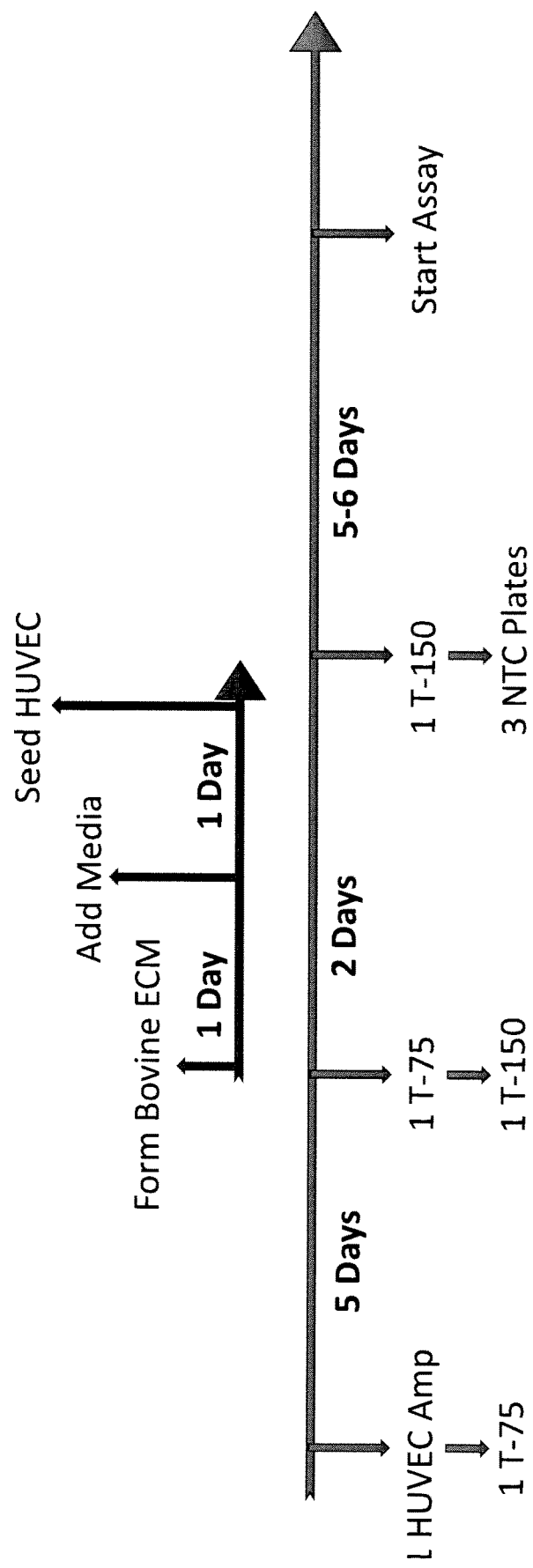
FIG. 23 shows a general timeline in the making of tissue construct using bovine extracellular matrix, e.g., bovine collagen. The seeded endothelial cells require about 5-6 days to form a monolayer, after which an antigen assay can then be performed.
Figure 24:
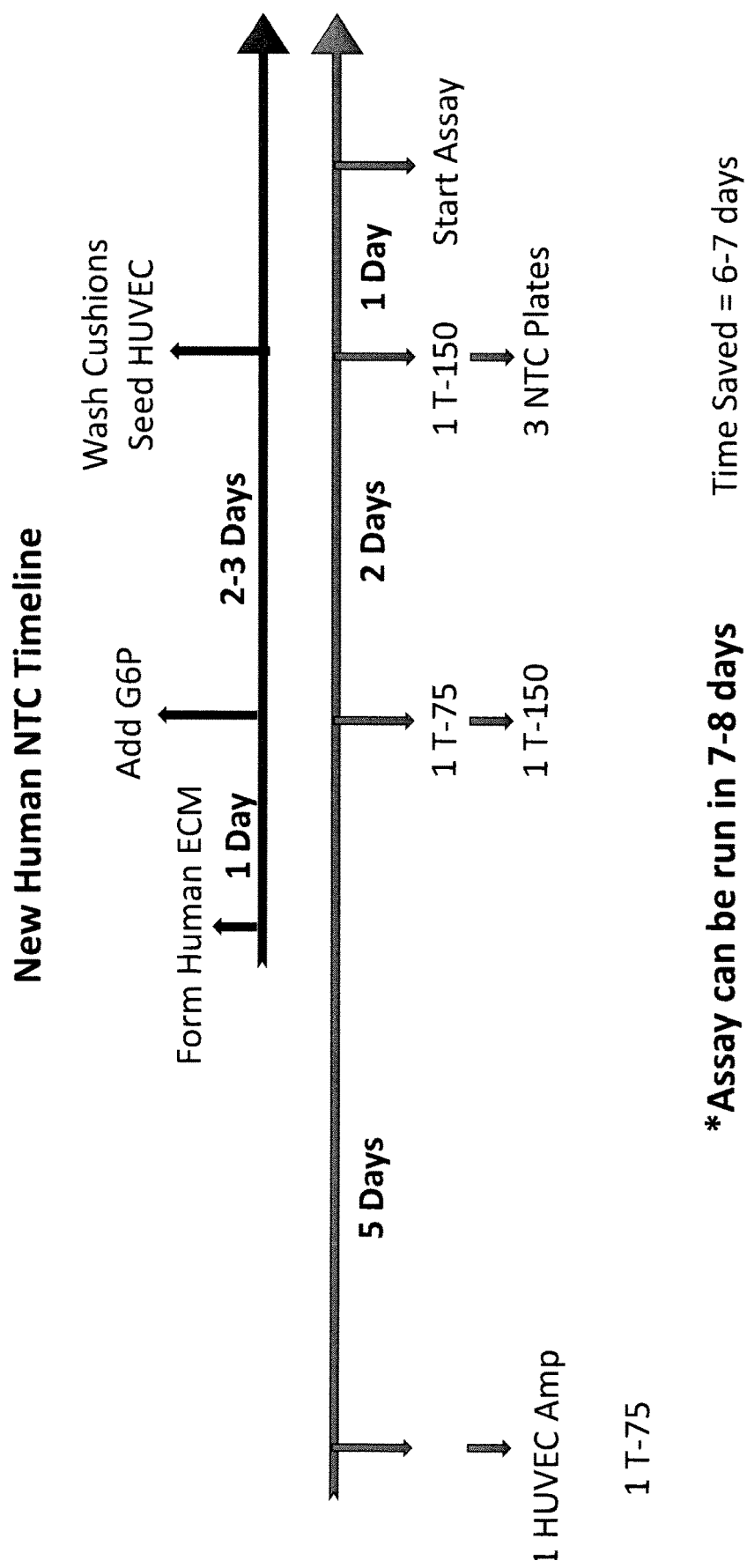
FIG. 24 shows a general timeline in the making of tissue construct using human extracellular matrix, e.g., human collagen. In contrast to a bovine extracellular matrix shown in FIG. 23, the seeded endothelial cells require only about 1 day to form a monolayer, after which an antigen assay can then be performed. Thus, the antigen assay can be performed earlier using extracellular matrix derived from a human.

Human collagen can be modified to produce an entirely humanized extracellular matrix. In order to study MoDC-lymphocyte interactions, an entirely humanized TC was developed. Such humanized TC avoids potential immune responses due to xenologous (bovine) components: e.g., FBS and bovine collagen. In developing entirely human TCs, it was noted that type I human collagen is normally produced by fibroblasts in an immature state and requires maturation via glycosylation to a form more suitable for cell attachment [17, 18]. As most commercial sources of mature human collagen are extracted from cadaveric donors, are costly, and contain high levels of endotoxin, it was evaluated whether large quantities of pure endotoxin-free collagen could be matured in vitro for use in creating TCs. To this end, the effect of Glucose-6-phosphate (G6P), a pro-glycation agent, were assessed on human collagen cushions and HUVEC cell attachment, comparing incubation of human collagen in 50 mM, 100 mM and 225 mM G6P for 2, 3 and 5 days. Human type I collagen was treated with 50 mM, 100 mM and 225 mM of pH-neutralized Glucose-6-Phosphate for 5 days of collagen maturation. Matrices containing collagen matured with 225 mM G6P for 5 days generated completely confluent "cobblestone" endothelial monolayers within 1 day of HUVEC seeding. Use of FBS on extracellular matrix containing bovine collagen does not yield a confluent HUVEC layer at 1 day. In contrast, using G6P-matured human collagen cushion allows HUVECs to rapidly establish a confluent monolayer after 1 day using a comparable seeding density, which with inclusion of 50% (vol/vol) human newborn heat-treated platelet-poor pooled plasma (HI-HNPP) yields a completely human TC. It was noted that incubation of collagen in 225 mM of G6P for 5 days generated completely confluent "cobblestone" endothelial cell monolayers (FIG. 16). Moreover, HUVEC cells rapidly established confluent monolayers on G6P-treated human collagen using a heat-inactivated human newborn platelet-poor pooled plasma (HI-HNPP). Of note, these modifications in TC preparation not only provide an entirely human construct thereby enabling study of adaptive immune responses without potential effects of xenologous (bovine) components, but also substantially reduces the timeframe required to obtain a confluent HUVEC monolayer from ~5 days (bovine collagen cushions/FBS) to ~1 day (human in vitro-aged collagen/HI-HNPP). See FIGS. 23 and 24.

Figure 17:
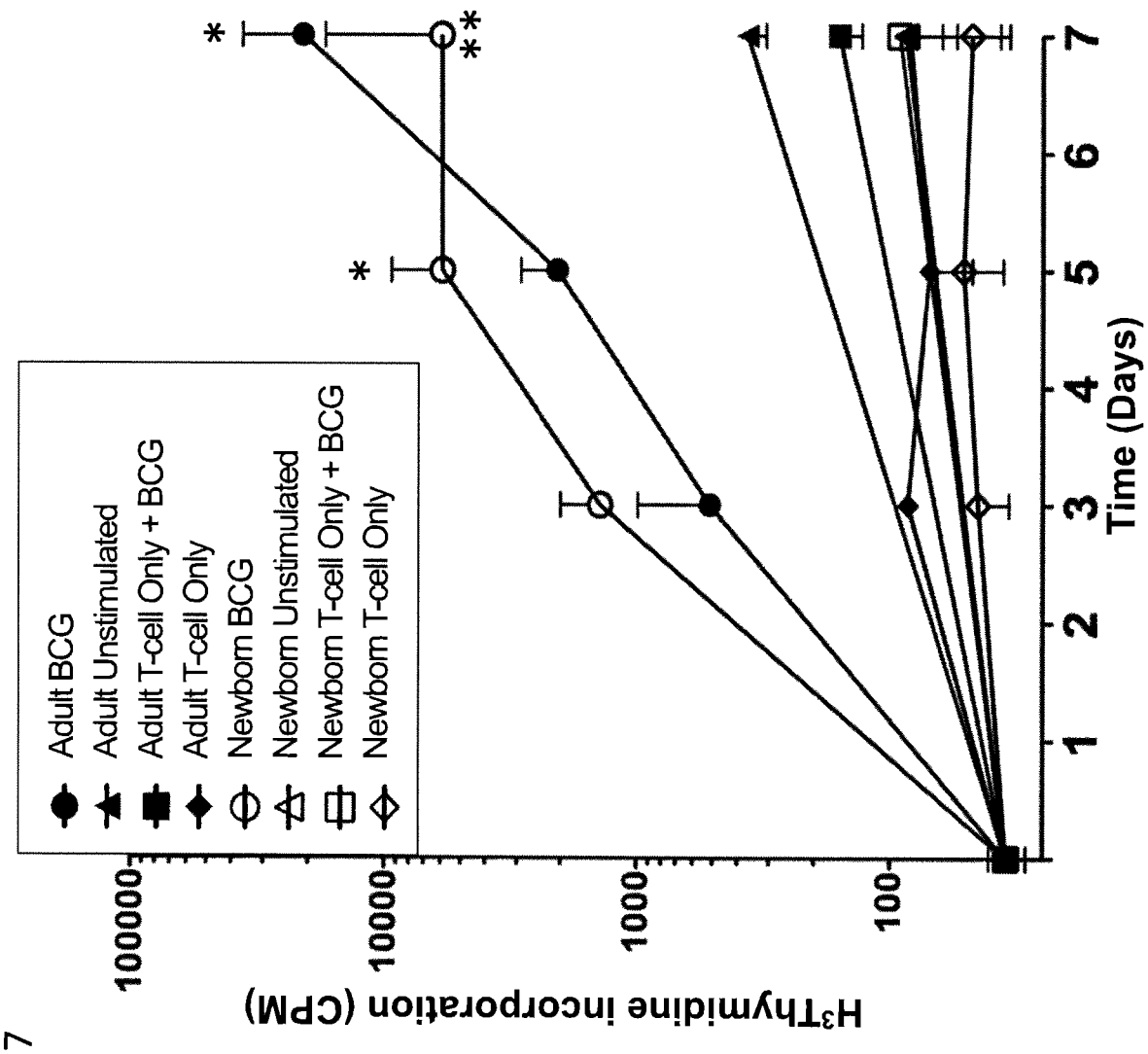
FIG. 17 shows that BCG-pulsed NTC- and ATC-derived MoDCs stimulate proliferation of autologous naïve CD4 T cell cells. (N=3-4, paired 2-tailed T test; *, p<0.05, ** p<0.01).

BCG-pulsed MoDCs enhance proliferation of autologous naïve lymphocytes. To model MoDC-lymphocyte interactions, MoDCs were harvested from unstimulated or BCG-stimulated CD 33+ Mo-colonized human collagen-based TCs then co-cultured with autologous naïve CD4 T cells (negative selection, 99% CD3+ CD45RA+) at a DC:T cell ratio of 1:10 (FIG. 17). CD 33 Mo-colonized NTCs and ATCs were developed without stimulation (e.g, autologous plasma only) or with a 1:10 dilution of BCG. TC-derived MoDCs were then co-cultured with autologous naïve CD4+ CD45RA+ T cells at DC:T ratios 1:100 and 1:10. Lymphocyte proliferation was assessed at days 3, 5 and 7 of co-culture by addition of $^3$H-thymidine 18 hours before harvesting. Lymphocyte proliferation ($^3$H-thymidine incorporation) was assessed at days 3, 5 and 7 of co-culture for the control groups (unstimulated, T cell-only and T cell-only plus BCG), proliferation was negligible. Of note, similar to BCG-pulsed adult MoDCs, BCG-pulsed neonatal MoDCs stimulated robust proliferation of autologous neonatal naïve CD4 T cells.

Figure 18:
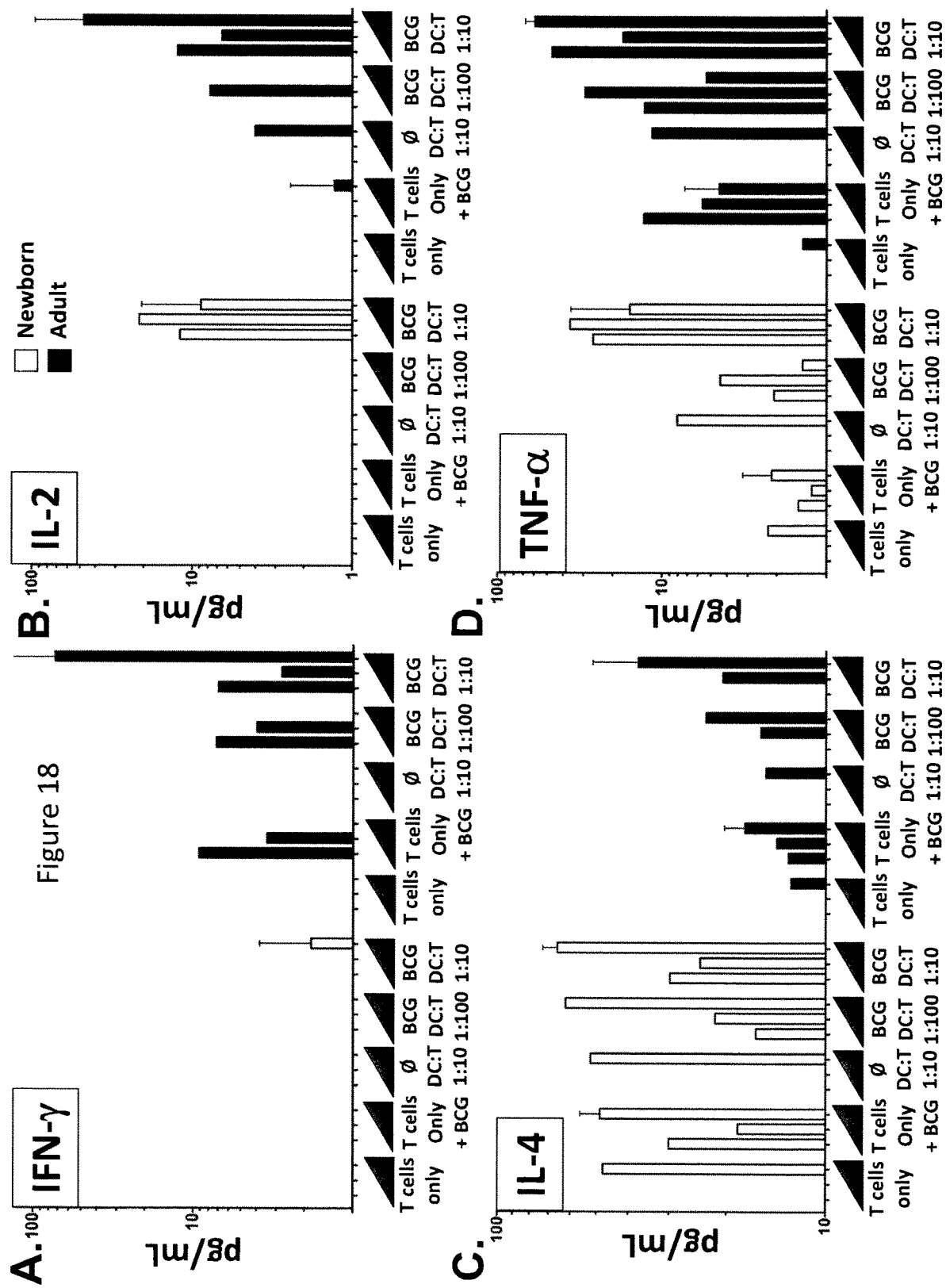
FIG. 18A shows the production of IFN-γ induced by BCG-pulsed MoDC:T cell co-cultures. (N=1-2).
FIG. 18B shows the production of IL-2 induced by BCG-pulsed MoDC:T cell co-cultures. (N=1-2).
FIG. 18C shows the production of IL-4 induced by BCG-pulsed MoDC:T cell co-cultures. (N=1-2).
FIG. 18D shows the production of TNF-α induced by BCG-pulsed MoDC:T cell co-cultures. (N=1-2).

Cytokine analysis of conditioned media from DC:T cell co-cultures. To further characterize effector function of TC-derived MoDCs in stimulating naïve CD4 T lymphocytes, cytokine production by DC:T cell co-cultures was analyzed. Although all neonatal MoDC-lymphocyte co-cultures demonstrated constitutive release of the Th2-polarizing cytokine IL-4 and impaired IFN-γ production, only BCG-stimulated MoDCs showed detectable levels of IL-2 and robust TNF-α production comparable to that of BCG-pulsed ATC-derived MoDCs:lymphocyte co-cultures (FIG. 18). MoDCs derived from BCG-pulsed CD 33-colonized NTCs and ATCs were co-cultured with naïve autologous CD4+ CD45RA+ T cells. After incubation, conditioned media were collected for multiplex cytokine analysis including (FIG. 18A) IFN-γ, (FIG. 18B) IL-2, (FIG. 18C) IL-4, and (FIG. 18D) TNF-α.

Figure 19:
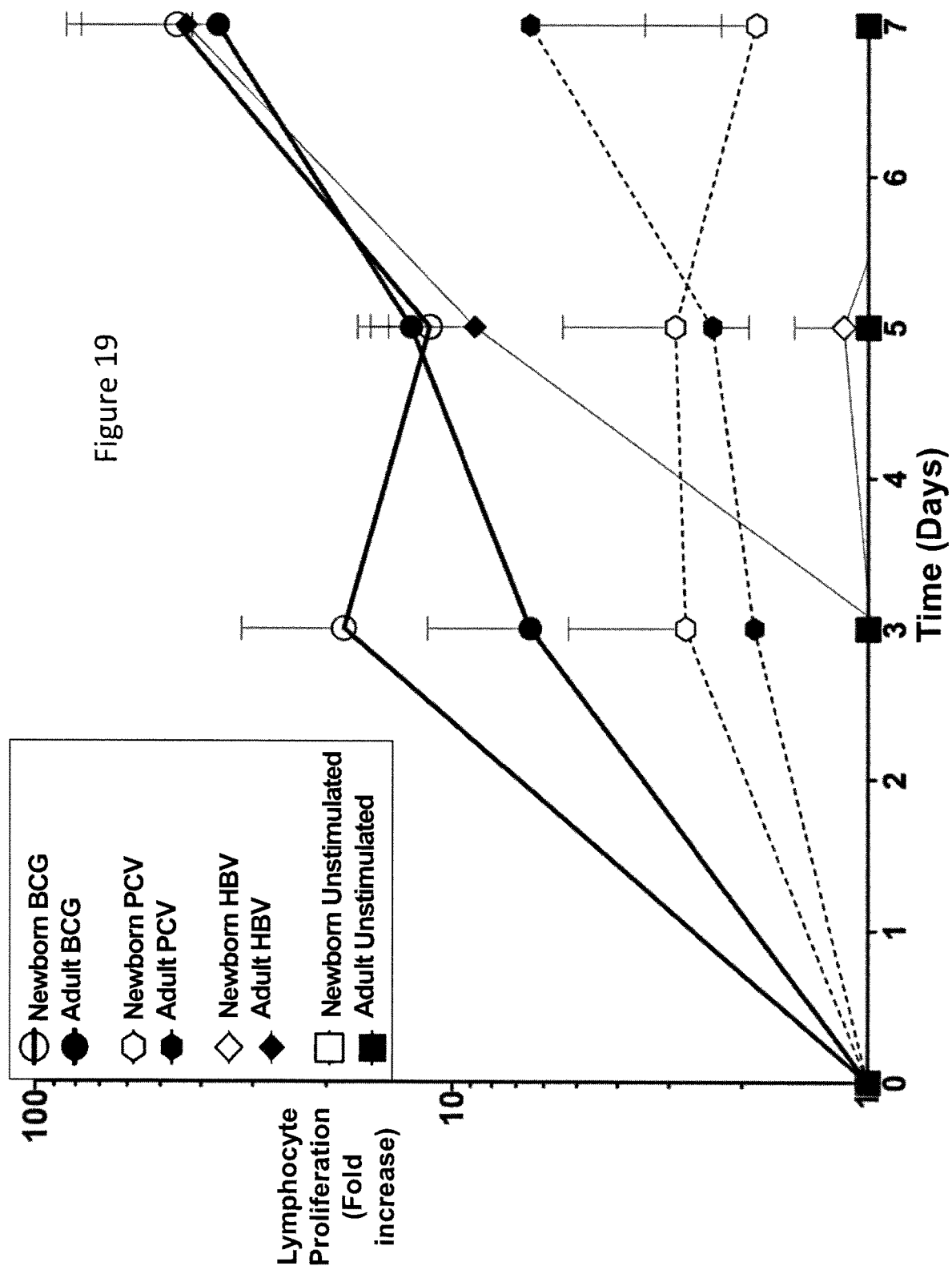
FIG. 19 shows that BCG induces greater lymphocyte proliferation than PCV and HBV. (N=3-5).

Effect of vaccines on the proliferation of autologous naïve CD4 T lymphocytes. the ability of BCG-, PCV- and HBV-pulsed TC-derived MoDCs to induce proliferation of autologous naïve T lymphocytes were next compared. Of the three vaccines evaluated, BCG-vaccinated NTCs and ATCs demonstrated the strongest capacity to induce naïve lymphoproliferation (FIG. 19). To compare the capacity of BCG, PCV and HBV vaccines on the 311-thymidine incorporation assay, the TCs were stimulated following the relative volumetric doses used in vivo and avoiding with this a potential skewing of the results based on their antigenic input. BCG (1:20 vol/vol), HBV and PCV (both at 1:2 dilution vol/vol), with a final volume of 50 μL per TC. Comparing preliminary results (N=3-5 donors) by normalizing against the responses obtained by unstimulated groups, BCG-vaccinated NTC and ATC showed the strongest capacity to induce naïve lymphoproliferation. PCV-pulsed TC-derived MoDCs induced intermediate level lymphocyte proliferation. HBV-pulsed NTC-derived MoDCs demonstrated poor stimulatory capacity while HV-pulsed ATC derived MoDCs demonstrated stronger induction after day 3. PCV demonstrated an intermediate level of lymphocyte proliferation for both the NTC and ATC. With respect to HBV, the ATC demonstrated lymphoproliferation after Day 3, but HBV-pulsed NTC-derived MoDCs induced negligible lymphoproliferation.

Figure 25A:
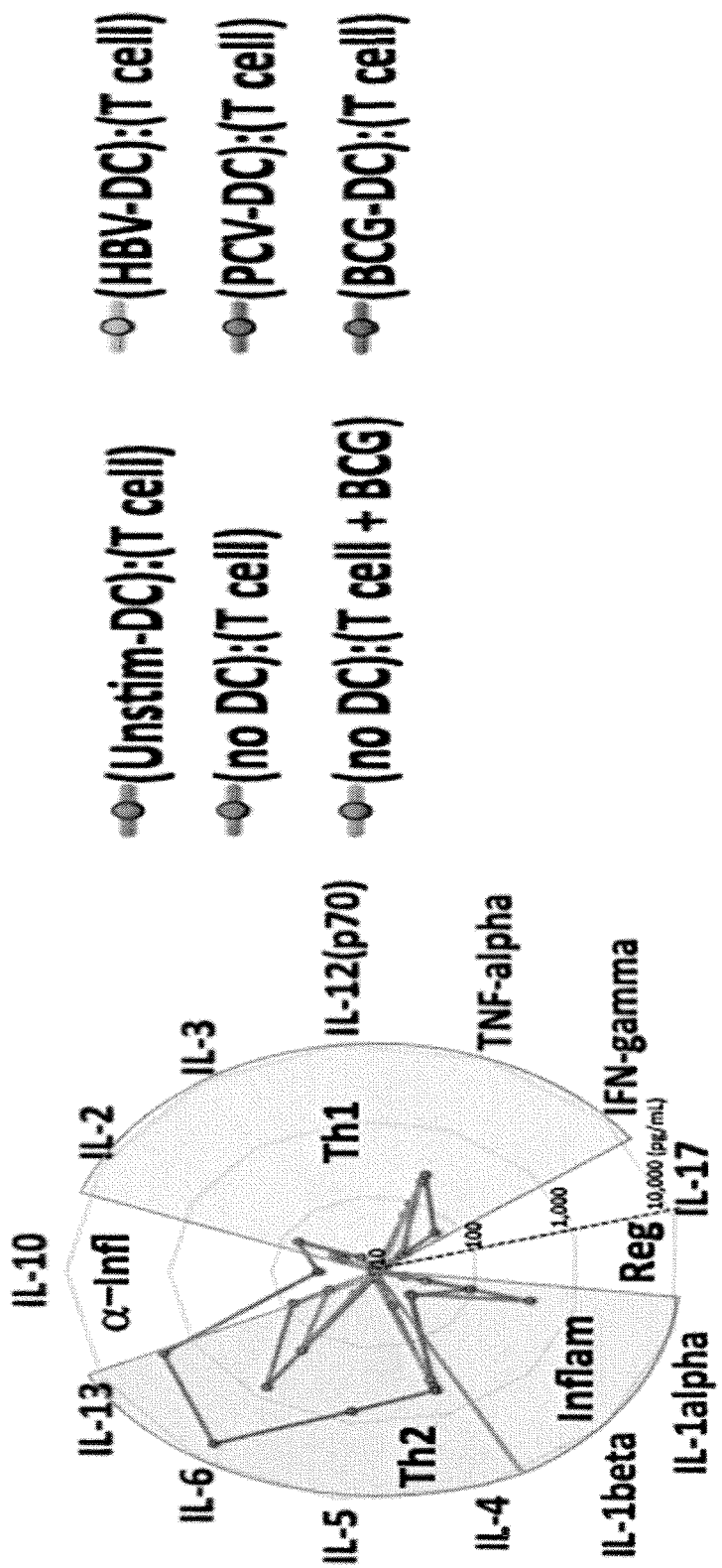
FIGS. 25A-25C show the cytokine production by vaccine-pulsed NTC-derived MoDC:T cell co-cultures using newborn TC or adult TC.
Figure 25B:
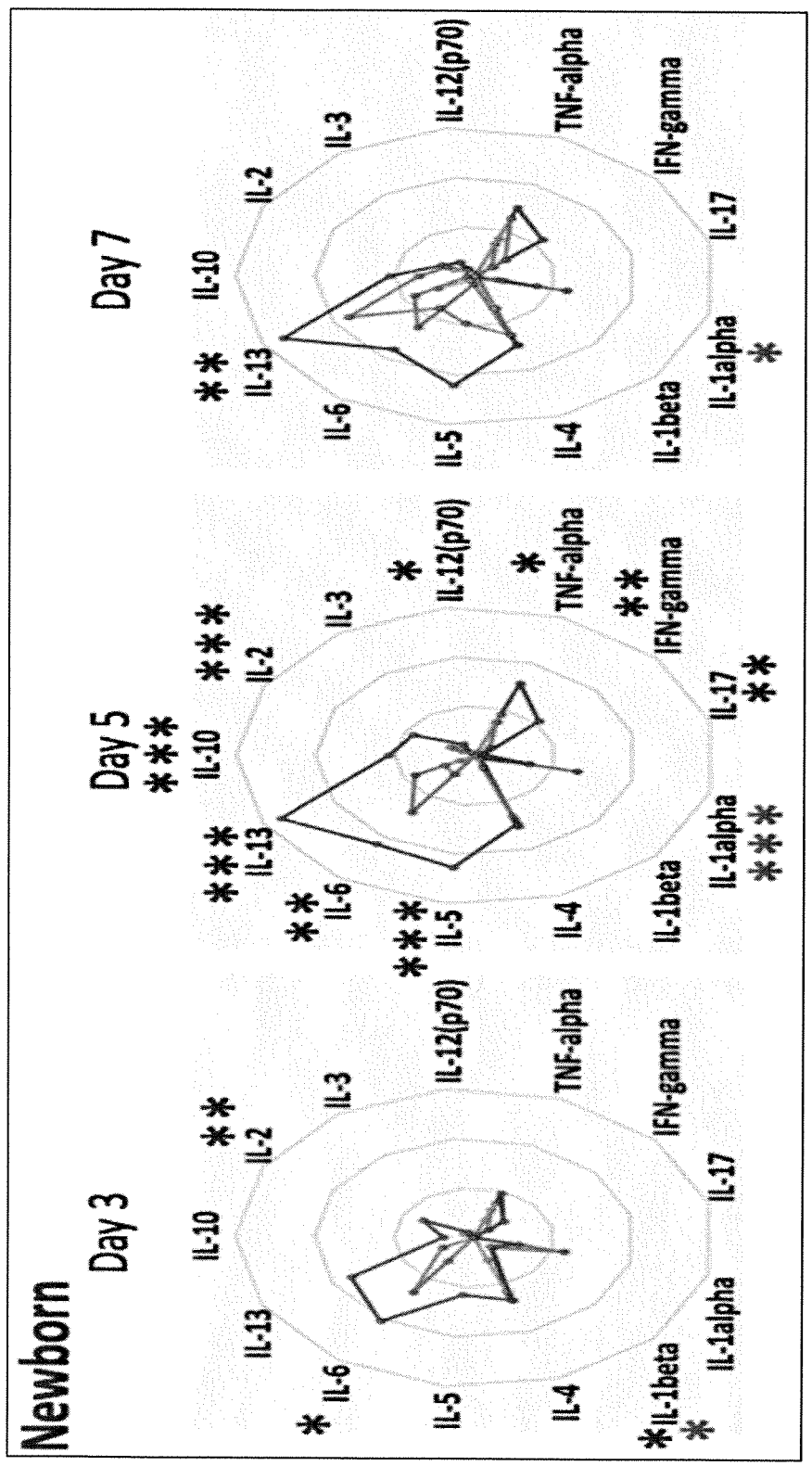
Figure 25C:
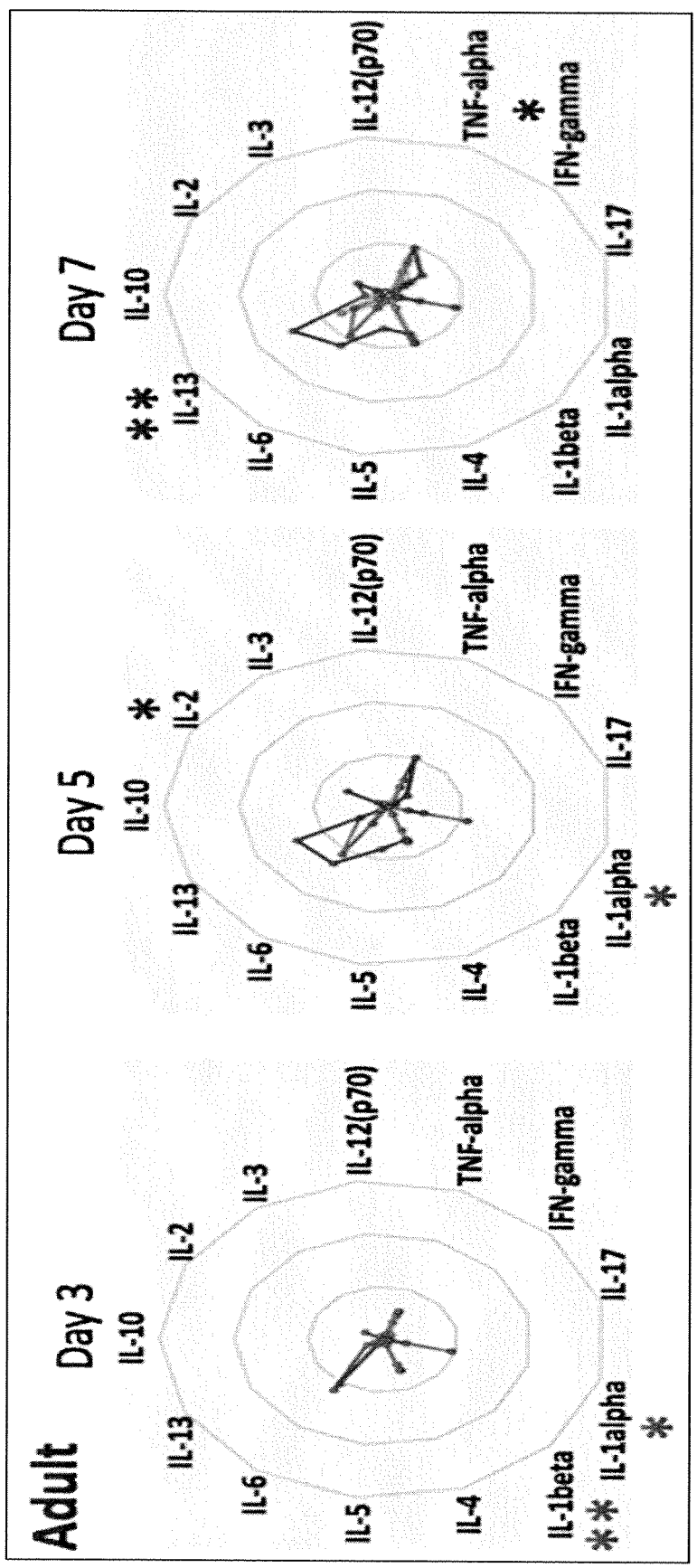

NTC-derived MoDC:lymphocyte co-cultures allow characterization of vaccine-induced cytokine polarization. The NTC is amenable to measuring release of soluble mediators. Indeed, conditioned media were collected and cryopreserved for each time-point of the 7-day MoDC:lymphocyte co-cultures and cytokine production analyzed using a 26-Cytokine multiplex bead array (Milliplex, Millipore; FIG. 25).

Vaccine-pulsed TC-derived MoDCs were co-cultured with autologous naïve CD4+ T cells in the presence of autologous plasma (10% vol/vol) for 7 days. Conditioned media were harvested at days 3, 5 and 7 and cytokines measured by flourometric bead array (Milliplex, Millipore). Logarithmic radar plots range from 10-10,000 μg/μL with cytokines grouped by functional category: anti-inflammatory IL-10; Th1 polarizing IL-2, IL-3, IL-12(p70), TNF and IFN-γ; Th2-polarizing IL-4, IL-5, IL-6 and IL-13; and Th17 polarizing IL-17. Colored stars match test conditions (color legend above figure) and refer to comparison of unstimulated and vaccine-pulsed MoDCs. Similar analyses comparing cytokine production between age-groups by condition, indicated that newborns secreted significantly greater IL-4 than adults for all conditions. N=5 per group; 2 way-ANOVA (Bonferroni post-test) matched observations; *<0.05; <0.01; *<0.001.

Neonatal co-cultures demonstrated significantly greater constitutive secretion of IL-4 than adult co-cultures, a tendency that may contribute to the Th2-polarization of neonatal immune responses. Overall, in parallel with higher lymphoproliferation, autologous lymphocyte cultures with BCG-pulsed MoDCs produced higher levels of multiple cytokines than did co-cultures with HBV- or PCV-pulsed MoDCs. For example, at Day 5, NTC-derived BCG-pulsed MoDC-containing neonatal co-cultures produced significant and substantial concentrations of Th1 (TNF-α and IFN-γ), Th2 (IL-6, IL-13), and anti-inflammatory (IL-10) cytokines (FIG. 25B). The production of the Th1-effector cytokines TNF-α and IFN-γ by neonatal co-cultures containing BCG-pulsed MoDCs and autologous lymphocytes is particularly noteworthy as these cytokines are induced by BCG in vivo.

Figure 26:
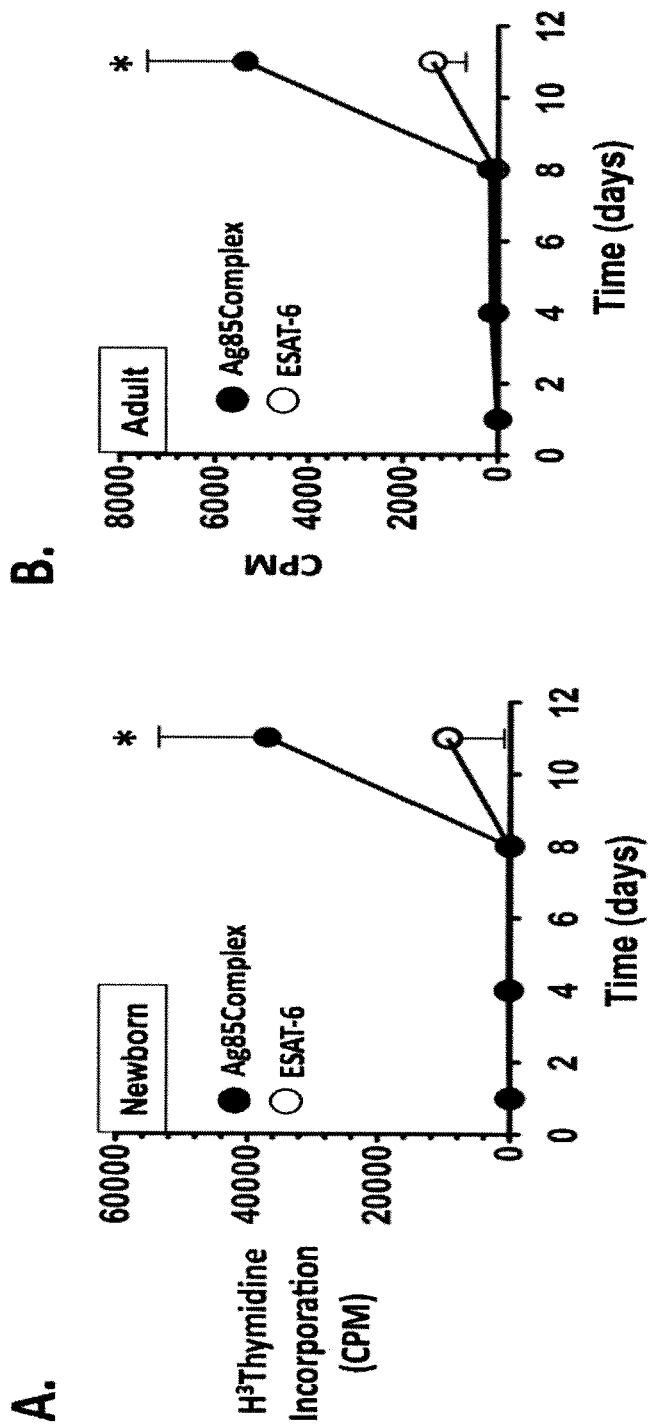
FIGS. 26A and 26B show that BCG-pulsed MoDCs prime autologous naïve T lymphocytes have greater lymphoproliferation in response to recall antigen Ag85Complex (BCG antigen) than control antigen ESAT-6 (TB antigen not found in BCG). This results show NTC can inform single antigen specific CD4 T cell immune responses.

The NTC can be used to model antigen-specific immune responses. A key goal for NTC development is the modeling of antigen-specific immune responses. The inventors selected BCG as the first test vaccine to develop a proof of concept for in vitro immunization and detection of antigen-specific immune responses. BCG-pulsed TC-MoDCs were co-cultured with autologous naïve T cells after which a second round of stimulation employed autologous TC-MoDCs pulsed with a single relevant antigen. The inventors selected Antigen 85 complex (Ag85C, single antigen in 3 different natural-occurring variants) that is present in BCG as well as MT, and as a negative control we selected ESAT-6 present only in MT. The inventors then obtained 13-day propagated T cells (from the co-culture of BCG-TC-MoDCs and autologous naïve CD4 T cells at ratio 1:10) and re-plated them with new autologous TC-MoDCs that were stimulated with either Ag85C or ESAT-6 at ratio 1:7 (FIG. 26). Briefly, 5,000 propagated T cells stimulated by BCG-pulsed TC-MoDCs were subsequently co-cultured with 714 autologous Ag85Complex- or ESAT-6- (each at 0.9 µM) pulsed autologous TC-MoDCs derived from a second/subsequent TC colonized with autologous cells. Representative experiment run in quadruplicate (*p<0.05, unpaired t test, 2-tailed).

These results using single antigens for in vitro lymphoproliferative recall responses validates the use of TCs embodied herein for testing T-cell dependent antigenicity of newborn vaccines. An apparently Ag85C-specific proliferative response was noted after 11 days of culture (FIG. 26). The inventors view this result as a proof of concept for feasibility of single-antigen specificity by the NTC and ATC.

This exemplary study reports the development of a completely human three-dimensional microphysiologic cell culture system that allows for autonomous generation of human neonatal and adult MoDCs under autologous plasma conditions without the addition of exogenous cytokines. This system allows, for the first time, interrogation of the responses of neonatal MCs and autonomously developed MoDCs to adjuvants and vaccines. Multiple studies have characterized responses of neonatal leukocytes in whole blood or as mononuclear cell fractions providing important insights into the distinct nature of neonatal and infant Mos [5, 15, 19]. However, a substantially smaller number of studies have focused on neonatal APCs [4]. These reports have largely studied MoDCs generated in the presence of fetal calf serum with exogenous administration of high concentrations of GM-CSF and IL-4, leaving uncertain the relationship of these cells to those present in vivo. It was found that robust production of MoDCs can be achieved without addition of exogenous cytokines.

CBMCs applied to NTCs demonstrated impaired extravasation relative to PBMCs applied to ATCs. This discrepancy could be related to described impairments in the migration of neonatal leukocytes [20]. Adult CD16+ Mos, known to have a pro-inflammatory cytokine phenotype and high antigen presenting potency, preferentially colonize TCs [9]. In contrast, in this study, newborn CD16+ Mos demonstrated impaired extravasation relative to adult CD16+ Mos, possibly reflecting anti-inflammatory phenotype of neonatal Mos. Nevertheless, the robust reverse transmigration of neonatal MoDCs resulted in similar numbers of RT MoDCs, thereby sufficient for in vitro study. NTC-derived MoDCs demonstrated low expression of CD14 and high HLA-DR as well as a typical DC morphology by confocal microscopy.

It was demonstrated here that the type and concentration of plasma used for culturing leukocytes affects their behavior in vitro. The percentage of plasma in TCs modulated the number of reverse transmigratory leukocytes, reducing reverse transmigration in a plasma proportion-dependent manner. Moreover, the type of extracellular media had marked effects on stimulus-induced TC cytokine production. In prior work we have demonstrated that human newborn plasma inhibits TLR2-mediated Mo TNF-α induction in whole blood [15]. Accordingly, use of non-autologous media such as adult plasma, heat-treated pooled adult AB serum, fetal bovine serum or serum-free commercial media, resulted in dramatic increases in cytokine induction by the TLR2 agonist Pam3Cysk4 on the MC-colonized NTC. Thus the NTC and ATC are platforms that enable assessment of the impact of soluble physiologic factors on the behavior of autonomously generated MoDCs.

The NTC provide an in vitro model to assess reactogenic effects of vaccine formulations. For example, addition of the pentavalent "EASYFIVE" vaccine containing whole cell pertussis, induced substantial damage to TC HUVEC monolayers. The whole cell pertussist was subsequently removed from the U.S. market due to high incidents of fevers and febrile seizures [21].

BCG induced particularly robust immune responses in the NTC. BCG-pulsed MoDCs demonstrated up-regulation of co-stimulatory molecules and production of cytokines. Moreover, upon pulsing with BCG, NTC-derived MoDCs were able to enhance proliferation of autologous naïve lymphocytes. BCG's ability to robustly activate neonatal APCs and lymphocytes in vitro may correspond to its ability to induce immune responses at birth that are protective against disseminated tuberculosis infection in early life [22]. Indeed, BCG has been found to induce Th1-polarized immune responses in human newborns in vivo [23]. Of note, BCG may also reduce mortality that is unrelated to tuberculosis, possibly via non-specific immune enhancing effects [24]. Robust induction by BCG of neonatal APC and lymphocyte activation could contribute to such protection.

A study was performed to show the capacity of TCs to inform immunological memory. Studies on autologous memory CD4 T cell responses were recently initiated (N=1 donor per age group). Adult donor was HBV vaccinated and PPD positive (TB test); Newborn donor has no vaccines. T cells were negatively selected CD4+ T cells that should include the memory and naïve T cells. TCs were vaccinated in vitro with 1:10 and 1:100 dilutions of vaccines BCG and HBV. RT Mo-DCs were harvested and then co-cultured with autologous untouched CD4+ T cells with media containing 10% autologous PPP. NTC recapitulated in vivo by having very low lymphoproliferative responses to HBV as compared to ATC (data not shown). Nonetheless, Newborn CD4+ T cells were able to respond to BCG late during culture time-course (matching the findings with selected naïve T cells). ATC response to BCG was very strong and in agreement with adult donor PPD positive record.

Figure 20:
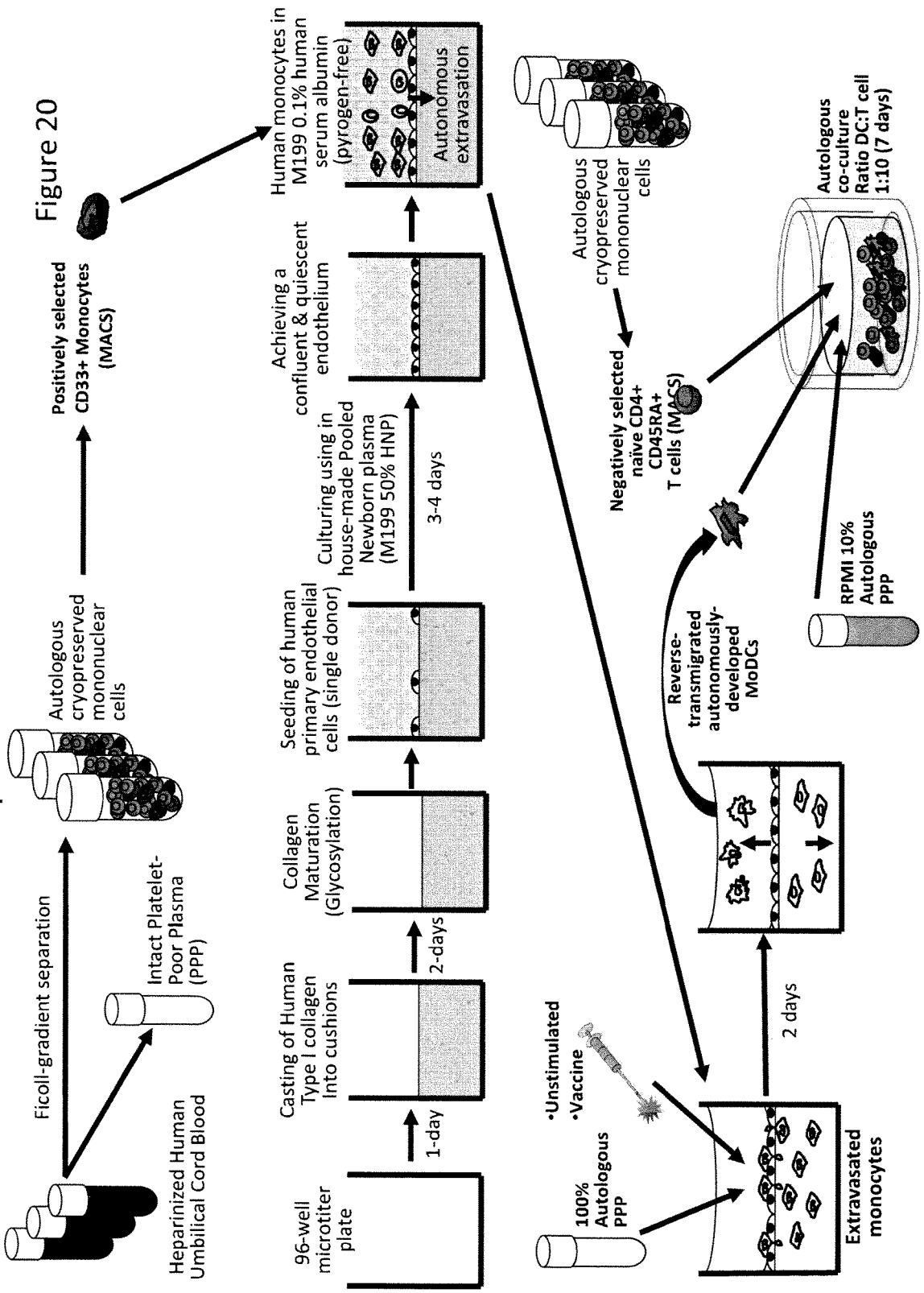
FIG. 20 summarizes some of the unique features of the neonatal tissue construct (NTC). Key novel features of the NTC are highlighted, including use of cord blood as a source of primary mononuclear cells, use of autologous platelet-poor plasma, maturation of type I human collagen for extracellular matrix casting, use of CD33+ and/or CD14+ monocytes, pooled newborn or infant plasma, pyrogen-free conditions, and negative selection of CD4+ CD45RA+ naïve T or CD8+ lymphocytes for autologous MoDC-lymphocyte co-culture. Details of the unique differences over the prior art are described in Table 3.
Figure 21:
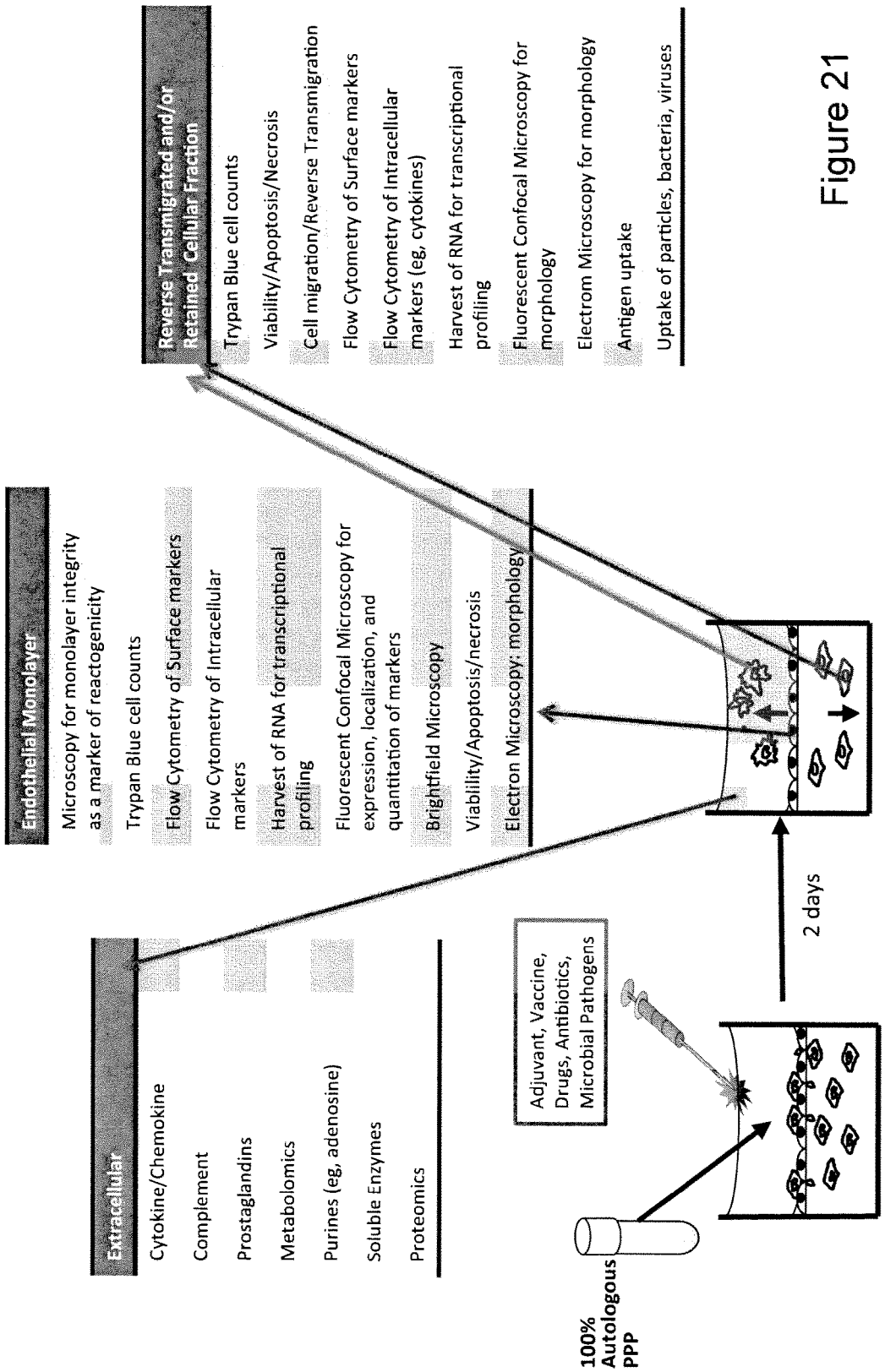
FIG. 21 shows the various parameters and analyses that can be performed for a neonatal tissue culture (NTC); the analyses can be performed for the extracellular culture media, the extracellular matrix, the monolayer of endothelial cells and the reverse transmigrated (RT) or non-RT, retained cellular fraction.
Figure 22:
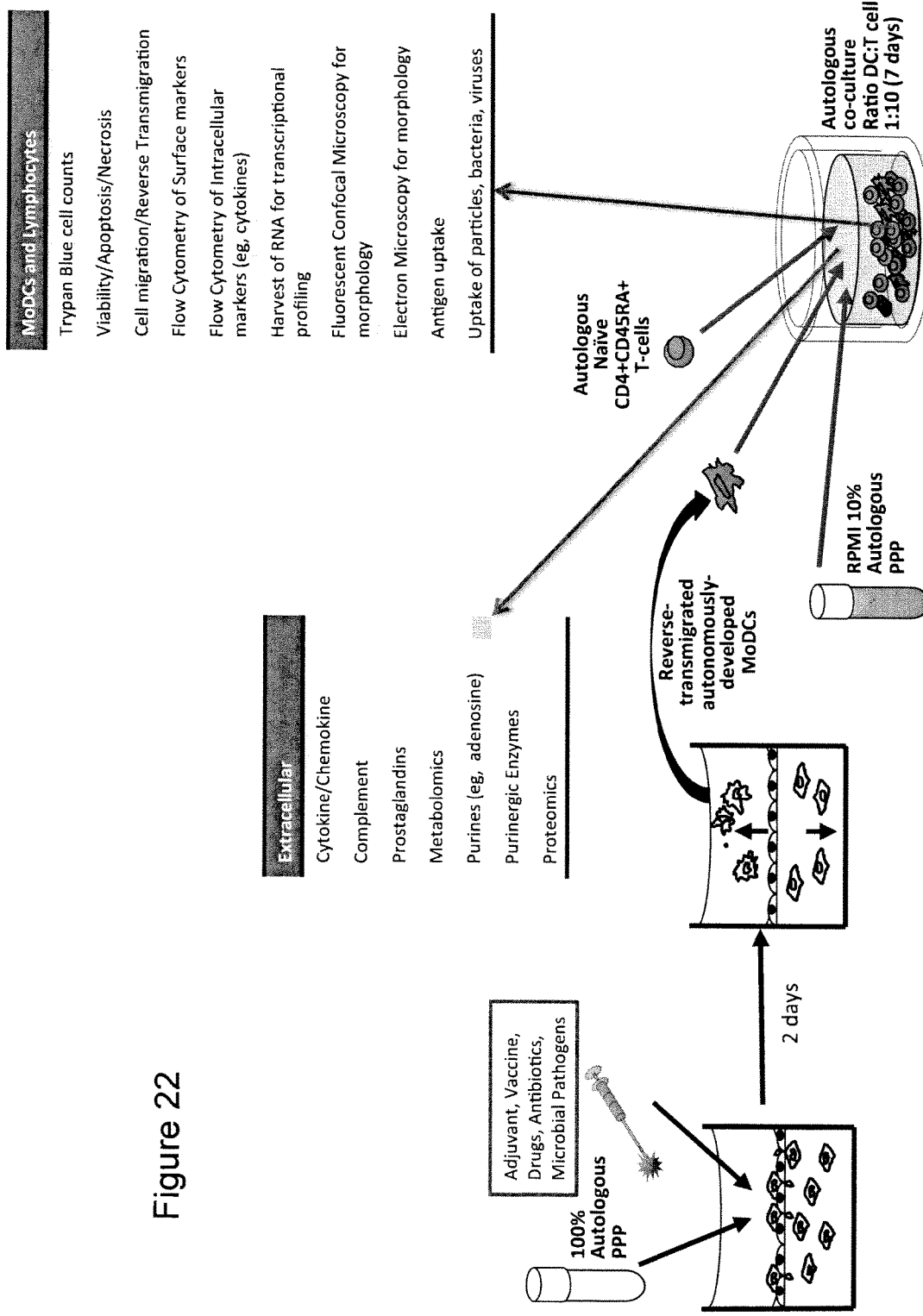
FIG. 22 shows the various parameters and analyses that can be performed for a co-culture of RT-monocyte derived dendritic cells (RT-MoDC) and naïve T cells; the analyses can be performed for the extracellular culture media, the extracellular matrix, and the RT-MoDC and the T cells.

Several NTC design features have been selected to optimize physiologic relevance in an effort to model immune responses that are relevant in vivo: (A) Use of human components including human extracellular matrix, primary age-specific MCs or Mos and autologous naïve T lymphocytes, ensuring that in vitro immune responses are directed to test compounds or vaccinal antigens and not to any heterologous/xenologous components, (B) Use of autologous plasma with potent immunomodulatory properties [2], and (C) use of GMP-grade vaccine formulations and endotoxin-free components for evaluation. These novel features of the NTC are illustrated in FIG. 20 and described in details see Table 3.

Importantly, the disclosed tissue immune-engineering created a TC system that recapitulates key features of newborn immune responses in vivo: (A) impairments in leukocyte migration [20], (B) immune-modulatory effects of plasma [25], (C) skewed cytokine production, including a classic impairment in IFN-γ production [12], (D) toxic effects of a reactogenic vaccine (containing whole cell pertussis) [21], and (E) robust stimulation by BCG, a vaccine known to be effective at birth [22], including marked increases in the ability of BCG-pulsed MoDCs to trigger proliferation of autologous naïve T lymphocytes, and (F) relatively lesser lymphoproliferation in response to MoDCs pulsed with HBV- or PCV, vaccines requiring multiple booster doses for efficacy [2].

In conclusion, this study characterizes for the first time autonomously developed human neonatal MoDCs and adult MoDCs in microphysiologic TCs under autologous plasma conditions. As a novel platform for evaluation of age-specific immune responses, the NTC represents a substantial breakthrough in the study of newborn immunology that can model safety and efficacy of vaccines and thereby inform development of novel vaccine formulations tailored to newborns and infants.

The references cited herein and throughout the specification are incorporated herein by reference in their entireties.

REFERENCES

1. PrabhuDas, M., et al., Challenges in infant immunity implications for responses to infection and vaccines. Nature Immunology, 2011. 12(3): p. 189-94.
2. Sanchez-Schmitz, G. and O. Levy, Development of newborn and infant vaccines. Science translational medicine, 2011. 3(90): p. 90ps27.
3. Steinman, R. M. and J. Idoyaga, Features of the dendritic cell lineage. Immunol Rev, 2010. 234(1): p. 5-17.
4. Willems, F., S. Vollstedt, and M. Suter, Phenotype and function of neonatal dendritic cells. European Journal of Immunology, 2009. 39: p. DOI 10.1002/eji.200838391.
5. Kollmann, T. R., et al., Neonatal innate TLR-mediated responses are distinct from those of adults. J Immunol, 2009. 183(11): p. 7150-60.
6. Levy, O., et al., The adenosine system selectively inhibits TLR-mediated TNF-alpha production in the human newborn. J Immunol, 2006. 177: p. 1956-1966.
7. Randolph, G. J., J. Ochando, and S. Partida-Sanchez, Migration of dendritic cell subsets and their precursors. Annu Rev Immunol, 2008. 26: p. 293-316.
8. Randolph, G. J., et al., Differentiation of monocytes into dendritic cells in a model of transendothelial trafficking. Science, 1998. 282(5388): p. 480-3.
9. Randolph, G. J., et al., The CD16(+) (FcgammaRIII(+)) subset of human monocytes preferentially becomes migratory dendritic cells in a model tissue setting. J Exp Med, 2002. 196(4): p. 517-27.
10. Higbee, R. G., et al., An immunologic model for rapid vaccine assessment—a clinical trial in a test tube. Ahern Lab Anim, 2009. 37 Suppl 1: p. 19-27.
11. Ma, Y., et al., Assessing the immunopotency of Toll-like receptor agonists in an in vitro tissue-engineered immunological model. Immunology, 2010. 130(3): p. 374-87.
12. Levy, O., Innate immunity of the newborn: basic mechanisms and clinical correlates. Nat Rev Immunol, 2007. 7(5): p. 379-90.
13. Adkins, B., C. Leclerc, and S. Marshall-Clarke, Neonatal adaptive immunity comes of age. Nature Reviews. Immunology., 2004. 4(7): p. 553-64.
14. Siegrist, C. A., et al., Determinants of infant responses to vaccines in presence of maternal antibodies. Vaccine, 1998. 16(14-15): p. 1409-14.
15. Levy, O., et al., Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol, 2004. 173(7): p. 4627-34.
16. Belderbos, M. E., et al., Skewed pattern of Toll-like receptor 4-mediated cytokine production in human neonatal blood: low LPS-induced IL-12p70 and high IL-10 persist throughout the first month of life. Clin Immunol, 2009. 133(2): p. 228-37.
17. Francis-Sedlak, M. E., et al., Characterization of type I collagen gels modified by glycation. Biomaterials, 2009. 30(9): p. 1851-6.
18. Francis-Sedlak, M. E., et al., Collagen glycation alters neovascularization in vitro and in vivo. Microvascular research, 2010. 80(1): p. 3-9.
19. Burl, S., et al., Age-dependent maturation of Toll-like receptor-mediated cytokine responses in Gambian infants. PLoS ONE, 2011. 6(4): p. e18185.
20. Yegin, O., Chemotaxis in childhood. Pediatric Research, 1983. 17(3): p. 183-7.
21. David, S., P. E. Vermeer-de Bondt, and N. A. van der Maas, Reactogenicity of infant whole cell pertussis combination vaccine compared with acellular pertussis vaccines with or without simultaneous pneumococcal vaccine in the Netherlands. Vaccine, 2008. 26(46): p. 5883-7.
22. Andersen, P., Tuberculosis vaccines—an update. Nat Rev Microbiol, 2007. 5(7): p. 484-7.
23. Vekemans, J., et al., Neonatal *bacillus* Calmette-Guerin vaccination induces adult-like IFN-gamma production by CD4+ T lymphocytes. European Journal of Immunology, 2001. 31(5): p. 1531-5.
24. Aaby, P., et al., Randomized trial of BCG vaccination at birth to low-birth-weight children: beneficial nonspecific effects in the neonatal period? The Journal of infectious diseases, 2011. 204(2): p. 245-52.
25. Angelone, D. F., et al., Innate immunity of the human newborn is polarized toward a high ratio of IL-6/TNF-alpha production in vitro and in vivo. Pediatr Res, 2006. 60(2): p. 205-9.

TABLE 1

| | Abbreviations |
|---|---|
| Ab | Antibody |
| APC | Antigen-presenting cell |
| ATC | Adult Tissue Construct |
| BCG | Bacille Calmette-Guérin |

TABLE 1-continued

Abbreviations

| | |
|---|---|
| CBMCs | Cord blood mononuclear cells |
| DC | Dendritic cell |
| DTaP | Diptheria tetanus acellular Pertussis vaccine |
| FBS | Fetal bovine serum |
| G6P | Glucoase-6-phosphate |
| HBV | Hepatitis B vaccine |
| HI-HNPP | Heat-inactivated human newborn platelet-poor pooled plasma |
| HLA | Human leukocyte antigen |
| HUVECs | Human umbilical vein endothelial cells |
| IFN-γ | Interferon-gamma |
| MCs | Mononuclear cells |
| Mo | Monocyte |
| MoDC | Monocyte-derived dendritic cell |
| NTC | Neonatal tissue construct |
| PBMCs | Peripheral blood mononuclear cells (adult) |
| PCV | Pneumococcal conjugate vaccine |
| PPP | Platelet-poor plasma |
| PSG | Penicillin/Streptomycin/L-glutamine |
| RT | Reverse transmigration |
| TCs | Tissue constructs |
| TNF | Tumor necrosis factor |

TABLE 2

Vaccines that have been licensed and/or tested in human newborns and infants. Newborns are from birth to 28 days of age; infants are from 1 month to 2 years old.
Extracted from Sanchez-Schmitz Science & Levy Science Translational Medicine 2011 3(90): 27

| | Youngest age | Route | Vaccine (series, in months unless otherwise noted) | Antigen | Adjuvant Intrinsic | Adjuvant Extrinsic | Adverse events | Immune response | Limitations | Ref |
|---|---|---|---|---|---|---|---|---|---|---|
| Licensed | Newborn | PC, ID | BCG (single) | Mycobacterium bovis | TLR-2/4/8/9 | None | Disseminated infection (rare) | CD4, CD8, IFN-γ | | (11) |
| | | IM | HBV (0/1/6) | Virus-like nanoparticles | | Alum | Mild, local (1 to 10%) | IgG | | (77) |
| | | Oral | OPV (single) | Live-attenuated virus | ssRNA | None | Revertant/paralysis (rare) | Neutralizing anti-poliovirus antibodies | Impaired CD4 and IFN-γ response | (16, 78) |
| Studied | Newborn | IM | Pertussis (0/1/2/4) | PTX, pertactin, fHA; or whole cell | PTX | Alum | No serious, mild, local to higher, systemic whole) | Agglutinins, IgG | Suboptimal antibody levels | (22, 79) |
| | | IM | DTaP (0/2/4/6) | Diphtheria and tetanus toxoids | | Alum | No serious | IgG | Lower antibody response at 7 months than those without birth dose | (21, 22, 25) |
| | | IM | Hib (0/4/14) | PRP-CRM/ PRP-T | | None | No serious | IgG | | (80) |
| | | IM | PCV (0/1/2) | CRM 197-pneumo poly-saccharides | | Alum | No serious | CRM 197 Th2 > Th1 | Polarizes subsequent TLR response (Th2) | (28) |
| | | IM | HIV (0/1/3/5), for infants of HIV-infected mothers | HIV-1 gp120 | | MF59 or Alum | No serious | IgG, LP | Alum-HIV shows less lympho-proliferation than MF59-HIV | (34, 35) |
| | | Oral | RV (0/2/4 versus 2/4/6) | Four live virus strains | | None | Mild, local | IgA | Lower, but still acceptable IgA levels at birth dose | (30) |
| | | IM | RTS,S/ ASO1/2 (0/1/2 or 7) | Cicum-sporazoite protein | | AS01/2 (TLR4) | Mild, local | Antibody | | (81) |

TABLE 3

| Feature | Why is different? | Importance/Impact of final readout |
|---|---|---|
| 1. Heparinized human UBC | This system represents the first use of neonatal cord blood in Tissue Constructs (TCs). | Heparinized human umbilical cord blood or human placenta is the source of newborn plasma and newborn leukocytes, essential to model a newborn immune system.<br>The use of pyrogen-free Heparin is believed to be superior to the use of cation chelants (e.g., sodium citrate) that may interfere with proper cell responsiveness. |
| 2. Intact PPP | This system leaves the plasma intact to preserve features uniquely associated to newborns. Other groups have used heat-inactivated plasma or serum, or bovine serum that does not accurately recapitulate immune responses of human newborns. | Intact platelet-poor plasma (PPP) is not heat-inactivated; therefore many distinct immunomodulatory neonatal plasma factors are preserved intact, including:<br>Complement: Newborns have lower levels than adults<br>Antimicrobial proteins & peptides (APPs): Newborns have lower levels than adults; APPs can modulate both innate and adaptive responses.<br>Adenosine: Newborn cord plasma has higher levels than adults; adenosine selectively inhibits production of Th1-polarizing cytokines.<br>Progesterone: Immunomodulatory, placenta-derived<br>Prostaglandin E2 (PGE2): Placenta-derived, effects antigen-presenting cell maturation.<br>Transplacentally derived maternal antibodies ("MatAbs"): Unique to newborns MatAbs can inhibit and/or modify responses to vaccine formulations.<br>Distinct purine metabolism: Based on unpublished observations in the Levy Lab, Neonatal cord blood demonstrates distinct adenosine metabolism reflecting high levels of enzymes involved in adenosine generation (e.g., alkaline phosphatase) and low levels of adenosine metabolizing enzymes (eg, adenosine deaminase = "ADA").<br>Removal of platelets (PLTs) ensures that these particles do not interfere with cell responsiveness under static culture conditions (lack of normal blood flow). In contrast to their actions in moving/flowing blood, platelets under static culture conditions settle on cells that bind them via specific receptors activating PLTs to release immune-modulatory cytokines. Since the objective of the NTC is not modeling wound-healing, PLTs are removed for the NTC. Moreover, cryopreservation of plasma may activate platelets, another reason it is critical to remove them.<br>Intact, and non-heat inactivated plasma also preserve many other immune-modulatory elements found in plasma. |
| 3. Positively selected CD33+ monocytes | The NTC represents the first use of CD33-selected purified neonatal monocytes on Tissue Constructs. | There is a need for comparing self-development and maturation of monocyte-derived dendritic cells (MoDCs) from NTC and ATC under unbiased conditions; and considering that mononuclear cell fractions of newborns and adults show different amounts of monocytes, it was decided to equalize the numbers of newborn and adult monocytes during TC colonization. By selecting monocytes through myeloid marker CD33 instead of monocyte marker CD14, this strategy preserved not just the natural monocyte diversity (e.g. CD14−/CD16+ monocytes) of the samples but their responsiveness since CD14 is an important antigen-capture and adjuvant-signaling molecule. CD14−/16+ monocytes have been found to be very important for autonomous differentiation of reverse transmigrated dendritic cells (DCs). |
| 1. | This system is the only system employing human type I collagen to make TCs. Other groups may cast TC cushions using collagen type I from other species. | It is critical to ensure antigen presentation from vaccines and not from any xenologous antigens the TCs itself (e.g., those that are introduced if non-human proteins are included). Therefore, novel protocols that create entirely human TCs without xenogenic elements were developed. |
| 2. | This TC system is the first to use a collagen maturation step to allow establishment of endothelial cells of a TC. | Collagen maturation refers to a process of natural glycosylation by the use of glucose-6-phosphate solution. This process has been published in diabetes studies, but there is no reports of its use for making TCs. It was discovered here that endothelial cells do not attach to immature human collagen cushions. Therefore, a unique collagen maturation procedure was developed, the collagen maturation allows endothelial cells to attach and form robust monolayers on human collagen cushions. This step has dramatically shortened the time and number of cells needed to create TCs and has resulted in a fully human TC system, from about 13 days to about 8 days. |
| 3. | This TC system employs single donor primary endothelial cells. Other groups have used human pooled endothelial cells. | To minimize undesirable potential immunological interactions between endothelial cells pooled from many humans and the leukocytes of one individual, only single donor human primary endothelial cells were used. The origin of these cells is commercial and obtained from human umbilical veins (HUVEC). This option also helps to preserve individuality of NTC important to evaluate responses base on population diversity.<br>Our lab is currently exploring the role of immune-modulatory elements bound to cells such as:<br>Adenosine Deaminase: Enzyme that destroy adenosine.<br>Ectonucleotidase CD73: Enzyme that creates adenosine.<br>As well as the 4 different types of Adenosine receptors that according to its expression levels may make cells susceptible or refractory to Adenosine. |
| 4. | This is the first system to employ pooled newborn plasma for culturing endothelial cells on TCs. Others have employed heat inactivated human serum or Fetal Bovine Serum ("FBS"). | It is critical to ensure antigen presentation from vaccines and not from the TCs itself; therefore TCs were created without xenogenic elements. Fetal bovine serum has been often used to culture the endothelium on top of the cushions. Instead, we have now used pooled human neonatal cord blood plasma (50% volume/volume with media M199). To our knowledge, this is the first human TC devoid of any xenogenic material. |
| 5. | There is no report known on the use of pyrogen-free human serum albumin during this step. | Traditionally 0.1% bovine serum albumin (BSA) was used during this step. For same reasons mentioned above it was decided to move towards the use of human materials only. Here only pyrogen-free human serum albumin was use at 0.1% in media M199 during this step. |
| 6. | To our extensive knowledge, our TC system is the first to employ 100% intact PPP during the 48 h culture of the NTC and ATC. | The idea behind using 100% PPP at this step goes back to our quest for recapitulating in vitro the elements and conditions found in vivo. Since the NTC and the ATC are representing a microvascularized interstitium and the luminal side of veins is normally exposed in vivo to 100% plasma, we decided to employ 100% autologous PPP. Test elements such as vaccines and adjuvants are thus added into 100% autologous PPP. |

TABLE 3-continued

| Feature | Why is different? | Importance/Impact of final readout |
|---|---|---|
| 7. | This NTC system is the first to employ 10% intact PPP during the co-culture of TC-derived DCs with autologous T cells. | The presence of intact PPP aims to ensure the presence of those immune-modulatory elements found in newborns. Our DC: T cell co-cultures are designed to recapitulate in vitro the events occurring inside draining lymph nodes in vivo. Since lymphatics do not carry complete plasma but a more diluted version of it, it was decided to use only 10% PPP with media RPMI 1640. |
| 8. | This NTC system is the first to use negative-selection of newborn CD4+ CD45RA+ naïve T cells for modeling immune responses in vitro | The aim is to demonstrate autologous naïve newborn immune responses in vitro using autonomously developed DCs from in vitro vaccinated NTCs. It has been suggested that a small percentage of CD4 T cells on newborn blood may come from the mother. Our cryopreserved cord mononuclear cells contain about 2.5% of CD45RO+ cells (memory phenotype) that if not removed may interfere assessment of naïve responses. To ensure that our responses are indeed naïve we must select CD4+ T cells having the naïve phenotype CD45RA. As we prefer not to touch the CD45RA T cells with antibodies, a negative selection process of these cells was used for the disclosed co-cultures. |

The invention claimed is:

1. A method comprising:
    a) obtaining autologous human CD4+CD45RA+CD4RO negative naïve newborn human T cells from a subject;
    b) co-culturing the autologous human CD4+CD45RA+CD4RO negative naïve newborn human T cells with a first population of human dendritic cells in the presence of human non-heat activated platelet-poor plasma;
    c) incubating the co-culture of dendritic cells and naïve T cells at least 7 days, about 7 days, or about 7-15 days sufficient to cause activation of the CD4+CD45RA+CD4RO negative naïve T cells to become CD4+CD45RO+ activated T cells;
    d) introducing to the CD4+CD45RO+ activated T cells from the culture of step b to a second population of human dendritic cells in the presence of human platelet-poor plasma and Bacille Calmette-Guérin (BCG), Pneumococcal conjugate vaccine (PCV), and/or Hepatitis B vaccine (HBV), and a stimulating agent;
    e) co-culturing the second population of dendritic cells and the CD4+CD45RO+ activated T cells of step c for a period of time;
    f) analyzing the co-culture media from step d to assess the stimulating agent's reactogenicity by comparing the lymphocyte proliferation of the BCG, PCV, HCV and stimulating agent samples and determining if the stimulating agent stimulated lymphocyte proliferation is at least as detected for the PCV sample; and
    g) further analyzing the co-culture of step d for Th2 polarization of neonatal immune responses by detecting the IL-4 secretion in the BCG, PCV, HBV and stimulating agent samples and determining if the stimulating agent is at least as potent to stimulate secretion of IL-4 as detected as for the PCV sample;
    h) assessing the determination of steps e and f and if the stimulating agent stimulated the lymphocyte proliferation at least as detected as for the PCV sample and the Il-4 secretion is at least as for the PCV sample, thereby determining reactogenicity and Th2 polarization of the stimulating agent; and
    i) administering the stimulating agent to the subject when the reactogenicity and Th2 polarization of the stimulating agent is determined to be less than that of PCV.

2. The method of claim 1, wherein
    (A) (i) the human CD4+CD45RA+naïve T cells are newborn cells and are CD45RO negative, or (ii) the human CD4+CD45RA+naïve T cells are newborn cells, the dendritic cells and the human newborn platelet poor plasma are autologous, meaning they come from one donor, and/or
    (B) the human platelet poor plasma is not heat inactivated, and/or
    (C) (i) the period of time sufficient to cause activation of the naïve T cells in culture is at least one day, and/or (ii) the method further comprises analyzing the cells of step (e) for cell proliferation wherein an increase in cell proliferation or cell number over that in the absence of added dendritic cells indicates that the antigen is effective in stimulating human naïve antigen-specific immune response and/or,
    (D) the stimulating agent is a vaccine to be evaluated, and/or
    (E) the stimulating agent being evaluated is the stimulating agent used in vitro to produce the first and second population of human dendritic cells, and/or
    (F) the method further comprises challenging the cells in culture of step (d) with a third population of human dendritic cells prior to analysis for cytokines and/or cell proliferation, wherein the third population of human dendritic cells were exposed to the same stimulating agent as the first and second population of human newborn dendritic cells in steps (a) and (d), optionally wherein the third population of human dendritic cells is also produced with the same stimulating agent being evaluated, and/or
    (G) the cytokine analyzed is selected from a group consisting of IL-1, IL-10, IL-12, IL-2, IL-4, IFN-gamma and TNF-alpha.

3. The method of claim 1, wherein the population of human dendritic cells is prepared by an in vitro method comprising:
    a) introducing an agent in the presence of human platelet-poor plasma to a tissue construct, wherein the tissue construct comprising:
        i. a cushion of extracellular matrix;
        ii. a monolayer human endothelial cells on the top of the cushion wherein the human endothelial cells were cultured to a monolayer in human serum albumin; and
        iii. human mononuclear cells (MCs) that have extravasated through the monolayer of human endothelial cells and are embedded and colonized the cushion of extracellular matrix;
    b) incubating the tissue culture for a period of time sufficient for the extravasated human MCs to reverse-transmigrate across the monolayer of human endothelial cells; and
    c) collecting the reverse-transmigrated human MCs which have developed into antigen-presenting dendritic cells in the presence of the agent.

4. The method of claim 3, wherein
(A) the human MCs are human CD 33+ and/or CD14+ monocytes, optionally wherein the human CD 33+ and/or CD14+ monocytes are from one donor, optionally wherein the human CD 33+ and/or CD14+ monocytes are not pooled from more than one donor, and/or
(B) the human CD 33+ and/or CD14+ monocytes are obtained from human umbilical cord blood, and/or
(C) the human serum albumin is pyrogen-free, and/or
(D) the human serum albumin is clinical grade human serum albumin, and/or
(E) the human MCs are not cultured in the presence of exogenous cytokines or immune response stimulating agent, and/or
(F) the human MCs are not cultured in the presence of GM-CSF, and/or
(G) the human MCs are not cultured in the presence of IL-4, and/or
(H) the human CD 33+ and/or CD14+ monocytes or human MCs and the human platelet poor plasma are autologous, meaning they come from one donor, and/or
(I) the human CD 33+ and/or CD14+ monocytes are obtained from human umbilical cord blood, and/or
(J) the human CD 33+ and/or CD14+ monocytes has been previously been cryopreserved, and/or
(K) the agent is any agent that can induce or stimulate development and transformation of the human MCs to antigen-presenting dendritic cells, optionally wherein the agent is a vaccine or an adjuvant, and/or wherein the agent is a pathogen, optionally wherein the pathogen is a fragment or an incomplete portion thereof or a whole intact pathogen, and/or
(L) the agent is any agent that is to be tested for its ability to induce or stimulate development and transformation of the human MCs to antigen-presenting dendritic cells, and/or
(M) the human platelet poor plasma is not heat inactivated, and/or
(N) the human platelet poor plasma is used at least at 50% in step b, and/or
(O) the human platelet poor plasma is used at about 50%-100% in step b, and/or
(P) the human platelet poor plasma is used at 100% in step b, and/or
(Q) the period of time sufficient to allow reverse-transmigration of the MCs across the monolayer of endothelial cells is at least 24 h, and/or
(R) the period of time sufficient to allow reverse-transmigration of the MCs across the monolayer of endothelial cells is about 24-48 h, and/or
(S) the period of time sufficient to allow reverse-transmigration of the MCs across the monolayer of endothelial cells is 48 h, and/or
(T) the human plasma, human newborn platelet poor plasma or human serum albumin does not contain a chelating agent, and/or
(U) the human plasma, human platelet poor plasma or human serum albumin is prepared with heparin, and/or
(V) the human plasma, human platelet poor plasma or human serum albumin is prepared in the absence of a chelating agent.

5. The method of claim 3, wherein
(A) the cushion of extracellular matrix comprises collagen, optionally,
  (i) wherein the collagen is human collagen, optionally wherein the human collagen is human Type 1 collagen, and/or wherein the collagen is glycated or wherein the cushion of extracellular matrix further comprising fibronectin, optionally wherein the fibronectin is human fibronectin, and/or wherein the human collagen is human collagen matured in the presence of glucose-6-phosphate, optionally wherein the human collagen is matured in the presence of glucose-6-phosphate for at least 48 h, or
  (ii) wherein the collagen is bovine collagen, optionally wherein the collagen is Type 1 collagen, and/or wherein the collagen is glycated, or wherein the cushion of extracellular matrix further comprising fibronectin, optionally wherein the fibronectin is human fibronectin, or
  (iii) wherein the collagen is porcine collagen, optionally wherein the collagen is Type 1 collagen, and/or wherein the collagen is glycated, or wherein the cushion of extracellular matrix further comprising fibronectin, optionally wherein the fibronectin is human fibronectin, or
wherein the collagen is human collagen matured in the presence of glucose-6-phosphate for up to 5 days, optionally from 2-5 days, from 2-3 days, from 2-4 days, from 3-4 days, from 4-5 days, or from 3-5 days, and/or
(B) wherein the endothelial cells are human primary endothelial cells, optionally wherein the human primary endothelial cells are cultured in the presence of human newborn or adult plasma, and/or wherein the human primary endothelial cells are obtained from one single donor, and/or wherein the human primary endothelial cells are obtained from human umbilical cord, and/or wherein the human primary endothelial cells are cultured to a confluent monolayer, optionally wherein the confluent monolayer is at least 90% confluent, and/or wherein the confluent monolayer is about 90%-100% confluent, and/or
(C) wherein the period of time to obtain a monolayer is at least 24 h, and/or wherein the period of time to obtain a monolayer is about 24 h to 3 days or about 24 h to 5 days, and/or
(D) wherein the human primary endothelial cells are cultured in the presence of human newborn plasma and wherein,
  (i) the human plasma is not heat inactivated, or the human plasma is heat inactivated, and/or
  (ii) the human plasma is from a newborn, an adult, an adolescent or a child, and/or
  (iii) the human plasma is plasma pooled from more than one donor, and/or
  (iv) the human plasma is obtained from human umbilical cord blood, placental blood or circulating peripheral blood, and/or
  (v) the human plasma has been previously been cryopreserved, and/or
(E) wherein
  (i) the human plasma is used at least 40%, and/or
  (ii) the human plasma at about 40%-100%, and/or
  (iii) the human plasma at about 50%, and/or
  (iv) the human plasma is human newborn plasma, and/or
  (v) the human MCs are from a newborn, an adult, an adolescent or a child, and/or
  (vi) the human MCs are derived from one donor, or the human MCs are not pooled from more than one donor, and/or
  (vii) the human MCs cells are cells previously cryopreserved, and/or (viii) the human MCs are obtained from human umbilical cord blood, placental blood or bone marrow, and/or
(xi) the human MCs are human newborn or adult MCs, or the human MCs are human CD 33+ and/or CD14+ monocytes, optionally wherein the human CD 33+ and/or CD14+ monocytes are from one donor, or wherein the human CD 33+ and/or CD14+ monocytes are not pooled from more than one donor, and/or wherein the human CD 33+ and/or CD14+ monocytes are human newborn CD 33+ and/or CD14+ monocytes, optionally wherein the human serum albumin is not heat inactivated, optionally wherein the human serum albumin is pyrogen-free, and/or wherein the human serum albumin is clinical grade human serum albumin, and/or
(x) the human CD 33+ and/or CD14+ monocytes are obtained from human umbilical cord blood, placental blood or bone marrow, and/or
(F) the human MCs or human CD 33+ and/or CD14+ monocytes are cultured in the presence of human serum albumin, optionally wherein the human CD 33+ and/or CD14+ monocytes are human newborn CD 33+ and/or CD14+ monocytes, optionally wherein the human serum albumin is not heat inactivated, optionally wherein the human serum albumin is pyrogen-free, and/or wherein the human serum albumin is clinical grade human serum albumin, and/or
(G) the human MCs are not cultured in the presence of exogenous cytokines or immune response stimulating agent, and/or
  (i) wherein the human MCs are not cultured in the presence of GM-CSF, or wherein the human MCs are not cultured in the presence of IL-4, and/or
  (ii) wherein the human CD 33+ and/or CD14+ monocytes or human MCs and the human platelet poor plasma are autologous, meaning they come from one donor, and/or
  (iii) wherein the human CD 33+ and/or CD14+ monocytes are obtained from human umbilical cord blood, placental blood or bone marrow, and/or
  (iv) wherein the human CD 33+ and/or CD14+ monocytes has been previously been cryopreserved, and/or
(H) the period of time sufficient to allow the human MCs to autonomously extravasate through the monolayer of endothelial cells and colonize the cushion of extracellular matrix is at least 0.5 h, and/or
  (i) wherein the period of time sufficient to allow the human MCs to autonomously extravasate through the monolayer of endothelial cells and colonize the cushion of extracellular matrix is about 0.5 h to 4 h, and/or
  (ii) wherein the period of time sufficient to allow the human MCs to autonomously extravasate through the monolayer of endothelial cells and colonize the cushion of extracellular matrix is about 1.5 h to 2 h, and/or
  (iii) wherein the agent is any agent that can induce or stimulate development of the human MCs to mature to dendritic cells, and/or
  (iv) wherein the agent is any agent that is to be tested for its ability to induce or stimulate development of the human MCs to mature to dendritic cells, or the agent is a vaccine formulation, or the agent is an adjuvant, and/or the agent is a pathogen, optionally wherein the pathogen is a fragment/incomplete portion thereof or a whole intact pathogen, and/or
(I) the human newborn platelet poor plasma is not heat inactivated, or the human newborn platelet poor plasma is used at least at 50% in step d, and/or
(J) wherein the human newborn platelet poor plasma is used at about 50%-100% in step d, and/or
(K) wherein the human newborn platelet poor plasma is used at about 100% in step d, and/or
(L) the period of time sufficient to allow reverse-transmigrated of the human MCs from the monolayer of endothelial cells is at least 24 h, and/or
  (i) wherein the period of time sufficient to allow reverse-transmigrated of the human MCs from the monolayer of endothelial cells is about 24-48 h, and/or
  (ii) wherein the period of time sufficient to allow reverse-transmigrated of the human MCs from the monolayer of endothelial cells is about 48 h, and/or
(M) the human plasma, human platelet poor plasma or human serum albumin does not contain a chelating agent, and/or
(N) the human plasma, human platelet poor plasma or human serum albumin is prepared with heparin, and/or
(O) the human plasma, human platelet poor plasma or human serum albumin is prepared in the absence of a chelating agent.

6. The method of claim 1, wherein the subject is a newborn.

* * * * *